(12) United States Patent
Toutov et al.

(10) Patent No.: US 9,809,607 B2
(45) Date of Patent: Nov. 7, 2017

(54) SILYLATION OF AROMATIC HETEROCYCLES BY EARTH ABUNDANT TRANSITION-METAL-FREE CATALYSTS

(71) Applicant: CALIFORNIA INSTITUTE OF TECHNOLOGY, Pasadena, CA (US)

(72) Inventors: Anton Toutov, Pasadena, CA (US); Kerry Betz, Boulder, CO (US); Alexey Fedorov, Wallisellen (CH); Brian M. Stoltz, San Marino, CA (US); Wenbo Liu, Pasadena, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/818,417

(22) Filed: Aug. 5, 2015

(65) Prior Publication Data
US 2016/0046653 A1   Feb. 18, 2016

(51) Int. Cl.
C08G 75/00 (2006.01)
C07F 7/08 (2006.01)
C07D 209/12 (2006.01)

(52) U.S. Cl.
CPC .......... *C07F 7/0801* (2013.01); *C07D 209/12* (2013.01); *C07F 7/0827* (2013.01); *C07F 7/0832* (2013.01)

(58) Field of Classification Search
CPC .... C07F 7/0801; C07F 7/0832; C07F 7/0827; C08G 75/00; C07B 51/00; C07D 209/12
See application file for complete search history.

(56) References Cited

U.S. PATENT DOCUMENTS 9,000,167 B2   4/2015 Grubbs et al.
2004/0192912 A1*  9/2004 Pendri ................. C07D 473/18
                                                        544/276
2016/0176772 A1   6/2016 Toutov

OTHER PUBLICATIONS

Bideau et al., Chem. Commun., 2001, 1408-1409.*
Dervan, et al., "Trimethylsilylpotassium. Deoxygenation of Epoxides With Inversion of Stereochemistry", J. Am. Chem. Soc., 1976, vol. 98, 1265-1267.
Haebich, et al., "Preparation of Aryl- and Heteroaryltrimethylsilanes", Synthesis, 1979, Issue 11, 841-876.
Kyalo, et al., "Palladium-catalyzed Direct C—H Silylation and Germanylation of Benzamides and Carboxamides", Org. Lett., 2014, vol. 16, 1968-1971.
Shippey, et al., "Trimethylsilyl Anions. Direct Synthesis of Trimethylsilybenzenes", J. Org. Chem., 1977, vol. 42, 2654-2655.

(Continued)

*Primary Examiner* — Shane Fang
(74) *Attorney, Agent, or Firm* — Baker & Hostetler LLP

(57) ABSTRACT

The present invention describes chemical systems and methods for silylating aromatic organic substrates, said system or method comprising or consisting essentially of a mixture of (a) at least one organosilane and (b) at least one strong base, the definition of strong base now also including KOH, said system being preferably, but not necessarily substantially free of a transition-metal compound, and said methods comprising contacting a quantity of the organic substrate with a mixture of (a) at least one organosilane and (b) at least one strong base, under conditions sufficient to silylate the aromatic substrate.

37 Claims, 10 Drawing Sheets

(56) References Cited

OTHER PUBLICATIONS

Ball et al., Science, "Gold-Catalyed Direct Arylation", Sep. 28, 2012, vol. 337(102), 1644-1648.
Bekele et al., "Improved Synthesis of the Boc and Fmoc Derivatives of 4-(2'-Aminoethyl)-6-dibenzofuranpropionic Acid: An Unnatural Amino Acid That Nucleates .beta.-Sheet Folding", Journal of Organic Chemistry, 1997, 62, 2259-2262.
Cheng, et al., "Rhodium-Catalyzed Intermolecular C—H Silylation of Arenes with High Steric Regiocontrol", Science, Feb. 2014, 343(6173), 853-857.
Cheve et al., "De Novo Design, Synthesis and Pharmacological Evaluation of New Azaindole Derivatives as Dual Inhibitors of Abl and Src kinases", Med Chem Comm, 2012, 3, 7, 788-800.
Collins, et al., "A Robustness Screen for the Rapid Assessment of Chemical Reaction", Nature Chem., Jun. 2013, 5, 597-601.
Curless, et al., "E—H (E=R3Si or H) Bond Activation by B(C6F5)3 and Heteroarenes; Competitive Debydrosilylation, Bydrosilyiation and Hydrogenation", Chem. Commun., Nov. 2013, 50, 5270-5272.
Denmark, et al., Palladium-Catalyzed Cross-Coupling Reactions of Silanolates: a Paradigm Shift in Silicon-Based Cross-Coupling Reactions. Chem. Eur., 2006, 2, 4954-4963.
Despotopoulou, et al., "Synthesis of Fully Substituted Pyrazoles via Regio- and Chemoselective Metalations", P. Org. Lett., Jul. 2009, 11(15), 3326-29.
Diez-Gonzalez, et al. , "Copper, Silver, and Gold Complexes in Hydrosilylation Reactions", Accounts of Chemical Research, vol. 41(2), Feb. 2008, 349-358.
Du, et al., "Semisynthesis of DB-6 7 and Other Silatecans from Camptotbecin by Thiol-Promoted Addition of Silyl Radicals", Bioorg. Med. Chem., Feb. 2003, 11(3), 451-458.
Fedorov, et al., "Lewis-Base Silane Activation: From Reductive Cleavage of Aryl Ethers to Selective Ortho-Silylation", Chem. Sci., Feb. 2013, 4, 1640-1645.
Franz, et al., "Organosilicon Molecules with Medicinal Applications", J Med. Chem.,Oct. 2012, 56(2), 388-405.
Frick, et al, "Elektrophile Silylierung Elektronenreicher Heteroaromaten", Synthesis, Nov. 1984, 929-930.
Furukawa, et al., "Development of a Sila-Friedel-Crafts Reaction and its Application to the Synthesis of Dibenzosilole Derivatives", J. Am. Chem. Soc., Sep. 2009, 131(40), 14192-14193.
Habich et al., "Preparation of Aryl- and Heteroaryltrimethylsilanes", Reviews, 1979, 841-876.
Hansen, et al., "Lithiated Benzothiophenes and Benzofurans Require 2-Silyl Protection to Avoid Anion Migration", Revue, 2004, 8, 1351-1354.
Harneet, et al., "(NHC)Cul (NHC=N-Heterocyclic Carbene) Complexes as Efficient Catalysts for the Reduction of Carbonyl Compounds", Organometallics, 2004, 23(5), 1157-1160.
Huckins, et al., "Synthesis of Optically Pure Arylsilylcarbinols and Their Use as Chiral Auxiliaries in Oxacarbenium Ion Reactions", Journal of Organic Chemistry, 2003, 68, 10135-10145.
Huestis, et al., "Site-Selective Azaindole Arylation at the Azine and Azole Rings via N-Oxide Activation", Org Lett., Mar. 2009, 11(6), 1357-60.
Islam, et al., "On water", Phosphine-Free Palladium-Catalyzed Room Temperature C—H Arylation of Indoles., Chem. Eur. J., 2013, 19, 15093-15096.
Kakiuchi, et al., "Ru3 (C0) $_{12}$-Catalyzed Silylation of Benzylic C—H Bonds in Arylpyridines and Arylpyrazoles with Hydrosilanes via C—H Bond Cleavage", J A.m. Chem. Soc., Sep. 2004, 126(40), 12792-12793.
Klare, et al., "Cooperative Catalyic Activation of Si—H bonds by a Polar Ru—S Bond: Regioselective Low-Temperature C—H Silyiation of Indoles Under Neutral Conditions by a Friedel-Crafts Mechanism", J. Ant Chem. Soc., Feb. 2011, 133(10), 3312-3315.
Kong, et al., "Highly Efficient Construction of Benzene Ring in Carbazoles by Palladium-Catalyzed Endo-Mode Oxidative Cyclization of 3-(3'-alkenyl)indoles.", Org. Lett., 2006, 8, 1339-1342.
Konigs et al, "Base-Free Dehydrogenative Coupling of Enolizable Carbonyl Compounds with Silanes", Org. Lett., 2012, vol. 14(11), 2842-2845.
Kuznetsov et al., General and Practical One-Pot Synthesis of Dihydrobenzosiloles from Styrenes, Org. Lett., Jan. 2012, 14(3), 914-917.
Kuznetsov, et al., "Fused Heteroaromatic Dihydrosiloles: Synthesis and Double-Fold Modification", Org. Lett., Apr. 2013, 15(10), 2498-2501.
Langkopf, et al., "Uses of Silicon-Containing Compounds in the Synthesis of Natural Products", Chem. Rev., Jul. 1995, 95(5), 1375-1408.
Lee, et al., "Highly Selective and Practical Hydrolytic Oxidation of Organosilanes to Silanols Catalyzed by a Rutheniurn Complex", J Am. Chem. Soc., 2000, 122(48), 12011-12012.
Li, et al., "Green Chemistry f(Ir chernical Synthesis", Proc. Natl Acad. Sci., 2008, 105, 13197-13202.
Lu, et al., "Efficient Iridium-Catalyzed C—H Functionalization/ Silylation of Heteroarenes", Angew. Chem., Int. Ed., Aug. 2008, 47(39), 7508-7510.
Mahadevan, et al., "Ambident Heterocyclic Reactivity: The Alkylation of Pyrrolopyridines (azaindoles, diazaindenes)", Aug. 1993, 49(33), 7337-52.
Mita, et al., "Sequential Protocol for C(sp3_-H Carboxylation with CO2: Transition-Metal-Catalyzed Benzylic C—H Silylation and Fluoride-Medicated Carboxylation", Organic Letters, Jun. 19, 2012, vol. 14(13), 3462-3465.
Nishihara, et al., "Palladium/Copper-Catalyzed Sila-Sonogashira Reactions of Aryl Iodides with Alkynylsilanes via a Direct C—Si Bond Activation", Tetrahedron Letters, 50, Jun. 2009, 4643-4646.
Oyamada, et al., "Scandium-Catalyzed Silylation of Aromatic C—H bonds", Angew. Chem. Int. Ed., Sep. 2011, 50, 10720-10723.
Park et al., "Transition Metal-Catalyzed Ortho-Functionalization in Organic Synthesis", Bull. Korean Chem. Soc., 2005, vol. 26(6), 871-877.
Sakakura, et al., "Catalytic C—H Activation. Silylation of Arenes with Hydrosilane or Disilane by RhCl (CO)(PMe)$_2$ Under Irradiation", Chem. Lett., 1987,16(12), 2375-2378.
Seiple, et al., "Direct C—H Arylation of Electron-Deficient Heterocycles with Arylboronic Acids", J. Am. Chem. Soc., Sep. 2010, 132(38), 13194-13196.
Seregin, et al., "Direct Transition Metal-Catalyzed Functionalization of Heteroaromatic Compounds", Chem. Soc. Rev., Mar. 2007, 36, 1173-1193.
Showell, et al., "Chemistry Challenges in Lead Optimization: Silicon Isosteres in Drug Discovery", Drug Discov., Jun. 2003, 8(12), 551-556.
Song, et al., "Organometallic Methods for the Synthesis and Functionalization of Azaindoles", Chem. Soc. Rev., Feb. 2007, 36, 1120-1132.
Tamao, et al., "Silole Derivatives as Efficient Electron Transporting Materials", J. Am. Chem. Soc., Nov. 1996, 118(47), 11974-11975.
Ting, et al., "Arylfuoroborates and Alkylfluorosilicates as Potential PET Imaging Agents: High-Yielding Aqueous Biomolecular 18F-Labeling", J. Am. Chem. Soc., Sep. 2005, 127(38), 13094-13095.
Toutov, et al., "Silylation of C—H Bonds in Aromatic Heterocycles by an Earth-Abundant Metal Catalyst", Nature, Feb. 2015, 518, 80-84.
Wang, et al., "Transition-Metal-Free Synthesis of Alternating Thiophene-Periluoroarene Copolymers", J. Am. Chem. Soc., Feb. 2006, 128(8), 2536-2537.
Weickgenannt, et al., "Potassium tert-Butoxide-Catalyzed Dehydrogenative Si—O Coupling: Reactivity Patten and Mechanism of an Underappreciated Alcohol Protection", Chem. Asian J., Jan. 2009, 4(3), 406-410.
Whisler, et al., "Beyond Thermodynamic Acidity: A Perspective on the Complex-Induced Proximity Effect (CIPE) in Deprotonation Reactions", Angew. Chem., Int Ed., Apr. 2004, 43(17), 2206-2225.
Zhang, et al., "Thiophene-Based Conjugated Oligomers for Organic Solar Cells", J. Mater. Chem., Sep. 2011, 21, 17590-17600.

(56) References Cited

OTHER PUBLICATIONS

Zhao, et al., "Directed Ortho Metalation-Based Methodology. Halo-, Nitroso-, and Boro-Induced ipso-Desilylation. Link to an in situ Suzuki Reaction", Org. Lett., May 2005, 7(13), 2523-2526.

* cited by examiner (from antihistamine thenalidine)

(from antiplatelet agent ticlopidine)

SILYLATION OF AROMATIC HETEROCYCLES BY EARTH ABUNDANT TRANSITION-METAL-FREE CATALYSTS

GOVERNMENT RIGHTS

This invention was made with government support under Grant No. CHE1212767 awarded by the National Science Foundation. The government has certain rights in the invention.

CROSS REFERENCE TO RELATED APPLICATIONS

This application claims priority to U.S. Patent Application Nos. 62/033,975, filed Aug. 6, 2014; 62/094,381, filed Dec. 19, 2014; and 62/141,905, filed Apr. 2, 2015, the contents of which are incorporated by reference herein for all purposes.

TECHNICAL FIELD

The present invention is directed at methods for silylating aromatic substrates, including heteroaromatic substrates, using hydroxide (especially potassium hydroxide) and silane reagents.

BACKGROUND

The ability to silylate organic moieties has attracted significant attention in recent years, owing to the utility of the silylated materials in their own rights or as intermediates for other important materials used, for example, in agrichemical, pharmaceutical, and electronic material applications. Further, the ability to functionalize polynuclear aromatic compounds with organosilanes provides opportunities to take advantage of the interesting properties of these materials.

Historically, the silylation of aromatic compounds has been achieved via free radical processes involving thermally, photochemically, or by otherwise derived radical sources. Aromatic compounds are known react with silicon hydrides in the gas phase at 500-850° C., in the liquid phase under autogeneous pressure at 350-500° C., in the presence of peroxides at 135° C. under gas phase condensations, and using electrical discharge reactions. Such reactions conditions are not amenable to non-volatile or thermally sensitive materials.

At present, the most common approach to heteroaromatic C—Si bond construction involves the interception of heteroaryl lithium or magnesium reagents with silicon electrophiles. However, this method is often limited in scope and requires prefunctionalization of heteroarenes by using pyrophoric organometallic species in stoichiometric quantities. Powerful heteroaromatic functionalization strategies, such as Minisci-type radical substitutions and Friedel-Crafts reactions, have been of limited use for C—Si bond construction owing to the difficulty of generating the corresponding silyl radicals and silylium ions.

More recently, the transition metal mediated aromatic C—H silylation has been described, with different systems described based on, for example, Co, Rh, Ir, Fe, Ru, Os, Ni, Pd, and Pt catalysts. But certain electronic applications, the presence of even low levels of such residual can adversely affect the performance of the silylated materials. Similarly, in certain pharmaceutical or electronic applications, limits on residual transition metals are fairly strict, and the ability to avoid them entirely offers benefits during post-synthesis work-up.

The present invention takes advantage of the discoveries cited herein to avoid at least some of the problems associated with previously known methods.

SUMMARY

The present disclosure provides new information with respect to the butoxide catalyzed silylation of aromatic substrates as well as the recent discovery that KOH (potassium hydroxide), can be made operable as a catalyst in the present reactions. Contrary to earlier findings, it has now been found that KOH can be an effective catalyst for the direct silylation of heteroaromatic substances with hydrosilanes under certain conditions. It now appears that by modifying the reaction conditions, this KOH catalyst system can be used with every substrate in which potassium tert-butoxide or other "strong bases") was previously shown to be effective, but where KOH was previously shown to be unworkable, for example, as described in U.S. patent application Ser. No. 14/043,929 and International Application No. PCT/US2013/062963, both filed Oct. 2, 2013. The use of KOH offers important practical benefits such as lower cost and toxicity, easier handling, and facilitated reaction set up and purification. Additionally, it provides a selectivity not seen in reactions using stronger bases, including alkoxides.

This specification also discloses additional embodiments, described in terms of potassium tert-butoxide, not previously explicitly described, showing a more complete set of examples of the versatility of these methods.

Various embodiments of the present invention provide chemical systems for silylating organic compounds, each system comprising or consisting essentially of a mixture of (a) at least one organosilane and (b) at least one strong base, the definition of said strong base now also including KOH, said system also operable to silylate an aromatic precursor when conducted preferably substantially free of a transition-metal compound. The system further comprises at least one organic aromatic substrate.

Other embodiments provide methods, each method comprising contacting the organic aromatic substrate with a mixture comprising or consisting essentially of (a) at least one organosilane and (b) at least one strong base, the definition of said strong base now also including KOH, under conditions sufficient to silylate the substrate. In some embodiments, said mixture and substrate are preferably, but not necessarily, substantially free of a transition-metal compound.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 4A shows a schematic of the preparation of 142 g of C2-silylated indole building block 2a. FIG. 4B illustrates certain applications of heteroarylsilanes in cross-coupling and a formal C—H borylation at C7 of benzothiophene. FIG. 4C illustrates certain embodied syntheses of selective precursors to advanced materials and polymers. FIG. 4D illustrates the selective examples of the inventive methods used to prepare late-stage chemo- and regioselective modification of active pharmaceutical ingredients. FIG. 4E shows examples of functionalization of arenes by oxygen-directed sp$^2$, and innate benzylic sp$^3$ C—H silylation. See Examples 6.7.1 to 6.7.4 for details. [Si]=Et$_3$Si; i-Pr, isopropyl; dba, dibenzylideneacetone; Bpin, 4,4,5,5-tetramethyl-1,3,2-dioxaborolane; TMEDA, tetramethylethylenediamine; EDOT, 3,4-ethylenedioxythiophene.

FIG. 5A shows the overall conversion as a function of time and FIG. 5B shows the ratio of C2:C3 as a function of time. Top curves (squares) is for 20 mol % KOH and bottom curves are for 5 mol %.

DETAILED DESCRIPTION OF ILLUSTRATIVE EMBODIMENTS

Figure 1A:
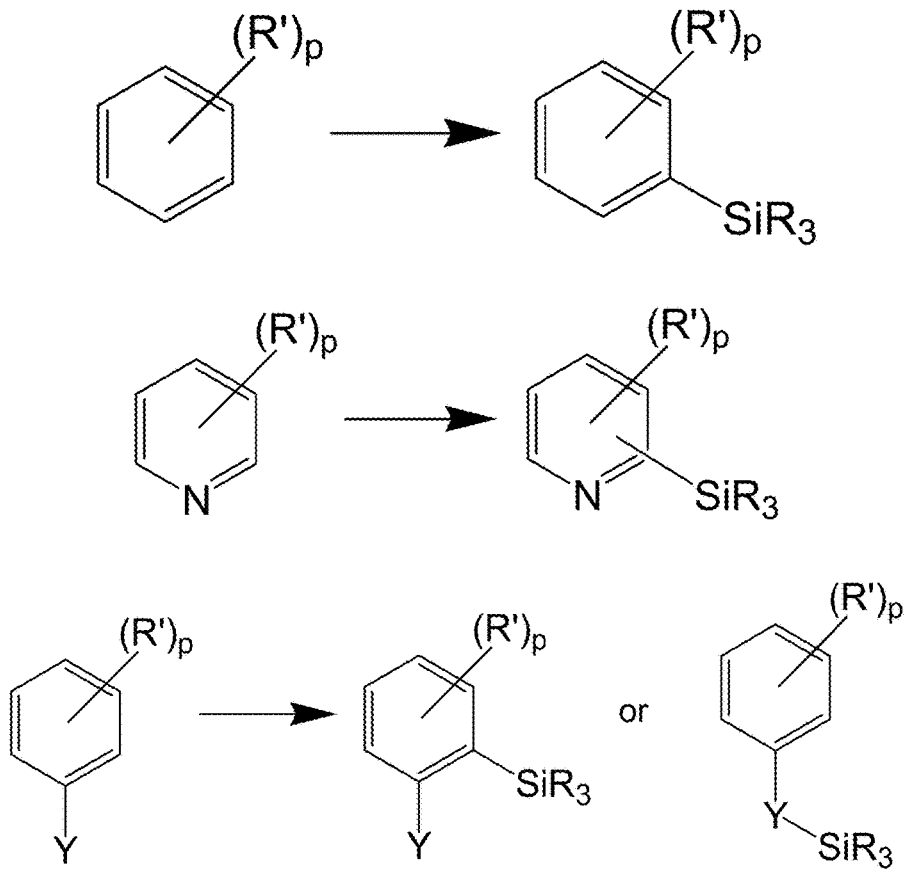
FIGS. 1A and 1B illustrate examples of some of the reactions available by the methods described herein.
Figure 1B:
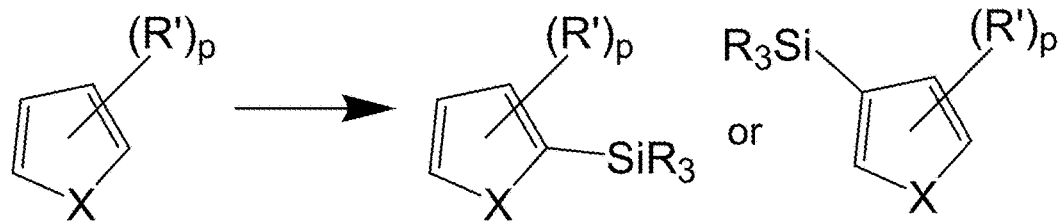

The present invention is founded on a set of reactions, each of which relies on simple mixtures of organosilanes and strong bases, the definition of said strong bases now also including hydroxide, especially KOH, which together form in situ systems (the structure and nature of the active species is still unknown) able to silylate aromatic molecules, especially heteroaryl compounds, in the liquid phase, without the presence of transition metal catalysts, UV radiation or electrical (including plasma) discharges. These reactions are relevant as an important advance in developing practical methods for the preparation of products important for pharmaceutically and electronics applications. Importantly this reaction is of great interest since it produces only environmentally benign silicates and dihydrogen as the byproduct and can avoid toxic metal waste streams as would be observed with nearly all other approaches proposed in the literature towards this end. The remarkable facility and regiospecificity exhibited by at least some of these systems provides a useful tool in the kit of chemists in these fields.

The present disclosure includes some information previously presented in U.S. patent application Ser. No. 14/043,929 and International Application No. PCT/US2013/062963, both filed Oct. 2, 2013, as well as new additional embodiments described in terms of potassium tert-butoxide, not previously explicitly described, showing a more complete set of embodiments of the versatility of these methods. The disclosure further provides data related to the recent discovery that KOH (potassium hydroxide), and other hydroxides, can be made operable as a catalyst in the present reactions. Contrary to earlier findings, it has now been found that KOH can be an effective catalyst for the direct silylation of heteroaromatic substances with hydrosilanes under certain conditions. Whereas many of the examples provided herein are described in terms of tert-butoxide, hydrides, etc., these examples can also be extended to include those where KOH is the operative catalyst, and embodiments described in terms of the former also extend to those using the latter. Likewise, comments on the operability of tert-butoxide systems (e.g., tolerance to functional groups) are explicitly intended to reflect also on the operability of KOH systems.

The silylation reactions described herein proceed under mild conditions, in the absence of hydrogen acceptors, ligands or additives, and is scalable to greater than 100 grams under optionally solvent-free conditions. Substrate classes that are difficult to activate with precious metal catalysts are silylated in good yield and with excellent regioselectivity. The derived heteroaryl silane products readily engage in versatile transformations enabling new synthetic strategies for heteroaromatic elaboration, and are useful in their own right in pharmaceutical and materials science applications.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function.

The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods or the compositions derived therefrom) to silylate aromatic organic moieties. In those embodiments that provide a system or method comprises the use of a mixture consisting essentially of the substrate, organosilane (alternatively referred to as hydrosilane), and strong base (the definition of strong base now also including hydroxide, especially KOH), it refers to the fact that this system operates to silylate the substrate at rates corresponding to those described herein under comparable conditions as described herein without additional (e.g., transition metal) catalysts or plasma or UV radiation sources. While some level of transition metals may be present, they are not needed for the operability of the methods, and may be considered spectators for purposes of this reaction. Indeed, extensive experiments and analyses conducted rule out catalysis by adventitious transition metal residues (see Examples 3.1 to 3.3). Similarly, while other previous silylation reactions have employed plasma or UV irradiation to operate, the present invention does not require these energy sources. The additional presence of these energy sources should not be seen as replacing the basis underlying operability of the present methods.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a designation such as $C_{1-3}$ includes $C_1$, $C_2$, $C_3$, $C_{1-2}$, $C_{2-3}$, $C_{1,3}$, as separate embodiments, as well as $C_{1-3}$.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom, if not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, alk-heteroaryl moieties, or pre-polymeric (e.g., monomeric, dimeric), oligomeric or polymeric analogs thereof. While the descriptions of the methods and systems involving KOH are provided in terms of heteroaromatic substrates, where their operability is preferred, it is reasonably believed that they also work on aryl substrates.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(O)-alkyl, —O(O)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably it to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing such "aromatic moieties." The term "aromatic moieties" is intended to refer to those portions of the compounds, pre-polymers (i.e., monomeric compounds capable of polymerizing), oligomers, or polymers having at least one of the indicated aromatic structure. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano (—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl) substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(O)-aryl), imino (—CR═NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N (alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, $C_6$-$C_{24}$ aralkyl, etc.), nitro (—NO$_2$), nitroso (—NO), sulfo (—SO$_2$OH), sulfonate (SO$_2$—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H)alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-isopropylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. Preferred substituents are those identified herein as not or less affecting the silylation chemistries, for example, including those substituents comprising alkyls; alkoxides, aryloxides, aralkylalkoxides, protected carbonyl groups; aryls optionally substituted with F, Cl, —CF$_3$; epoxides; N-alkyl aziridines; cis- and trans-olefins; acetylenes; pyridines, primary, secondary and tertiary amines; phosphines; and hydroxides.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

As used herein, the term "silylating" refers to the forming of carbon-silicon bonds in a position previously occupied by a carbon-hydrogen bond, generally a non-activated C—H bond. The ability to replace directly a C—H bond with a C—Si bond, under the conditions described herein, is believed to be unprecedented.

The present invention includes embodiments related chemical systems and methods for silylating aromatic compounds and aromatic moieties. Specific embodiments provide chemical systems for silylating aromatic compounds and aromatic moieties, each system comprising a mixture of (a) at least one organosilane and (b) at least one strong base, the definition of said strong base now also including hydroxide, especially KOH, said system being preferably, but not necessarily, substantially free of a transition-metal compound.

It is recognized that the systems and reactions which provide for the silylation of aromatic compounds and aromatic moieties, under different conditions (mainly at higher temperatures), are also capable of cleaving C—O, C—N, C—S bonds within aromatic substrates. This latter reductive cleavage feature is the subject of a co-pending U.S. patent application Ser. No. 14/043,917, filed Oct. 2, 2013, entitled "Transition-Metal-Free Reductive Cleavage of Aromatic C—O, C—N, and C—S Bonds by Activated Silanes" which is also incorporated by reference in its entirety for all purposes. The mechanism by which the system and methods operate is not yet understood, for example, whether the silylation is an intermediate step or a co-product or by-product of the cleavage reactions (certain observations suggest not), but it does appear that the relative contribution of each manifold can be manipulated by the reaction conditions. For example, other factors being similar or equal and with certain exceptions, it appears that higher temperatures and longer reaction times tend favor the cleavage of C—O, C—N, C—S bonds over the silylation reactions (which occur at relatively milder temperatures). Similarly, absence of hydrogen and hydrogen donor molecules (even at the higher temperatures) and use of sub-stoichiometric quantities of the strong base, the definition of said strong base now also including hydroxide, especially KOH (relative to the organosilane) appear to favor the silylation reactions and disfavor the C—X cleavages.

Preliminary mechanistic investigations for at least the silylation of heteroaromatics suggest the involvement of radical species, though a continuum of mechanism may be operable. An elementary silyl radical generation-substitution mechanism seems to be unlikely owing to poor reactivity with electron deficient heteroarenes, such as pyridine (e.g., Example 6.9.49 to 51). Moreover, the rate of silylation was greater in sulphur-containing heteroarenes than in oxygen-containing heteroarenes, and was greater in oxygen-containing heteroarenes than in nitrogen-containing heteroarenes, as observed in an internal competition study (see, e.g., Example 7.1), which provided complementary reactivity to electrophilic substitutions and Minisci-type reactions. These observations pointed to an underlying mechanism that is distinct from known heteroaromatic functionalization reactions.

As used herein, the term "substantially free of a transition-metal compound" is intended to reflect that the system is effective for its intended purpose of silylating aromatic compounds and aromatic moieties under the relatively mild conditions described herein, even in the absence of any exogenous (i.e., deliberately added or otherwise) transition-metal catalyst(s). While certain embodiments provide that transition metals, including those capable of catalyzing silylation reactions, may be present within the systems or methods described herein at levels normally associated with such catalytic activity, the presence of such metals (either as catalysts or spectator compounds) is not required and in many cases is not desirable. As such, in preferred embodiments, the system and methods are "substantially free of transition-metal compounds." Unless otherwise stated, then, the term "substantially free of a transition-metal compound" is defined to reflect that the total level of transition metal within the silylating system, independently or in the presence of organic substrate, is less than about 5 ppm, as measured by ICP-MS as described in Example 3.3 below. Additional embodiments also provide that the concentration of transition metals is less than about 10 wt %, 5 wt %, 1 wt %, 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include Co, Rh, Ir, Fe, Ru, Os, Ni, Pd, Pt, Cu, or combinations thereof. In further specific independent embodiments, the concentration of Ni, as measured by ICP-MS, is less than 25 ppm, less than 10 ppm, less than 5 ppm, or less than 1 ppm.

These systems typically comprise hydrocarbon or ether-based solvents, or the systems can be operated without solvent. As described herein, solvents such as benzene, toluene, mesilylene, and tetrahydrofurans (including 2-methyltetrahydrofuran) have been shown to work well. In certain embodiments, the reactions are done in neat substrates.

While it may not be necessary to limit the system's exposure to water and oxygen, in some embodiments, the chemical systems and the methods are done in an environment substantially free of water, oxygen, or both water and oxygen. In other embodiments, air and/or water are present. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5%, 1%, 0.5%, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr. In the General Procedure described herein, deliberate efforts were made to exclude both water and oxygen, unless otherwise specified.

As used herein to describe the systems and methods, the terms "organosilane" or "hydrosilane" may be used interchangeably and refer to a compound or reagent having at least one silicon-hydrogen (Si—H) bond. The organosilane may further contain a silicon-carbon, a silicon-oxygen, a silicon-nitrogen bond, or a combination thereof, and may be monomeric, or contained within an oligomeric or polymeric framework, including being tethered to a heterogeneous or homogeneous support structure. In certain embodiments, these organosilane may comprise at least one compound of Formula (I) or Formula (I):

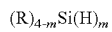

$$(R)_{4-m}Si(H)_m \quad (I)$$

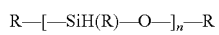

$$R—[—SiH(R)—O—]_n—R \quad (II)$$

where: m is 1, 2, or 3, preferably 1 or 2;

n is in a range of from about 5 to about 500, from about 10 to about 100 or from about 25 to about 50; and each R is independently optionally substituted $C_{1-12}$ alkyl or heteroalkyl, optionally substituted $C_{5-20}$ aryl or $C_{4-20}$ heteroaryl, optionally substituted $C_{6-30}$ alkaryl or $C_{4-30}$ heteroalkaryl, optionally substituted $C_{6-30}$ aralkyl or $C_{4-30}$ heteroaralkyl, optionally substituted —O—$C_{1-12}$ alkyl or heteroalkyl, optionally substituted —O—$C_{5-20}$ aryl or —O—$C_{4-20}$ heteroaryl, optionally substituted —O—$C_{6-30}$ alkaryl or —O—$C_{4-30}$ heteroalkaryl, or optionally substituted —O—$C_{6-30}$ aralkyl or —O—$C_{4-30}$ heteroaralkyl, and, if substituted, the substituents may be phosphonato, phosphoryl, phosphanyl, phosphine, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanates, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. Exemplary-, non limiting organosilanes include $(R)_3SiH$, where R is $C_{1-6}$ alkyl, particularly triethylsilane and tributylsilane, mixed aryl alkyl silanes, such as $PhMe_2SiH$, and polymeric materials, such as polymethylhydrosiloxane (PMHS). The use of organosilanes of general structure $(R)_2SiH_2$ also work well, and provide for opportunities for coupling or bridging reactions.

As used herein, the term "strong base" refers to a compound having a strong affinity for hydrogen atoms especially, but not only, in non-aqueous media. In specific independent embodiments, the at least one strong base comprises an alkali or alkaline metal hydride or alkoxide. It should be appreciated, then, that this definition is not strictly limited to the classic conjugate acid-base model—since the conjugate acid of hydride would be dihydrogen. One measure of this "strong affinity" may be that the strong base, if reacted with water, would react to the practically complete formation of hydroxide therefrom. Other "strong bases" may be considered as including alkyl lithium compounds or amide ions, for example potassium bis(trimethylsilyl)amide. Again, these descriptions have previously been used to describe alkoxide, alkyl (e.g., alkyl lithium compounds), amide ions, hydrides, and other extremely strong bases, hi the context of previous disclosures, these descriptions were used in context of materials described as "superbases." It is now discovered that the term "strong base" may also be considered to encompass hydroxides, particularly KOH (potassium hydroxide), within the scope of this invention.

Useful alkoxides include those comprising a $C_{1-12}$ linear or branched alkyl moieties or a $C_{5-10}$ aromatic or $C_{4-10}$ heteroaromatic moieties, for examples methoxide, ethoxide, propoxide, butoxide, 2-ethyl-hexyloxide, or benzyloxide. Each of these appears to give comparable reactivity. Further, the choice of the counter cation also impacts the effectiveness of the activity of the chemical system, such that potassium is preferred. More specifically, potassium methoxide, ethoxide, and tert-butoxide and cesium 2-ethylhexyl alkoxide have been shown to be effective in this role. By comparison, the reaction of $Et_3SiH$ with lithium or sodium tert-butoxide provides little or no reactivity suggesting that the counter ion plays a critical role in the generation of the active silylating species and, possibly, in activation of the substrate ether, or both. Similarly, conducting reactions with potassium tert-butoxide in the presence of sufficient 18-crown-6 to act as a potassium chelator resulted in nearly complete inhibition of the reaction.

Hydroxides such as potassium hydroxide (KOH) are now, for the first time, considered to be useful sources of base in the inventive methods. The hydroxide, KOH, may be formed in situ, for example by the reaction of metallic metal (e.g., potassium) with water, but in preferred embodiments, the hydroxide (e.g., KOH) is deliberately added as such, and preferably anhydrously (i.e., in the absence of water). It does not appear that the conditions of the reactions previously described generated sufficient KOH for it to work in this capacity.

While the relative amounts of organosilane and strong base, the definition of said strong base now also including hydroxide, especially KOH, is not believed to be particularly important, so long as both are present in sufficient quantities, in certain embodiments, the organosilane and the at least one strong base, the definition of said strong base now also including hydroxide, especially KOH, are present together at a molar ratio, with respect to one another, in a range of from about 20:1 to about 1:1. In other embodiments, these ratios may be on the order of about 5:1 to about 1:1, from about 3:1 to about 1:1, or from about 3:2 to about 1:1. The silylation reactions appear also to favor those conditions where the base is sub-stoichiometric, 0.01:1 to 0.9:1, with respect to the substrate, especially for more active systems. Further embodiments provide that the base is present with respect to the substrate at a ratio of from about 0.01:1 to about 0.6, or from about 0.1:1 to about 0.6. See, e.g., Table 6.

Further embodiments provide systems further comprising N-based compounds (preferably N-based chelants) including, for example, optionally substituted tetraalkylethylenediamine (e.g., tetramethylethylenediamine), optionally substituted 1,10-phenanthroline derivatives, optionally substituted 2,2'-bipyridine derivatives, and optionally substituted 4-dimethylaminopyridine derivatives. See, e.g., Example 2 and Table 2.

To this point, the invention has been described in terms of the chemical system capable of silylating aromatic compounds or moieties, but it should also be apparent that the invention also includes the methods of carrying out these transformations. That is, various additional embodiments include those methods where an organic substrate comprising an aromatic moiety is contacted with any of the chemical systems described above under conditions sufficient to silylate at least a portion of the substrate. That is, certain embodiments provide methods, each method comprising contacting an organic substrate comprising an aromatic moiety with a mixture of (a) at least one organosilane and (b) at least one strong base, the definition of said strong base now also including hydroxide, especially KOH, under conditions sufficient to silylate the substrate; wherein said mixture and substrate are preferably, but not necessarily, substantially free of a transition-metal compound. These embodiments are generally done in the liquid phase, without UV irradiation or electric or plasma discharge conditions.

In some embodiments, the conditions sufficient to silylate the organic substrate comprise heating the substrate with a mixture of (a) the at least one organosilane and (b) the at least one strong base, the definition of said strong base now also including hydroxide, especially KOH, at a temperature in a range of about 10° C. to about 165° C. In some cases, the temperatures may be applied in a range of from about 20° C., about 30° C., about 40° C., about 50° C., about 60° C., or about 80° C. to about 165° C., about 150° C., about 125° C., about 100° C., or to about 80° C. Any of the temperatures described in the Examples may be considered independent embodiments. Typical operating reaction times may range from about 2 hours, from about 4 hours, from about 6 hours, or from about 10 hours to about 28 days, to about 14 days, to about 7 days, to about 4 days, to about 3 days, to about 48 hours, to about 24 hours, to about 12 hours, or to about 6 hours.

As described above, those features described as relevant for the chemical systems for silylating aromatic compounds and aromatic moieties are also relevant for the methods of silylating these aromatic compounds and aromatic moieties. For example, in various embodiments, the methods provide that the system is substantially free of water, oxygen, or both water and oxygen.

In other embodiments, at least one organosilane comprises an organosilane of Formula (I) or Formula (II):

$$(R)_{4-m}Si(H)_m \quad\quad (I)$$

$$R\text{—}[\text{—}SiH(R)\text{—}O\text{—}]_n\text{—}R \quad\quad (II)$$

where m is 1, 2, or 3 (preferably 1 or 2);
n is 10 to 100; and
each R is independently optionally substituted $C_{1-12}$ alkyl or heteroalkyl, optionally substituted $C_{5-20}$ aryl or $C_{4-20}$ heteroaryl, optionally substituted $C_{6-30}$ alkaryl or $C_{4-30}$ heteroalkaryl, optional optionally substituted $C_{6-30}$ aralkyl or heteroaralkyl, optionally substituted —O—$C_{1-12}$ alkyl or heteroalkyl, optionally substituted —O—$C_{5-20}$ aryl or —O—$C_{4-20}$ heteroaryl, optionally substituted —O—$C_{6-30}$ alkaryl or $C_{4-30}$ heteroalkaryl, or optionally substituted —O—$C_{6-30}$ aralkyl or —O—$C_{4-30}$ heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

In still other embodiments, the organosilane is $(R)_3SiH$, where R is $C_{1-6}$ alkyl, preferably $Et_3SiH$ or $Et_2MeSiH$, or $(R)_2SiH_2$. The at least one strong base may comprise an alkali or alkaline metal hydride, as described above, for example, calcium hydride or potassium hydride. The at least one strong base may comprise an alkali or alkaline metal alkoxide, as described above, for example, where the at least one alkoxide comprises a $C_{1-12}$ linear or branched alkyl moiety or a $C_{5-10}$ aryl or $C_{4-10}$ heteroaryl moiety, preferably methoxide, ethoxide, propoxide, butoxide, or 2-ethyl-hexyl alkoxide. The alkali metal cation is preferably potassium or cesium. In most preferred embodiments, the organosilane is triethylsilane, trimethyl diethylmethylsilane, diethylsilane, dimethylsilane, dimethylethylsilane, ethyldimethylsilane, dimethylphenylsilane, diethylphenylsilane and the strong base is potassium tert-butoxide. The strong base may now include potassium hydroxide. Other combinations or exemplified reactants provide additional embodiments in this regard.

In certain embodiments, the organosilane (or monomer equivalent) and the at least one strong base, the definition of said strong base now also including hydroxide, especially KOH, are present together at a molar ratio, with respect to one another, in a range of from about 20:1 to about 1:1. In certain embodiments the at least one strong base, including KOH, and organic substrate are present together at a molar ratio, with respect to one another, in a range of from about 0.01:1 to about 5:1. Preferably the base is sub-stoichiometric—i.e., in a ratio of 0.01:1 to 0.9:1—with respect to the organic substrate. That is, the methods may be considered to be catalytic with respect to the bases contemplated herein.

Additionally, in the context of the methods, the term "substantially free of a transition-metal compound" carries the same connotations and related embodiments as described supra for the chemical system; i.e., reflecting that the methods are effectively conducted in the absence of any deliberately added transition-metal catalyst(s). Unless otherwise stated, when describing a method or system, the term is defined to reflect that the total level of transition metal, as measured by ICP-MS as described in Example 3.3 below, is less than about 50 ppm. Additional embodiments also provide that the concentration of transition metals is less than about 10 wt %, 5 wt %, 1 wt %, 100 ppm, 50 ppm, 30 ppm, 25 ppm, 2.0 ppm, 15 ppm, 10 ppm, or 5 ppm to about 1 ppm or 0 ppm, relative to the weight of the total system (i.e., both respect to the silylation system and the silylation system and the organic substrate). As used herein, the term "transition metal" is defined at least to include Co, Rh, Ir, Fe, Ru, Os, Ni, Pd, Pt, Cu, or combinations thereof. In further independent embodiments, the concentration of Ni, as measured by ICP-MS, is less than 25 ppm, less than 10 ppm, less than 5 ppm, or less than 1 ppm. Noting here that certain embodiments of the chemical system may comprise the at least one organosilane, and strong base, the definition of said strong base now also including hydroxide, especially KOH, it should be appreciated that independent embodiments provide that the levels of transition metals are maintained below the levels just described, when considering each of these mixture combinations.

Further embodiments provide that the methods further comprise using sub-stoichiometric amounts (relative to the substrate) of N-based compounds including (preferably N-based chelants), for example, optionally substituted tetraalkylethylenediamine (e.g., tetramethylethylenediamine), optionally substituted 1,7-phenanthroline derivatives, optionally substituted 1,10-phenanthroline derivatives, optionally substituted 2,2'-bipyridine derivatives, and optionally substituted 4-dimethylaminopyridine derivatives.

The methods are fairly flexible with respect to substrates, and accommodate both those containing both aryl and heteroaryl moieties. Exemplary substrates comprising aryl moieties include those comprising optionally substituted benzene (including mesilylene and toluene), biphenyl, naphthalene, anthracene, or higher polyaromatic ring structures. These pure hydrocarbon substrates generally require more forcing conditions to silylate the ring carbons than do heteroaryl systems. See Example 6.4. Nevertheless, the ability to functionalize these hydrocarbon ring structures is an important feature of these methods and systems.

Where the aryl or heteroaryl moiety comprises an alpha-methyl or methylene C—H bond, as in an optionally substituted $C_{1-6}$ alkyl group (as exemplified by methyl groups of toluene, mesilylene, 1,2 dimethylindole, or 2,5-dimethylthiophene in the Examples), it appears that the reaction proceeds to form alpha silanes at temperatures lowered than required to silylate the ring carbons. As used herein, the term "alpha carbon" refers to the first carbon positioned exocyclic to the aromatic moiety, and "alpha" as in "alpha methyl or methylene" is intended to refer to the methyl or methylene on the first exocyclic carbon directly attached to the aromatic ring. The term "alpha silane" refers a silane bonded to the alpha carbon. The term "alpha" is considered to encompass benzylic carbons for 6 membered aryl aromatics. Methods resulting in such silylations are within the scope of the present invention.

Other exocyclic ring substituents, including those having an exocyclic aromatic C—X bond, generally react according to the methods described herein. The term "exocyclic" refers to the position of the O, N, or S with respect to the aromatic ring system. For example, the term "exocyclic" refers to a bond in which the carbon is contained within the aromatic rings system, but the respective oxygen, nitrogen, or sulfur atoms are not and, (in the case of nitrogen), vice versa. For example, phenol, dimethylaniline, 1-methyl-1H-pyrrole, and benzenethiol contain exocyclic aromatic C—O, C—N, and C—S bonds, respectively. Exemplary organic substrates comprise, but are not limited to, optionally substituted phenyl ethers, phenyl amines, phenyl sulfides, naphthyl ethers, naphthyl amines, or naphthyl sulfides moiety, N-alkyl or N-aryl pyrroles, or combinations thereof.

Where X is O or N, the reaction favors silylation of the ring ortho or at the carbon adjacent to the carbon containing the exocyclic C—X bond. Electron-rich systems or electron-donating groups or substituents appear to be generally more reactive than electron-poor systems or electron-withdrawing groups or substituents; the latter may require more forcing conditions than the former, but note that more forcing conditions derived from higher temperatures may result in driving the C—X cleavage manifold—see, for example co-filed U.S. patent application Ser. No. 14/043,917, filed Oct. 2, 2013, entitled "Transition-Metal-Free Reductive Cleavage of Aromatic C—O, C—N, and C—S Bonds by Activated Silanes." Anisole and 2-methoxynaphthalene show a particular preference to the ortho position, and this selectivity provides the basis for embodiments comprising the selective ortho silylation of such substrates. See, e.g., Examples 6.7.1 to 6.7.4.

Note that these compounds may be seen as surrogates for polymers or oligomers. For example, the demonstrated ability to silylate dimethoxybenzene, diphenyl ether, and 3-methoxynaphthalene provide enabling support for the ability to silylate polymers having linkages such as:

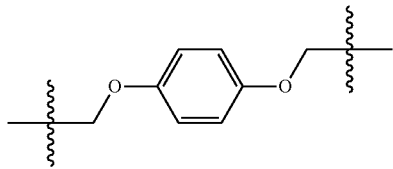

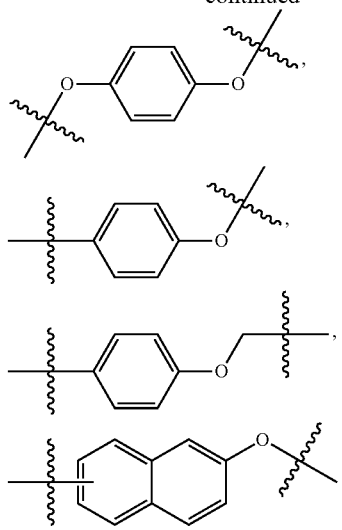

including such as polymers or copolymers of phenylene oxides, naphthalene oxides, or alkylenephenylene oxides, and methods to effect these transformations are considered within the scope of the present disclosure.

Interesting, and by contrast, those substrates having exocyclic aromatic C—X bond, where X is S-alkyl provides a different reactivity, showing a proclivity to silylate the alkyl group rather than the aromatic ring system. See, e.g., Example 6.7.5. This reactivity pattern provides a basis for those embodiments comprising the β-silylation of such substrates.

In certain embodiments, the methods are applied to an organic substrate comprising a heteroaryl moiety. Non-limiting heteroaryl moieties include those an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, dibenzothiophene. In more preferred embodiments, the substrate comprises a moiety comprising an optionally substituted furan, pyrrole, thiophene, pyrazole, imidazole, benzofuran, benzopyrrole, benzothiophene, azaindole dibenzofuran, xanthene, dibenzopyrrole, or dibenzothiophene moiety. Independent embodiments provide that the methods yield silylated products substituted as described herein.

In other specific embodiments, the methods are operable on substrates comprising the following moieties:

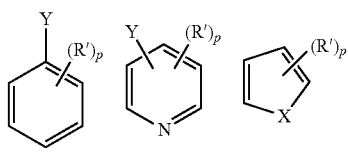

where X is N—R", O, or S;
Y is H, N(R")$_2$, O—R", or S—R"
p is 0 to 4, 0 to 3, 0 to 2, or 0 to 1;

R' is a functional group "Fn," as described above, or (R')$_p$ comprises a used alicyclic, heteroalicyclic (e.g., methylene, ethylene, or propylene linked diether), aryl or heteroaryl moiety; and R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Exemplary fused heterocyclic moieties include, for example, the groups:

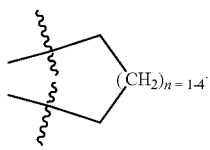

Ethylenedioxothiophene is but one example of such a heteroaryl diether.

In certain more specific embodiments, the methods are operable on organic substrates comprising the following moieties:

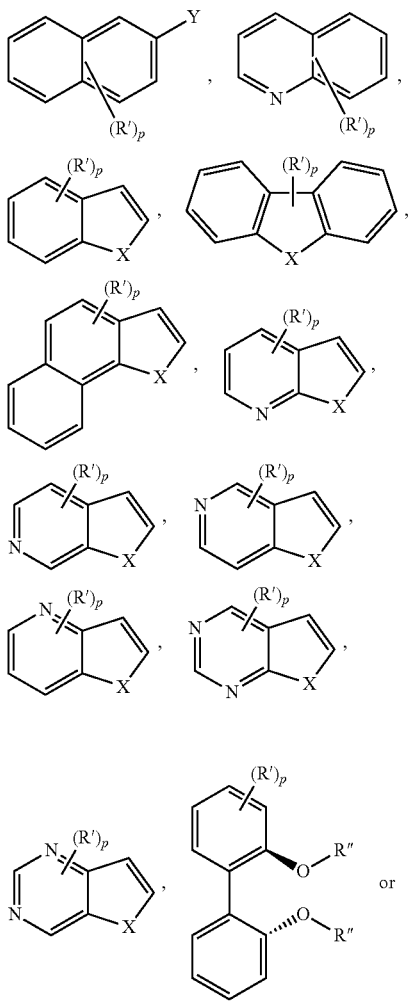

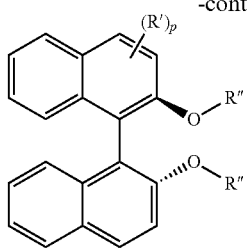

where X, Y, R', R" and p are as defined above. Note that the designation

in each case, is intended to allow for substitution on either aromatic ring.

Heteroaryl moieties appear to react according to the inventive methods under conditions that are milder than their aryl cogeners, such that, in mixed aryl-heteroaryl systems, reactions generally proceed to silylate the heteroaryl ring preferentially.

Also, 5-membered heteroaryl moieties appear to react according to the inventive methods under conditions that are milder than even 6-membered heteroaryl moieties. For example, as shown in Examples 6.9.26 to 9.9.29, 1H-pyrrolopyridines are shown to silylate preferentially in the 5-membered heterocylic portion of the molecule. And both rings silylate under conditions much milder than found for pyridine.

The silylation reactions with substrates comprising 5-membered heteroaryl moieties also provide remarkably clean and apparently tunable regioselectivities. Substrates comprising 5-membered heteroaryl rings containing O or N apparently can silylate at the C-2 or C-3 position, depending on time and temperature, but milder conditions appear to favor substitution at the C-2 position. While not intending to be bound by the correctness or incorrectness of any particular theory, it appears that silylation at the C-2 position represents the kinetic result of the reaction, whereas silylation at the C-3 position is thermodynamically favored. While described in terms of "kinetic" and "thermodynamic" pathways, it is not clear that silylation at a C-3 position necessarily proceeds through a C-2 intermediate. Indeed, experiments using 1,2 dimethyl indole and 2,5-dimethyl thiophene, where the C-2 positions are blocked by methyl groups, reaction proceeded to silylate the alpha-methyl group preferentially, with no evidence for silylation in the C-3 position.

Unless otherwise stated, reference to silylation at a specific position is intended to connote a regioselectivity or regiospecificity of a product at that position of greater than about 80%. But other embodiments provide that the regiospecificity at that position is greater than about 50%, greater than about 75%, greater than about 90%, or greater than about 95%.

The silylation reactions are also remarkably tolerant to a range of functional groups (see, e.g., Example 7.2). Carbonyl groups in general were not tolerated, but can be made compatible if protected as the corresponding acetal or ketal. Aryl-F, Aryl-Cl, Aryl-CF$_3$, epoxide, N-alkyl aziridine, cis- and trans-olefins, acetylene, pyridine, and tertiary amine and phosphine moieties are all compatible with the silylation chemistry. Even free OH and NH groups are tolerated to some extent, apparently owing to a fortuitous silylative protection of the heteroatom in situ. By contrast, the presence of Aryl-Br, Aryl-I, Aryl-CN, and Aryl-NO$_2$ all appear to shut down the reaction. This versatility is important for the application of the current method to, for example, alkaloid natural product synthesis and pharmaceutical science applications either at an early stage or for advanced intermediate functionalization.

Figure 4A:
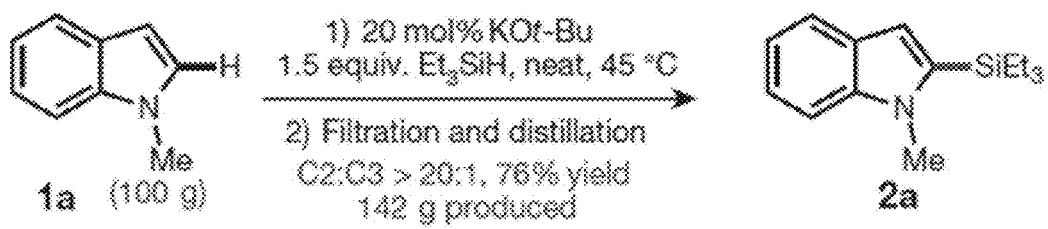
FIGS. 4A-4E show certain synthetic applications of the base-catalysed C—H silylation. In these examples, KO-t-Bu is used as an exemplary base.
Figure 4B:
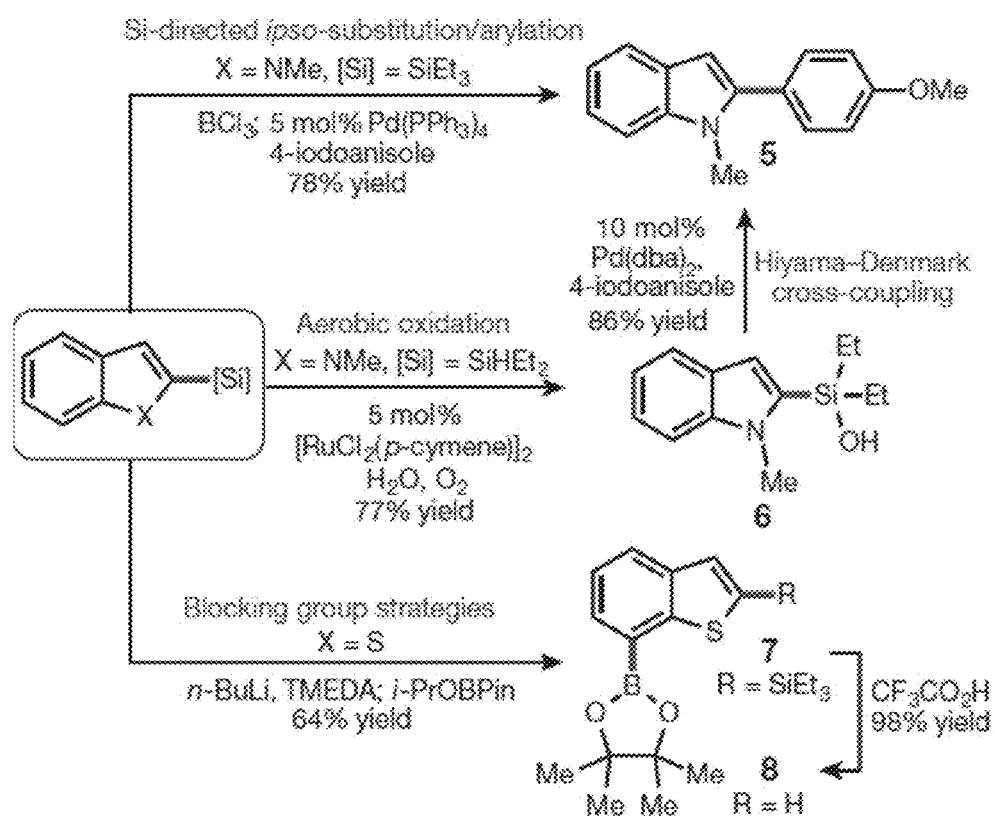

The products of the inventive methods are useful in a range of agrichemical, pharmaceutical, and electronics applications, as described infra. Heteroarylsilane derivatives, such as described herein, are known to undergo a variety of powerful synthetic transformations; a number of representative examples are demonstrated here (FIG. 4B). Again, each of these downstream transformations is accessible because of the present inventive processes, and so these downstream steps (when coupled with the inventive silylations) are considered within the scope of the present invention.

The use of aromatic silanes, such as those described herein, are useful synthons for the preparation of biaryl/biaromatic compounds, for example, using the Hiyama coupling methods generally recognized in the art. As understood by the skilled artisan, the term "biaromatic" refers to two independent aromatic/heteroaromatic ring systems joined by a single bond e.g., bifuran, biphenyl, bipyridine, bithiophene, phenyl-pyridine, etc. The skilled artisan would be well able to combine the teachings of these Hiyama coupling methods with those presented here, without undue experimentation, to prepare biaryl/biaromatic compounds, and such preparations are considered within the scope of the present invention. Also, Ball and colleagues (Ball et al., *Science* 28 Sep. 2012: Vol. 337 no. 6102 pp. 1644-1648, which is incorporated by reference herein for its teaching of the catalysts, methods, and substrates) have more recently described another method, using gold catalysts, to couple trialkyl silanes, such as those described herein, to form biaryl/biaromatic compounds. Again, the skilled artisan would be well able to combine the teachings of the Ball coupling, including at least the second aryl compounds taught or suggested in the Ball reference, again without undue experimentation, to prepare biaryl or biaromatic compounds, and such methods and preparations are considered within the scope of the present invention. In such embodiments, a silylated product of the present invention, whether isolated or generated in situ, is further reacted under conditions (including the presence of a suitable transition metal catalyst) sufficient to couple the silylated product with a second aromatic compound to prepare the biaryl or biaromatic product. As intended herein, the second aromatic compound comprises an optionally substituted aromatic moiety, including optionally substituted aryl and heteroaryl moieties, where the terms "optionally substituted," "aromatic," "aryl," and "heteroaryl" carry the same definitions as already described herein.

Such transformations are illustrated herein. For example, C2 Si-directed Suzuki-Miyaura cross-coupling by the method of Zhao and Snieckus, or Hiyama-Denmark cross-coupling via heteroarylsilanol 6, furnished 2-arylated indole. An unusual direct C7 functionalization of benzothiophene to give boronate esters 7 and 8 was achieved by using a blocking group strategy from silylated precursor 4h. See Examples 8.4.1 and 8.4.2. This general transformation (i.e., the use of the inventive silylation to protect/deprotect certain favorable positions) is considered within the scope of the present invention. Indeed, while Examples 8.4.1 and 8.4.2 show this in the context of the C2 position of indoles (and by extension, benzofurans, and thiophenes), the ability to regiospecifically place and then remove a silyl group is a valuable new tool in the chemist's arsenal.

The conversion of aromatic silanes, such as those described herein, are also known to be convertible to aromatic hydroxy compounds, using the well-known Fleming-Tamao oxidation methods. The skilled artisan would be well able to combine the teachings of these Fleming-Tamao oxidations with those presented here, again without undue experimentation, to prepare hydroxylated aromatic compounds, and such methods and preparations are considered within the scope of the present invention. In such embodiments, the aromatic silylated products of the present invention, whether isolated or generated in situ, are further reacted under conditions (including the presence of a suitable transition metal catalyst) sufficient to convert the silylated product to hydroxylated aromatic products. Once hydroxylated, the aromatic products can be converted to the corresponding alkyl or aryl ethers, alkyl or aryl esters, halides (chloro, bromo, fluoro, iodo), nitrates, nitrites, or other similar functional groups by conventional methods. Aryl or heteroaryl iodides are especially convenient precursors for a range of coupling reactions (see, e.g., the palladium/copper-catalyzed sila-Sonogashira reactions of such compounds with alkynylsilanes as described in Nishihara, et al., *Tetrahedron Letters*, 50 (2009) 4643-4646). All such transformations and products resulting therefrom are considered within the scope of the present invention (when conducted in conjunction with the inventive silylations)

Also, the ability of the present invention to provide silylate to provide alpha-carbon substituents (or β-silyl groups in the case of exocyclic sulfur) also provide that those products may be used as synthons for the Peterson olefination reaction. The known ease of deprotonating the alpha-methylene proton, when adjacent to the silane silicon (the "alpha silicon effect") to yield an alpha-silyl carbanion can form a convenient precursor for this olefination reaction. The skilled artisan would be well able to combine the teachings of these Peterson olefination reaction with those presented here, again without undue experimentation, to replace the alpha silyl groups with alpha olefins, and such methods and preparations are considered within the scope of the present invention. In such embodiments, the aromatic silylated products of the present invention, whether isolated or generated in situ, are further reacted under conditions sufficient (including the presence of a suitable transition metal catalyst) to convert the silylated product to aromatic alpha-olefin products.

Additional embodiments include those where the aromatic silylated products of the present invention, whether isolated or generated in situ, are further reacted under conditions sufficient (including the presence of a suitable transition metal catalyst) to convert an alpha silylated product to the corresponding carboxylic acid, using the methods described, for example, in Mita, et al., *Organic Letters*, 2012, Vol. 14, No. 13, 3462-3465. The skilled artisan would be well able to combine the teachings of these reactions with those presented here, again without undue experimentation, to prepare carboxylated aromatic compounds, and such methods and preparations are considered within the scope of the present invention.

Still further embodiments include those where the aromatic silylated products of the present invention, whether isolated or generated in situ, are further reacted under conditions sufficient (including the presence of a suitable transition metal catalyst) to convert the aromatic silylated product to boronic halides and esters, halides (including chloro, bromo, and iodo), and nitroso groups using the methods described, for example, in Zhao, et al., *Organic Letters*, 2005, Vol. 7, No. 13, 2523-2526. The skilled artisan would be well able to combine the teachings of these reactions with those presented here, again without undue experimentation, to prepare carboxylated aromatic compounds, and such methods and preparations are considered within the scope of the present invention. Also, as described in the Zhao reference, these aromatic silylated precursors, derived from the instant invention, can also be cross-coupled with aromatic halides using the Suzuki-Miyaura cross-coupling protocols described above, to arrive at biaromatic products.

The demonstrated ability to silylate substituted thiophenes and terthiophenes also provides for further reactions of these products with perfluoroarenes, to provide alternating thiophene-perfluoroarene copolymers, as described in Wang Y. and Watson M., *J. Amer. Chem. Soc.*, 2006, 128, 2536-2537. The skilled artisan would be well able to combine the teachings of Wang and Watson with those presented here, again without undue experimentation, to prepare transition-metal-free alternating thiophene-perfluoroarene copolymers, and such methods and the products derived therefrom are within the scope of the present invention.

Figure 4C:
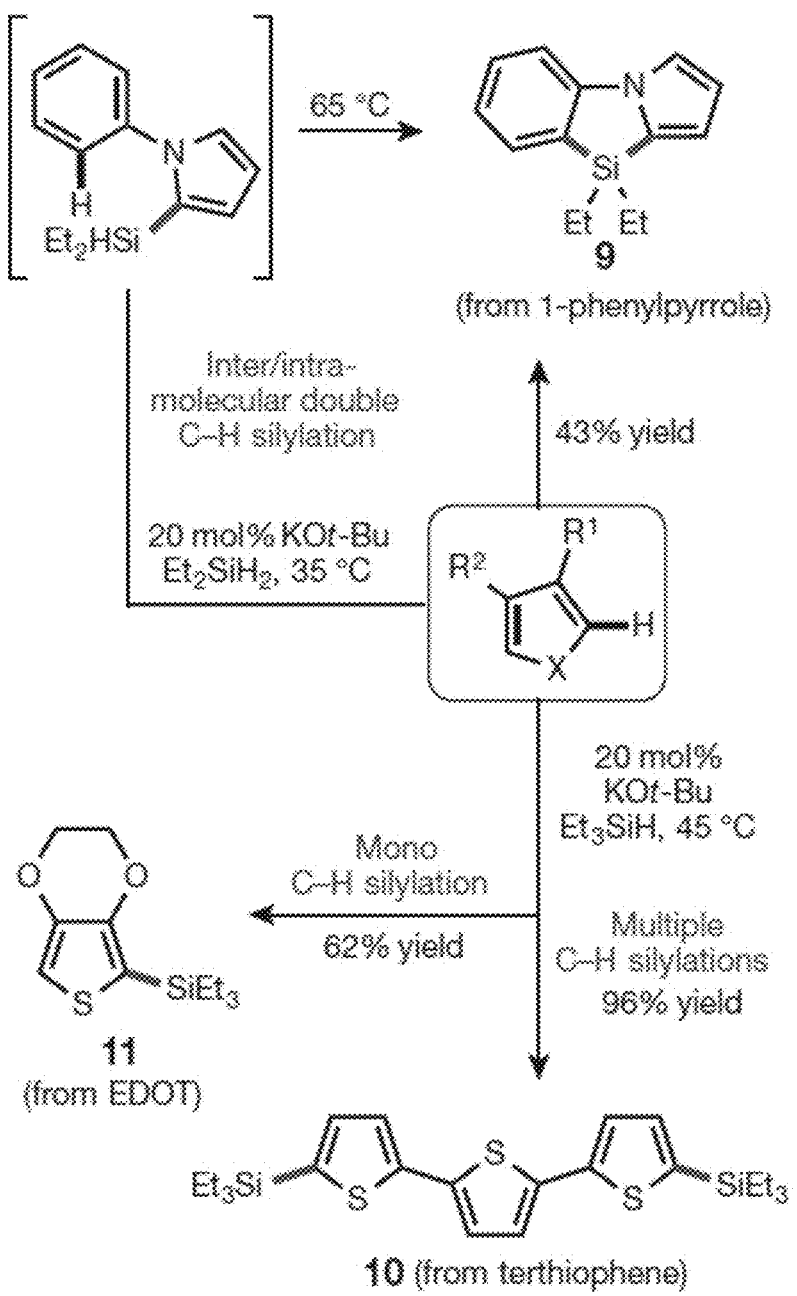

Organosilicon has been extensively investigated in the development of advanced materials owing to silicon's unique physical and chemical properties. Within this context, the present disclosure provides examples of compounds and transformations that are valuable in the materials and pharmaceutical context (see e.g., FIG. 4C and Example 8.8.1 to 8.8.5). In but one example, sila-heterocycle 9 was prepared in one step directly from the commercially available unfunctionalized heteroarene by an unprecedented double C—H functionalization involving intermolecular silylation followed by intramolecular silylation. A high-yielding bis-silylation of thiophene oligomer 10 furnished the starting material for an entirely transition-metal-free catalytic route to alternating copolymers. Finally, the monoselective silylation of the 3,4-ethylenedioxythiophenemonomer provided a potential strategy for the modification of polythiophene-derived materials (FIG. 4C, 11). The general ability to silylate thiophenes (including EDOT) and terthiophenes is one of the many important aspects of the present invention.

Figure 4D:
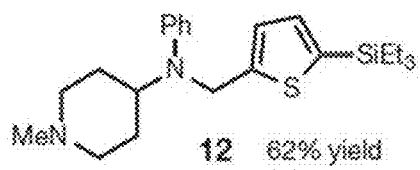
Figure 4D:
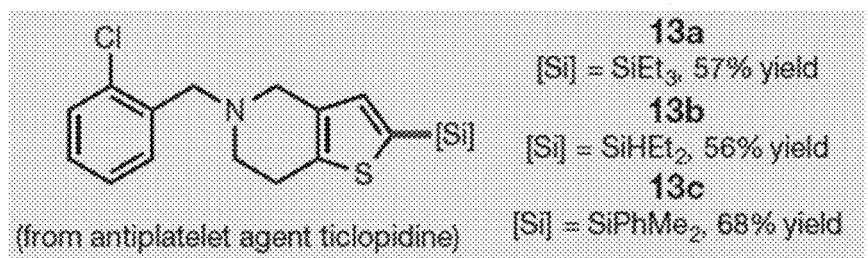
Figure 4D:
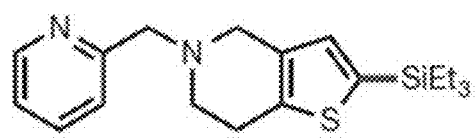
Figure 4E:
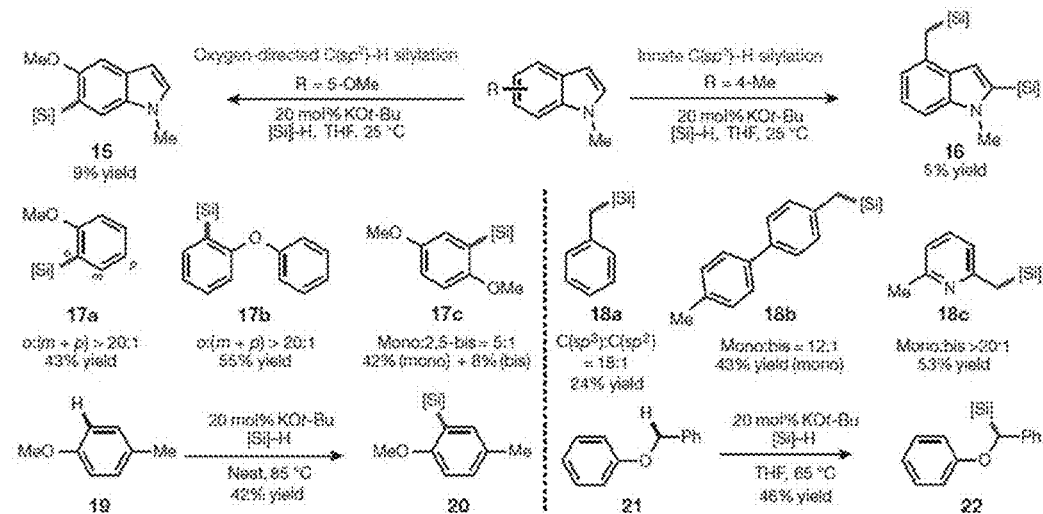

Sila-drug analogues have garnered much attention from medicinal chemists because they can offer improved stability, solubility and pharmacokinetic properties compared with the parent all-carbon compounds. Moreover, the installed organosilicon functionality can serve as a synthetic handle for subsequent elaboration, facilitating library synthesis and enabling structure activity relationship studies. As a result, organosilicon-containing small molecules are of growing interest in pharmaceutical science, and the direct silylation of lead compounds would thus represent a new and potentially powerful tool in drug discovery. To evaluate the present methods for such late-stage C—H functionalization applications, the antihistamine thenalidine and the antiplatelet drug ticlopidine was subjected to representative catalytic silylation conditions. The reactions proceeded smoothly in the case of both active pharmaceutical ingredients, yielding the Si-containing target compounds 12 and 13a-c in 56%-68% yield with excellent chemo- and regioselectivity (FIG. 4D). The piperidines, benzylic C—H bonds and aryl chloride moieties were all tolerated without any observed side reactions. Silylation of aza analogue 14 also proceeded well, demonstrating the compatibility of these methods with pyridine-containing complex molecules of potential pharmaceutical importance. Finally, during these investigations, minor amounts of $sp^2$ and $sp^3$ C—H silylation by-products at ambient temperature were observed in the cases of methoxy- and methyl-substituted indoles, respectively (that is, 15 and 16; FIG. 4E). Simple arenes react analogously. The ortho-silylation of anisole and the directing group-free $C(sp^3)$-H silylation of toluene were discovered, furnishing silylated derivatives 17a and 18a, respectively. Four additional examples were demonstrated, providing silylarenes (17b and 17c) and benzylsilanes (18b and 18e) with excellent selectivity. Of particular note is the $C(sp^3)$-H silylation of 2,6-lutidine, providing an example of C—H silylation in an electron-deficient system. Interestingly, methoxy toluene 19 and benzyl ether 21, both containing potentially reactive $sp^2$ and $sp^3$ C—H bonds, were silylated with opposite selectivities to yield 20 and 22. In the case of 22, the reaction introduces a Si-substituted chiral center.

The following listing of embodiments is intended to complement, rather than displace or supersede, the previous descriptions.

Embodiment 1

A chemical system for silylating an organic substrate comprising an aromatic moiety, said system comprising or consisting essentially of a mixture of (a) at least one organosilane and (b) at least one strong base, the definition of said strong base now also including hydroxide, especially KOH, said system preferably, but not necessarily, being substantially free of transition-metal compounds, the strong base being sufficient to effect the silylation of the organic moiety without transition metal catalyst, plasma, or UV radiation.

Embodiment 2

The system of Embodiment 1, wherein the transition-metal compound is present at less than 10 ppm, relative to the weight of the total system.

Embodiment 3

The chemical system of Embodiment 1 or 2, further comprising an optionally substituted tetraalkylethylenediamine tetramethylethylenediamine), an optionally substituted 1,7-phenanthroline derivative, an optionally substituted 1,10-phenanthroline derivative, an optionally substituted 2,2'-bipyridine derivatives, or an optionally substituted 4-dimethylaminopyridine derivative.

Embodiment 4

The system of any one of Embodiments 1 to 3, that is substantially free of water, oxygen, or both water and oxygen, preferably anaerobic and anhydrous.

Embodiment 5

The system of any one of Embodiments 1 to 4, wherein at least one organosilane comprises an organosilane of Formula (I) or Formula (II):

$(R)_{4-m}Si(H)_m$     (I)

$R-[-SiH(R)-O-]_n-R$     (II)

where: m is 1, 2, or 3; n is 10 to 100; and each R is independently optionally substituted $C_{1-12}$ alkyl or heteroalkyl, optionally substituted $C_{5-20}$ aryl or $C_{4-20}$ heteroaryl, optionally substituted $C_{6-30}$ alkaryl or heteroalkaryl, optionally substituted $C_{5-30}$ aralkyl or heteroaralkyl, optionally substituted —O—$C_{1-12}$ alkyl or heteroalkyl, optionally substituted —O—$C_{5-20}$ aryl or —O—$C_{4-20}$ heteroaryl, optionally substituted —O—$C_{5-30}$ alkaryl or heteroalkaryl, or optionally substituted —O—$C_{5-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl $C_1$-$C_{20}$ alkylsulfonyl, $C_5$-$C_{20}$ arylsulfonyl, alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 6

The system of Embodiment 5, wherein the organosilane is $(R)_3SiH$ or $(R)_2SiH_2$, where R is aryl, aralkyl, or $C_{1-6}$ alkyl.

Embodiment 7

The system of any one of Embodiments 1 to 6, wherein the at least one strong base comprises an alkali or alkaline metal hydride or alkoxide.

Embodiment 8

The system of any one of Embodiments 1 to 7, wherein the at least one strong base comprises an alkali or alkaline metal hydride.

Embodiment 9

The system of Embodiment 8, wherein the at least one strong base comprises calcium hydride or potassium hydride.

Embodiment 10

The system of any one of Embodiments 1 to 7, wherein the at least one strong base comprises an alkali or alkaline metal alkoxide.

Embodiment 11

The system of Embodiment 10, wherein the at least one alkoxide comprises a $C_{1-12}$ linear or branched alkyl moiety or a $C_{5-10}$ aromatic or heteroaromatic moiety.

Embodiment 12

The system of Embodiment 11, wherein the at least one alkoxide comprises methoxide, ethoxide, propoxide, butoxide, or 2-ethyl-hexyl alkoxide.

Embodiment 13

The system of any one of Embodiments 7 to 12, wherein the alkali or alkaline metal hydride or alkoxide base is a potassium or cesium alkoxide.

Embodiment 14

The system of any one of Embodiments 1 to 13, where the organosilane is triethylsilane and the strong base is potassium tert-butoxide.

Embodiment 15

The system of any one of Embodiments 1 to 7, wherein the at least one strong base comprises potassium hydroxide (KOH).

Embodiment 16

The system of any one of Embodiments 1 to 15, wherein the organosilane and the at least one strong base are present together at a molar ratio, with respect to one another, in a range of from about 20:1 to about 1:1.

Embodiment 17

The system of any one of Embodiments 1 to 15, further comprising an organic aromatic compound, said compound being a solvent, a substrate, or both a solvent and a substrate.

Embodiment 18

The system of Embodiment 17, wherein the organic compound comprises an optionally substituted benzene, biphenyl, naphthalene, or anthracene ring structure.

Embodiment 19

The system of Embodiment 17 or 18, wherein the organic aromatic compound comprises a heteroaryl moiety.

Embodiment 20

The system of Embodiment 19, wherein the organic aromatic compound comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 21

The system of Embodiment 19 or 20, wherein the organic aromatic compound comprises an optionally substituted furan, pyrrole, thiophene, pyrazole, imidazole, benzofuran, benzopyrrole, benzothiophene, indole, azaindole, dibenzofuran, xanthene, dibenzopyrrole, dibenzothiophene, or a hindered dibenzofuran, dibenzopyrrole, or dibenzothiophene moiety.

Embodiment 22

The system of any one of Embodiments 17 to 21, wherein the organic aromatic compound comprises at least one of the following moieties:

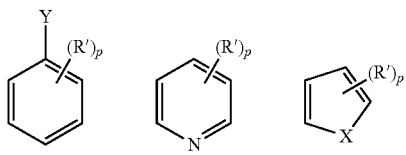

where X is N—R", O, or S;
Y is H, N(R")$_2$, O—R", or S—R"
p is 0 to 4, 0 to 3, 0 to 2, or 0 to 1;
R' is a functional group "Fn," as described above or (R')$_p$ comprises an optionally substituted fused alicyclic, heteroalicyclic (e.g., methylene, ethylene, or propylene linked diether), aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 23

The system of any one of Embodiments 17 to 22, wherein the substrate comprises at least one of the following moieties:

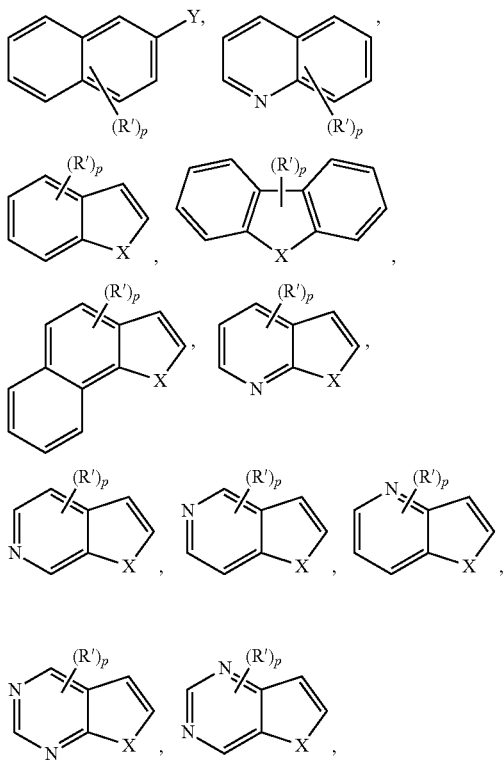

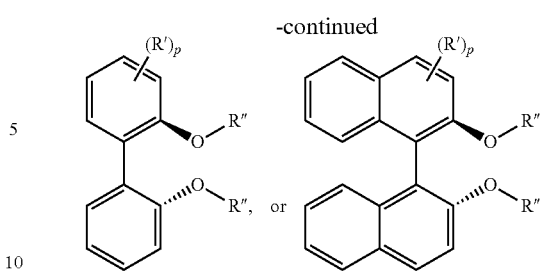

where X, Y, R', R" and p are as defined above. Note that the designation

in each case, is intended to allow for substitution on either aromatic ring.

Embodiment 24

The system of method of any one of Embodiments 17 to 22, wherein the aromatic organic compound comprises at least one alpha-methyl or methylene C—H bond, said method resulting in the formation of a alpha silane.

Embodiment 25

A method of silylating a substrate comprising an aromatic moiety, said method comprising contacting a quantity of the organic substrate with a system of any one of Embodiments 1 to 24.

Embodiment 26

A method comprising contacting an organic substrate comprising an aromatic moiety with a mixture comprising or consisting essentially of (a) at least one organosilane and (b) at least one strong base, the definition of said strong base now also including hydroxide, especially KOH, under conditions sufficient to silylate the substrate; wherein said mixture and substrate are preferably, but not necessarily, substantially free of transition-metal compounds.

Embodiment 27

The method of Embodiment 26, wherein the transition-metal compound is present at less than 10 ppm, relative to the weight of the total system.

Embodiment 28

The method of Embodiments 26 or 27, wherein the mixture further comprises an optionally substituted tetraalkylethylenediamine (e.g., tetramethylethylenediamine), an optionally substituted 1,7-phenanthroline derivative, an optionally substituted 1,10-phenanthroline derivative, an optionally substituted 2,2'-bipyridine derivatives, or an optionally substituted 4-dimethylaminopyridine derivative.

Embodiment 29

The method of any one of Embodiments 26 to 28, that is substantially free of water, oxygen, or both water and oxygen.

Embodiment 30

The method of any one of Embodiments 26 to 29, wherein at least one organosilane comprises an organosilane of Formula (I) or Formula (II):

$$(R)_{4-m}Si(H)_m \quad (I)$$

$$R\text{—}[\text{—}SiH(R)\text{—}O\text{—}]_n\text{—}R \quad (II)$$

where m is 1, 2, or 3 (preferably 1 or 2);
n is 10 to 100; and
and each R is independently optionally substituted $C_{1-12}$ alkyl or heteroalkyl, optionally substituted $C_{5-20}$ aryl or $C_{4-20}$ heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or $C_{4-20}$ heteroaryl, optionally substituted —O—$C_{6-30}$ alkaryl or —O—$C_{4-30}$ heteroalkaryl, or optionally substituted —O—$C_{6-30}$ aralkyl or —O—$C_{4-30}$ heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 31

The method of any one of Embodiments 26 to 30, wherein the organosilane is $(R)_3SiH$, where R is independently $C_{1-6}$ alkyl.

Embodiment 32

The method of any one of Embodiments 26 to 31, wherein the at least one strong base comprises an alkali or alkaline metal hydride or alkoxide.

Embodiment 33

The method of any one of Embodiments 26 to 32, wherein the at least one strong base comprises an alkali or alkaline metal hydride.

Embodiment 34

The method of Embodiment 33, wherein the at least one strong base comprises calcium hydride or potassium hydride.

Embodiment 35

The method of any one of Embodiments 26 to 34, wherein the at least one strong base comprises an alkali or alkaline metal alkoxide.

Embodiment 36

The method of Embodiment 35, wherein the at least one alkoxide comprises a $C_{1-12}$ linear or branched alkyl moiety or a $C_{5-10}$ aryl or $C_{4-10}$ heteroaryl moiety.

Embodiment 37

The method of Embodiment 36, wherein the at least one alkoxide comprises methoxide, ethoxide, propoxide, butoxide, or 2-ethyl-hexyl alkoxide.

Embodiment 38

The method of any one of Embodiments 32 to 37, wherein the alkali or alkaline metal hydride or alkoxide is a potassium or cesium alkoxide.

Embodiment 39

The method of any one of Embodiments 26 to 38, where the organosilane is triethylsilane and the strong base is potassium tert-butoxide.

Embodiment 40

The method of Embodiment 26, where the organosilane is triethylsilane and the strong base is potassium hydroxide.

Embodiment 41

The method of any one of Embodiments 26 to 29, wherein the organosilane and the at least one strong base, the definition of strong base now including hydroxide, especially KOH, are present together at a molar ratio, with respect to one another, in a range of from about 20:1 to about 1:1.

Embodiment 42

The method of any one of Embodiments 26 to 41, wherein the at least one strong base, the definition of strong base now including hydroxide, especially KOH, and substrate are present together at a molar ratio, with respect to one another, in a range of from about 0.01:1 to about 5:1 preferably in a range of from about 0.01:1 to about 0.9:1.

Embodiment 43

The method of any one of Embodiments 26 to 42, wherein the organic substrate comprises an optionally substituted benzene, biphenyl, naphthalene, or anthracene ring structure.

Embodiment 44

The method of any one of Embodiments 26 to 43, wherein the organic substrate comprises an exocyclic aromatic C—X bond, where X is N, O, or S.

Embodiment 45

The method of any one of Embodiments 26 to 44, wherein the organic substrate comprises an exocyclic aromatic C—X bond and the silylation occurs ortho to the exocyclic C—X bond, where X is N, O, or S.

Embodiment 46

The method of any one of Embodiments 26 to 45, wherein the organic substrate comprises a heteroaryl moiety.

Embodiment 47

The method of any one of Embodiments 26 to 46, wherein the substrate comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 48

The method of any one of Embodiments 26 to 47, wherein the substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, or a dibenzothiophene.

Embodiment 49

The method of any one of Embodiments 26 to 48, wherein the organic aromatic substrate comprises at least one of the following moieties:

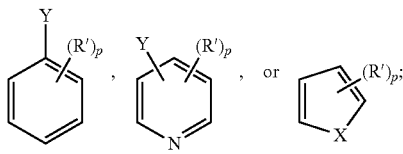

where X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 50

The method of any one of Embodiments 26 to 48, wherein the substrate comprises at least one of the following moieties:

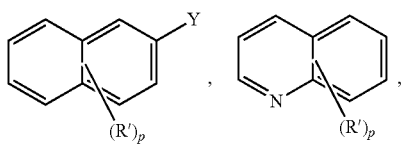

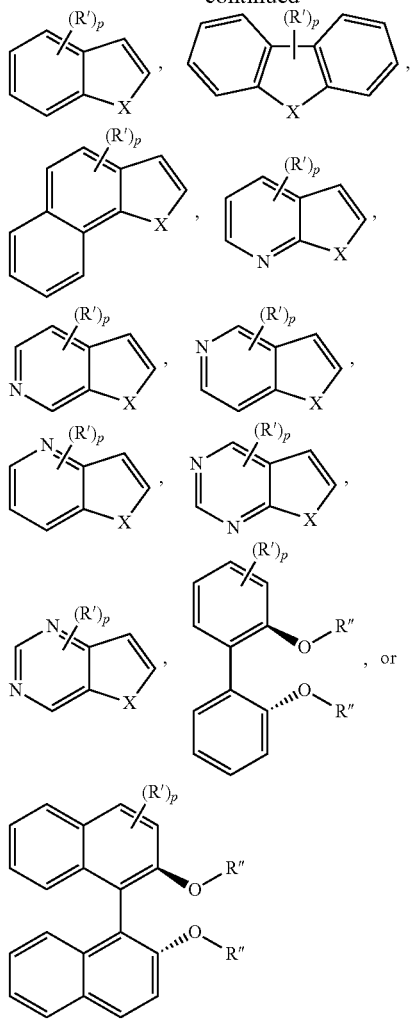

where X, Y, R', R" and p are as defined above. Note that the designation

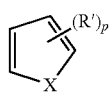

in each case, is intended to allow for substitution on either aromatic ring.

Embodiment 51

The method of any one of Embodiments 26 to 50, wherein the organic substrate comprises a heteroaryl moiety of structure:

and the silylation occurs at the C-2 position of the heteroaryl ring.

Embodiment 52

The method of any one of Embodiments 26 to 51, wherein the organic substrate comprises a heteroaryl moiety of structure:

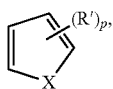

and the silylation occurs at the C-3 position of the heteroaryl ring.

Embodiment 53

The method of any one of Embodiments 26 to 52, wherein the aromatic substrate comprises at least one alpha-methyl or methylene C—H bond, said method resulting in the formation of a alpha silane.

Embodiment 54

The method of any one of Embodiments 26 to 53, wherein the aromatic substrate is polymeric or a polymeric precursor.

Embodiment 55

The method of any one of Embodiments 26 to 54, wherein the aromatic silylated product is further reacted under conditions sufficient to couple the silylated product with a second aromatic compound to prepare a biaromatic product.

Embodiment 56

The method of any one of Embodiments 26 to 54, wherein the aromatic silylated product is further reacted under conditions sufficient to convert the silylated product to an aromatic hydroxylated (protected or free hydroxyl), alkoxylated (or aryloxylated), or alkyl or aryl carboxylated product.

Embodiment 57

The method of any one of Embodiments 26 to 54, wherein the aromatic silylated product is further reacted under conditions sufficient to convert the silylated product to an aromatic alpha-olefin product.

Embodiment 58

The method of any one of Embodiments 26 to 54, wherein the aromatic silylated product is further reacted under conditions sufficient to convert the silylated product to an aromatic halide (chloro, bromo, fluoro, iodo), nitrate, or nitrite.

Embodiment 59

The method of any one of Embodiments 26 to 54, wherein the aromatic silylated product is further reacted under conditions sufficient to convert the silylated product to an aromatic alpha carboxylic acid or carboxylic acid alkyl or aryl ester.

Embodiment 60

The method of any one of Embodiments 26 to 54, wherein the aromatic silylated product is further reacted under conditions sufficient to convert the silylated product to an aromatic boronic halide or boronic ester.

Embodiment 61

The method of any one of Embodiments 26 to 54, wherein the silylated thiophene product is further reacted under conditions sufficient to convert the silylated product to an alternating thiophene-perfluoroarene copolymer.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: General Information

All reactions were carried out in dry glassware (e.g., oven- or flame-dried) under an argon atmosphere using standard Schlenk line techniques or in a Vacuum Atmospheres Glovebox under a nitrogen atmosphere unless specified otherwise.

Solvents were dried by passage through an activated alumina column under argon. Reaction progress was monitored by thin-layer chromatography (TLC), UHPLC-LCMS or GC-FID analyses. TLC was performed using E. Merck silica gel 60 F254 precoated glass plates (0.25 mm) and visualized by UV fluorescence quenching, phosphomolybdic acid, or $KMnO_4$ staining. Silicycle SiliaFlash P60 Academic Silica gel (particle size 40-63 nm) was used for flash chromatography.

Mesitylene (puriss., ≥99.0% (GC)) was refluxed over sodium/benzophenone, then distilled. Tetrahydrofuran was purified by passage through a solvent purification column then further distilled over sodium-potassium alloy and degassed with argon. All other solvents were purified by passage through solvent purification columns and further degassed with argon. NMR solvents for air-sensitive experiments were dried over $CaH_2$ and vacuum transferred or distilled into a dry Schlenk flask and subsequently degassed with argon. Triethylsilane (99%) was purchased from Sigma-Aldrich, refluxed over molecular sieves, and then distilled. It was then degassed by three freeze-pump-thaw cycles prior to use and subsequently passed through neutral alumina. Deuterotriethylsilane (97 atom % D) was purchased from Sigma-Aldrich and degassed by three freeze-pump-thaw cycles prior to use and other commercially available liquid reagents were treated analogously. Phenyldimethylsilane (≥98%), ethyldimethylsilane (98%) and diethylsilane (99%) were purchased from Sigma-Aldrich and distilled over $CaH_2$ and degassed by three freeze-pump-thaw cycles prior to use. Other commercially available liquid reagents were treated analogously. 1-methylindole (≥97%), benzofuran (99%), thianaphthene (98%), 1-methoxynaphthalene (≥98%), anisole (99%) and thioanisole (99%) were purchased from Sigma-Aldrich and were distilled prior to use. 2-methoxynaphthalene was recrystallized twice from boiling $Et_2O$. 1-phenylpyrrole (99%) was dissolved in Et₂O and passed through activated alumina. The ether was removed in racuo and the solid residue was recrystallized twice from a 3:1 mixture of absolute EtOH/water. 1-phenyl pyrrole (99%), diphenyl ether (≥99%), dibenzothiophene (≥99%) were purchased from Sigma-Aldrich and used as received. 4-methoxypyridine (97%) and 2,6-dimethoxypyridine (98%) were purchased from Sigma-Aldrich, passed several times through neutral, activated alumina and subjected to 3 freeze-pump-thaw cycles prior to use 1-methyl-7-azaindole was prepared following the procedure of Cheve, G. et al., *Medchemcomm* 2012, 3, 788. Sublimed grade KOt-Bu (99.99%) was purchased from Sigma-Aldrich and subjected to vacuum sublimation (30 mTorr, 160° C.) prior to use. Di-4-(methyl)phenyl ether, 1-naphthol, 2-naphthol, 4-tert-butylanisole, 4-methylanisole, 1,3-diphenoxybenzene, 2-methoxynaphthalene, and 1.0M tetrabutylammonium fluoride THF solution were purchased from Sigma-Aldrich and used as received. 4-(Methoxy)dibenzofuran, di-4-(tert-butyl)phenyl ether, naphthyl ethers, 4-(phenyl)phenyl phenyl ether, 2-ethoxynaphthalene, 2-Neopentyloxynaphthalene, 2-tert-butyloxynaphthalene were synthesized according to the literature procedures.

Heteroaromatic substrates were purchased from Aldrich, TCI, or Acros, or synthesized according to literature procedures, for example (a) Kong, A.; Han, X.; Lu, X. *Org. Lett.* 2006, 8, 1339. (b) Islam, S.; Larrosa, I. *Chem.—Eur. J.* 2013, 19, 15093. (c) Huestis, M, P.; Fagnou, K. *Org. Lett.* 2009, 11, 1357. (d) Mahadevan, I.; Rasmussen, M. *Tetrahedron,* 1993, 49, 7337. Additionally, the following compounds were synthesized and have been reported previously in U.S. Pat. No. 9,000,167: 4-(Triethylsilyl)dibenzofuran (3); 4,6-Bis(triethylsilyl)dibenzofuran (4); 3-(Triethylsilyl)biphenyl-2-ol (5); (3'-Triethylsilyl)biphenyl-2-ol (6); 3,3'-Bis(triethylsilyl)biphenyl-2-ol (7); o-Triethylsilyldiphenyl ether Standard NMR spectroscopy experiments were conducted on a Varian Mercury (¹H, 300 MHz) spectrometer, a Varian Inova 400 MHz spectrometer, a Varian 500 MHz spectrometer equipped with an AutoX probe, or a Varian 600 MHz spectrometer equipped with a Triax Probe. Chemical shifts are reported in ppm downfield from Me₄Si by using the residual solvent peak as an internal standard. Spectra were analyzed and processed using MestReNova Ver. 7. IR spectra were obtained on a Perkin Elmer Spectrum BXII spectrometer using thin films deposited on NaCl plates and reported in frequency of absorption (cm⁻¹). UHPLC-LCMS analyses were obtained on an Agilent 1290 ultra high performance liquid chromatography/mass spectrometry equipped with an Agilent EclipsePlus C18 RRHD 1.8 μM column. GC-FID analyses were obtained on an Agilent 6890N as chromatograph equipped with a HP-5 (5%-phenyl)-methylpolysiloxane capillary column (Agilent). GC-MS analyses were obtained on an Agilent 6850 gas chromatograph equipped with a HP-5 (5%-phenyl)-methylpolysiloxane capillary column (Agilent). High-resolution mass spectra (EI and FAB) were acquired by the California Institute of Technology Mass Spectrometry Facility. EPR spectra were recorded on a Bruker EMS spectrometer.

Example 2: Evaluation of Basic Activators

Throughout this specification, N-methyl indole is shown to act as an excellent exemplar of the reactivities associated with this inventive chemistry. The effects of various bases were evaluated under the following nominal conditions, with the results provided in Table 1:

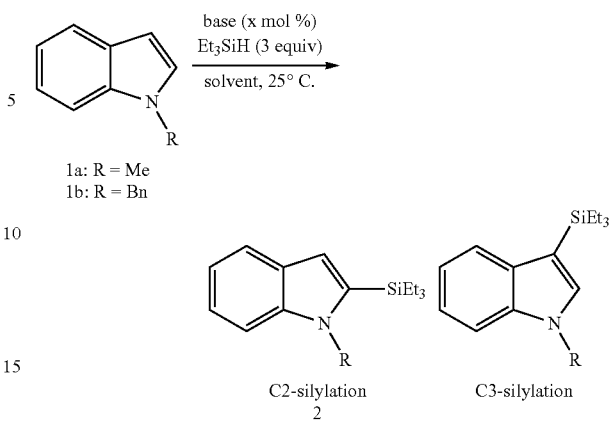

1a: R = Me
1b: R = Bn

C2-silylation
2

C3-silylation

TABLE 1

Effect of bases on the silylation of N-methyl indole at ambient conditions

| Entry[a] | R | Base | Solvent | x | t (hr) | C2:C3[b] | C2 (%)[b] |
|---|---|---|---|---|---|---|---|
| 1 | Me | LiOt-Bu | THF | 100 | 16 | — | 0 |
| 2 | Me | NaOt-Bu | THF | 100 | 16 | — | 0 |
| 3 | Me | NaOET | THF | 100 | 16 | — | 0 |
| 4 | Me | NAOAc | THF | 100 | 16 | — | 0 |
| 5 | Me | KOMw | THF | 100 | 16 | — | <5 |
| 6 | Me | KOEt | THF | 100 | 16 | — | 14 |
| 7 | Me | KOt-Bu | THF | 100 | 16 | >20:1 | 67 |
| 8 | Me | KHMDS | THF | 100 | 16 | >20:1 | 44 |
| 9 | Me | KOAc | THF | 100 | 16 | — | 0 |
| 10 | Me | KH | THF | 100 | 72 | — | 0 |
| 11 | Me | KOH | THF | 100 | 16 | — | 0 |
| 12 | Me | Cs₂CO₃ | THF | 100 | 16 | — | 0 |
| 13 | Me | DABCO | THF | 100 | 16 | — | 0 |
| 14 | Me | TBAF | THF | 100 | 16 | — | 0 |
| 15 | Me | CsF | THF | 100 | 16 | — | 0 |
| 16 | Me | KF | THF | 100 | 16 | — | 0 |
| 17[c] | Me | KOt-Bu | THF | 20 | 60 | 4:1 | 98 |
| 18[c] | Me | KOt-Bu | MeOt-Bu | 20 | 60 | >20:1 | 89 |
| 19[c] | Me | KOt-Bu | DME | 20 | 60 | 3.4:1 | 95 |
| 20[c] | Me | KOt-Bu | Neat | 20 | 48 | >20:1 | 88 |
| 21[d] | Me | KHMDS | THF | 20 | 72 | 17:1 | 75 |
| 22[c,e] | Bn | KOt-Bu | THF | 20 | 61 | >20:1 | 90 |
| 23[c,e,f] | Bn | KOt-Bu | THF | 20 | 96 | >20:1 | 22 |
| 24[c,e] | Bn | KOTMS | THF | 20 | 72 | >20:1 | 79 |

[a]Reactions performed with 0.2 mmol of 1 and 0.6 mmol of Et₃SiH in 0.2 mL of solvent.
[b]Determined by GC analysis of the crude reaction mixture using an internal standard.
[c]At 45° C.
[d]At 35° C.
[e]The ratio of C2:C3 and yield were determined by ¹H NMR analysis of the crude reaction mixture.
[f]With 50 mol % of 18-crown-6.

The results from Table 1 reveal that good catalysts for the C—H silylation reaction are categorized by the combination of a bulky basic anion and a potassium cation: KOt-Bu proved to be ideal catalyst and operated under neat conditions or in THF and MeOt-Bu (Entry 18, 20 and 22), but KHMDS (Entry 21) and KOTMS (Entry 24) were also effective. The complete lack of reactivity with LiOt-Bu and NaOt-Bu (Entries 1 and 2) as well as the precipitous drop in reactivity when 18-crown-6 is added to KOt-Bu (Entry 23) lend support to the crucial, albeit unknown, role of the potassium cation. Conversion roughly correlates with basicity in stoichiometric reactions (i.e., Ot-Bu>OEt>OMe; Entries 5-7). No product was observed in the absence of catalyst, or when KH, KOH, KOAc and Cs₂CO₃ were employed (Entries 9-12), under these conditions. Note that the previous finding that KOH was unreactive in these reactions has now been confirmed, but by altering the reaction conditions, it is now possible to realize these transformations with this catalyst (see Example 9 for KOH). The organic base DABCO and common fluoride-based activators for silicon—TBAF, CsF, and KF—were also investigated and failed to convert the starting material (Entries 13-16). Headspace GCTCD analysis of successful silylation reactions indicated the formation of $H_2$ Interestingly, other potential chelants did not inhibit, and in many cases, improved both yield and selectivity of the systems. This effect is not well understood. Without being bound by the correctness of this or any other theory, it is possible that these ligands chelated the potassium cation is proposed. Bipyridine-based ligand scaffolds as well as TMEDA (not shown) were demonstrated to be most effective in promoting high selectivity and efficiency in the silylation reaction. This is supported by the reaction with 1,7-phenanthroline, which is unable to chelate potassium, giving a lower product yield.

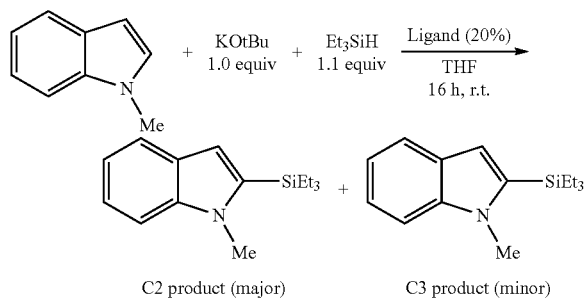

C2 product (major)   C3 product (minor)

TABLE 2

Effect of bases on the silylation of N-methyl indole at ambient conditions

| Ligand | Yield C2 | Selectivity |
| --- | --- | --- |
| 1,10-phenanthroline | 20.7 | >95% |
| 1,7-phenanthroline | 11.4 | >95% |
| bathophenanthroline | 33.7 | >95% |
| bipyridine | 64.8 | >95% |
| 4,4'-di-t-Bu bipyridine | 60 | >95% |

Yields and selectivities calculated using GC-FID analysis with mesitylene added as a standard for quantification. C2 selectivity defined as yield (C2 product/yield C2 + C3 products) × 100%.

The activity of the inventive systems and methods were remarkably tolerant of different base loadings. In the N-methyl indole model system, for example, decreasing base loading only mildly decreased efficiency. Remarkably, KOtBu even down to 1 mol % was effective and gave the major C2 product in 65% yield and a corresponding 89% C2 selectivity. This loading is even lower or equal to that required for the state-of-the-art transition-metal-based aromatic C—H silylation systems.

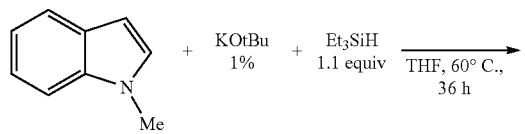

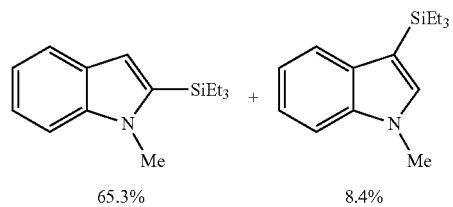

65.3%   8.4%

Example 3: Control Experiments and Trace Metal Analyses

Example 3.1: Control Reactions with Commercially Available KOt-Bu, Re-Sublimed KOt-Bu, and Freshly-Prepared KOt-Bu Three reactions were performed in parallel (THF, 45° C., 1-methylindole, 20 mol % KOt-Bu, 0.2 mmol scale): a) KOt-Bu (Aldrich, sublimed grade, 99.99%, trace metal basis) was used as received; b) KOt-Bu (Aldrich, sublimed grade, 99.99% trace metal basis) was used after re-sublimation by heating the material under vacuum; and c) KOt-Bu, freshly prepared by reaction of potassium metal with anhydrous t-BuOH followed by evaporation of the t-BuOH and sublimation of the solid, was used. No appreciable differences in conversion and selectivity in these reactions were observed.

Example 3.2: Control Reaction with KOt-Bu of Different Grade Purchased from Different Vendors Four reactions were performed in parallel (THF, 45° C., 1-benzylindole, 20 mol % KOt-Bu, 0.2 mmol scale): a) KOt-Bu (Aldrich, sublimed grade, 99.99% trace metal basis), b) KOt-Bu (Strem, 98%), c) KOt-Bu (TCI, >97%), and d) KOt-Bu (Alfa-Aesar, 97%). The reactions were monitored by UHPLC-LCMS. The conversion to product was greater than 90% complete after 90 hrs, and no appreciable differences in conversion and selectivity in these four reactions was observed.

Example 3.3

500 mg samples each of KOt-Bu from the four different vendors (Strem, Aldrich, TCI, Alfa-Aesar), 1-benzylindole, $Et_3SiH$, THF, and a standard reaction mixture (0.5 mmol scale mixture, prepared following the general procedure with 103.5 mg of 1-Bn-indole, 11.2 mg of KOt-Bu from Aldrich, 173.5 mg of $Et_3SiH$ in 0.5 mL of THF and stirred in the glovebox for 72 h.) were analyzed. Each sample was added to a 50 mL DigiTUBE digestion tube (SCP Science) followed by addition of 3.0 mL of Plasma Pure nitric acid (SCP Science) and heating to 75° C. for 36 hours. After digestion, each sample was diluted using Milli Q water to 50 mL and sample analysis was performed on an Agilent 7900 ICP-MS spectrometer. LOD indicates that the analyte concentration is below the instrument's Lowest Limit of Detection. Values in ppb (microgram per liter).

TABLE 3

| | ICPMS Trace Metal Analysis - Agilent 7900 (quantities in ppb) | | | | | | | |
|---|---|---|---|---|---|---|---|---|
| Element | KOt-Bu Strem (98%) | KOt-Bu TCI (>97%) | KOt-Bu Alpha (97%) | KOt-Bu Aldrich (99.99%) | THF | HSiEt$_3$ | 1-Bn-indole | Rxn Mixture |
| Ti | 0.360 | 0.051 | 0.138 | 0.464 | LOD | 2.073 | 9.408 | 31.082 |
| Mn | 1.343 | 1.168 | 1.338 | 1.525 | LOD | 0.177 | 88.191 | LOD |
| Fe | 12.285 | 10.171 | 13.080 | 14.036 | 1.691 | 9.531 | 86.191 | LOD |
| Co | 0.005 | LOD | 0.006 | 0.008 | 0.001 | 0.006 | 0.416 | LOD |
| Ni | 0.064 | LOD | 0.232 | 1.418 | 0.011 | LOD | 16.540 | 19.826 |
| Cu | 0.134 | 0.211 | 1.126 | 0.366 | LOD | 0.520 | 17.936 | 3.092 |
| Zr | 0.038 | LOD | LOD | 0.633 | LOD | 0.031 | LOD | 8.889 |
| Mo | 2.005 | 1.650 | 1.744 | 2.243 | LOD | LOD | LOD | LOD |
| Ru | 0.002 | 0.002 | 0.001 | 0.008 | LOD | 0.004 | 0.146 | LOD |
| Rh | LOD | LOD | LOD | 0.001 | LOD | LOD | LOD | LOD |
| Pd | 0.014 | 0.006 | 0.029 | 0.116 | 0.002 | 0.004 | 0.070 | 0.593 |
| Ag | 0.001 | LOD | 0.290 | 0.015 | LOD | 0.004 | 0.055 | 0.013 |
| Os | 0.001 | LOD | LOD | 0.001 | LOD | LOD | 0.007 | 0.016 |
| Ir | 0.001 | 0.001 | 0.002 | 0.026 | LOD | 0.001 | 0.047 | 0.041 |
| Pt | 0.009 | 0.004 | 0.002 | 0.010 | LOD | 0.001 | LOD | LOD |
| Au | 0.017 | 0.013 | 0.013 | 0.023 | 0.108 | 0.024 | 0.738 | 1.582 |

Example 4: Investigation into the Radical Nature of the KOt-Bu-Catalyzed C—H Silylation A number of experiments were conducted to gain insight into the reaction mechanism. As a first investigation, the reaction was performed in the presence of the radical traps TEMPO and galvinoxyl. Under conditions otherwise conducive to silylation of N-methyl indole, both additives thwarted the C—H silylation.

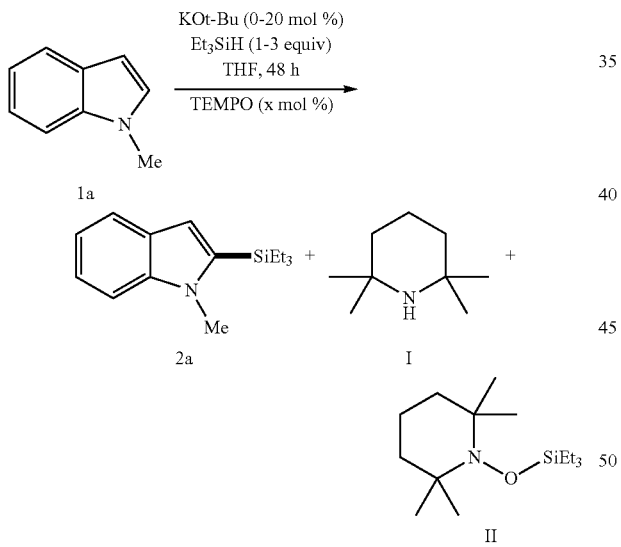

In a second set of experiments, three control experiments in an attempt to probe the role of TEMPO. A trace amount of triethylsilyl protected product II was observed at 23° C. with 1 equivalent of TEMPO, presumably arising from the radical combination of a silyl radical and TEMPO itself. Product II became the major component of the mixture when the temperature was raised to 65° C., lending support to the involvement of silyl radical species in the silylation reaction. In contrast, this protected compound II is not observed in the absence of KOt-Bu, indicating that the catalyst is critical to generate the silyl radical.

To evaluate the possible contribution of a polar mechanism (i.e., formation of silyl anions), experiments were conducted on the KOtBu-catalyzed reaction with benzothiophene 3h as a substrate in the presence of cyclohexene oxide as an additive (epoxides, including cyclohexene oxide, are known to undergo nucleophilic ring opening by silyl anions). However, under standard ambient conditions used in the test, the epoxide was quantitatively recovered after the reaction, and the desired silylation product 4h was obtained in moderate yield, providing evidence against the formation of discrete silyl anions.

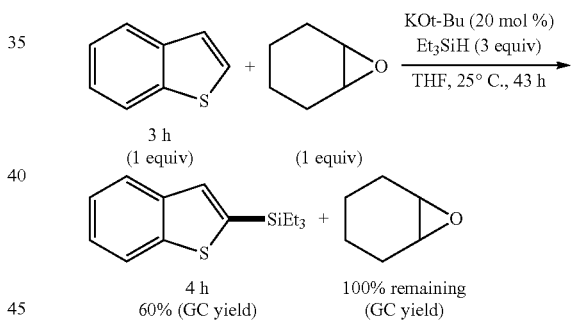

Example 5: General Procedure

In a nitrogen-filled glovebox, a 2 dram scintillation vial or 4 mL screw cap vial was loaded with the corresponding substrate (0.1-0.5 mmol, 1 equiv.), base (e.g., KOt-Bu or KOH, 0.1-5 equiv.) and a magnetic stirring bar, followed by syringe addition of the solvent (1 mL) and silane (1-5 equiv. filtered through a short pad of activated alumina before use). The reaction vial was sealed with and the mixture was stirred at the indicated temperature for the indicated time. The vial was removed from the glove box, the reaction mixture was diluted with diethyl ether (2 mL) and concentrated under reduced pressure. The regioselectivity (C2 silylation product to C3 silylation product: C2:C3) was determined by $^1$H NMR or GC analysis of the crude mixture. The residue was purified by silica gel flash chromatography to give the desired product.

Unless stated otherwise, in preparative experiments only products with the overall yield exceeding 2% were isolated and characterized. In the case of naphthyl alkyl ethers, a different workup procedure was used. After cooling, the reaction was diluted with dichloromethane (5 mL) and carefully quenched with 2 mL of 1 N aqueous HCl. Tridecane was added, and the mixture was transferred to a separatory funnel. The organic phase was separated, and the aqueous layer was extracted with dichloromethane (3 mL). The combined organic layers were dried over anhydrous MgSO₄ and filtered. For all reactions, the products were identified using GC/MS and GC/FID and NMR by comparison with the authentic samples. Trace soluble side products observed in naphthyl alkyl ether reductions included naphthalene, 1,2,3,4-tetrahydronaphthalene, and 5,6,7,8-tetrahydro-2-naphthol.

In most cases, the products were isolated and purified before characterization by NMR and/or GC-MS, either by independent spectral analysis or comparison with authentic samples, or both. In those cases where the product was not isolated and purified, characterization was made on the basis of GC-MS and/or GC-FID analyses.

Example 6: Selected Reactions

Example 6.1: Reactions of 4-(Triethylsilyl)dibenzofuran

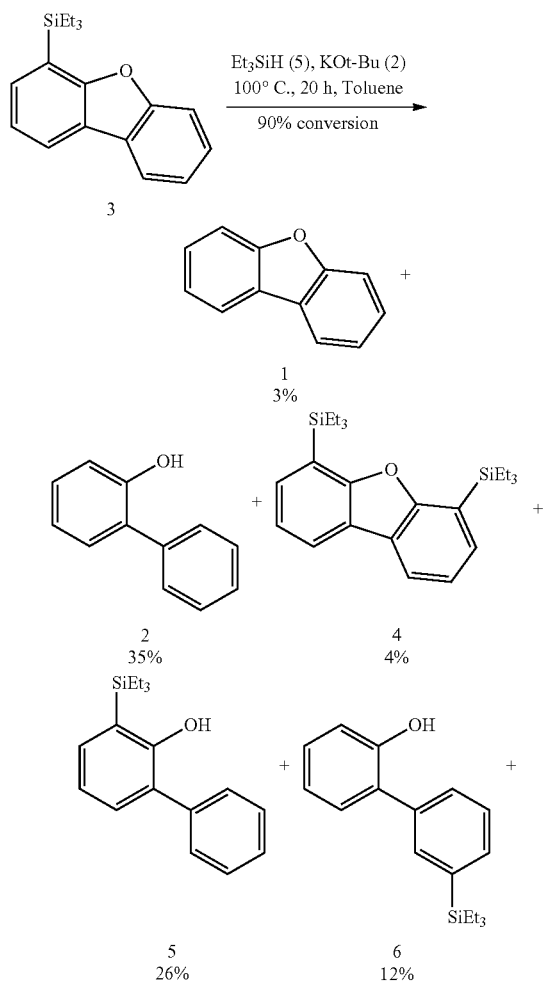

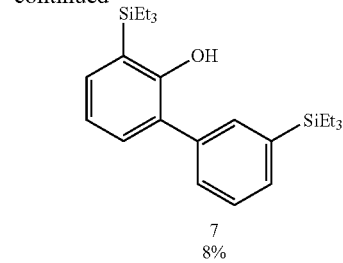

The reaction was conducted according to the General Procedure by heating 4-Et₃Si-dibenzofuran (3, 141 mg, 0.5 mmol, 1 equiv.), KOt-Bu (112 mg, 1 mmol, 2 equiv.) and Et₃SiH (401 microliters, 2.5 mmol, 5 equiv.) in 2 ml of toluene for 20 hours at 100° C. After acidic aqueous work up, the crude reaction mixture was purified by chromatography on silica using hexanes and hexanes-ether (10:1) to isolate 2-phenylphenol (2, 30 mg, 0.177 mmol, 35%), 2-triethylsilyl-6-phenylphenol (5, 37 mg, 0.134 mmol, 26%), 2-(3-triethylsilylphenyl)phenol (6, 17 mg, 0.063 mmol, 12%). Quantities of unconsumed 3 as well as products 1, 4 and 7 were obtained using post-chromatography GC-FID analysis of the corresponding mixed fractions.

Example 6.2: Investigation of Silylated Dibenzofurans as Intermediates Towards C—O Bond Cleavage: Cleavage Attempts with KOt-Bu

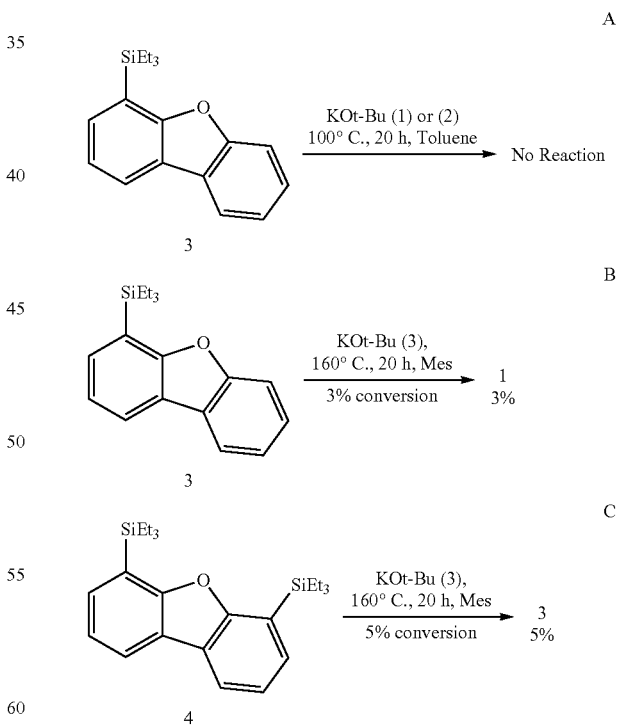

Starting material 3 (14.1 mg, 0.05 mmol, 1 equiv.) was heated with KOt-Bu (5.6 mg or 11.2 mg, 1 or 2 equiv., respectively) in 0.8 ml d-toluene at 100° C. for 20 hours in a J. Young tube under nitrogen. Monitoring the reaction progress by ¹H NMR showed no conversion of 3 in both cases. Likewise, starting materials 3 (28.2 mg, 0.1 mmol, 1 equiv.) or 4 (39.6 mg 0.1 mmol, 1 equiv.) were heated with KOt-Bu (36.6 mg) in 0.3 mL of mesilylene at 160° C. for 20 hours. Subsequent analysis of the crude reaction mixtures by GC-FID or 1H NMR revealed 3% conversion to 1 in case of 3 and 5% conversion to 3 from 4.

Example 6.3: Reactions of 4-(Methoxy)dibenzofuran at Elevated Temperature

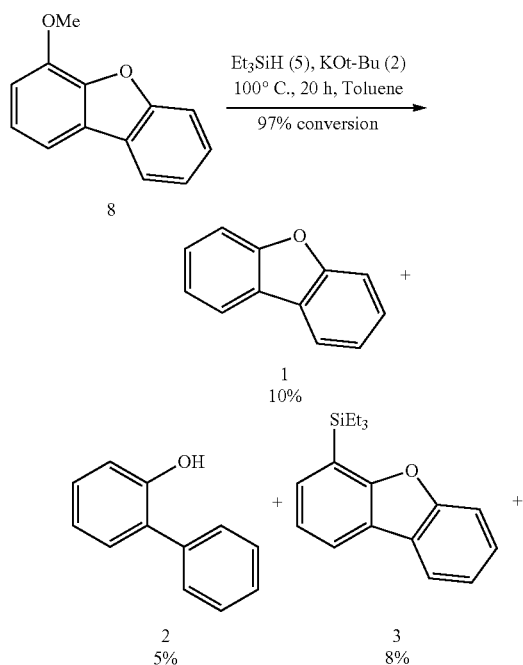

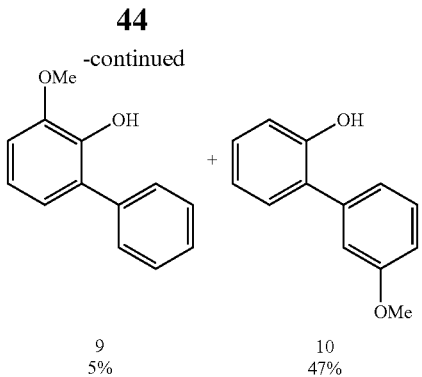

9
5%

10
47%

The reaction was conducted according to the General Procedure by heating 4-MeO-dibenzofuran (8, 89 mg, 0.5 mmol, 1 equiv.), KOt-Bu (112 mg, 1 mmol, 2 equiv.) and Et₃SiH (401 microliters, 2.5 mmol, 5 equiv.) in 2 ml of toluene for 20 hours at 100° C. After aqueous work up, the crude reaction mixture was purified by chromatography on silica using hexanes and hexanes-ether to recover unconsumed starting material 8 (3 mg, 0.015 mmol, 3%) and isolate dibenzofuran (1, 8.4 mg, 0.05 mmol, 10%; since fractions of 1 contained small amounts of starting 8, quantification was done by ¹H-NMR with CH₂Br₂ as an internal standard), 1,1'-biphenyl-2-ol (2, 4.3 mg, 0.025 mmol, 5%), 4-Et₃Si-dibenzofuran (3, 11 mg, 0.039 mmol, 8%), 2-methoxy-6-phenyl-phenol (9, mg, 0.025 mmol, 5%), 2-(3'-methoxyphenyl)phenol (10, 47 mg, 0.235 mmol, 47%). Note: only compounds with the yield exceeding 2% were characterized. ¹H and ¹³C NMR spectral assignments of 9 and 10 were consistent with literature reports.

Example 6.4: Triethylsilylation of Arenes

Example 6.4.1: At Elevated Temperatures

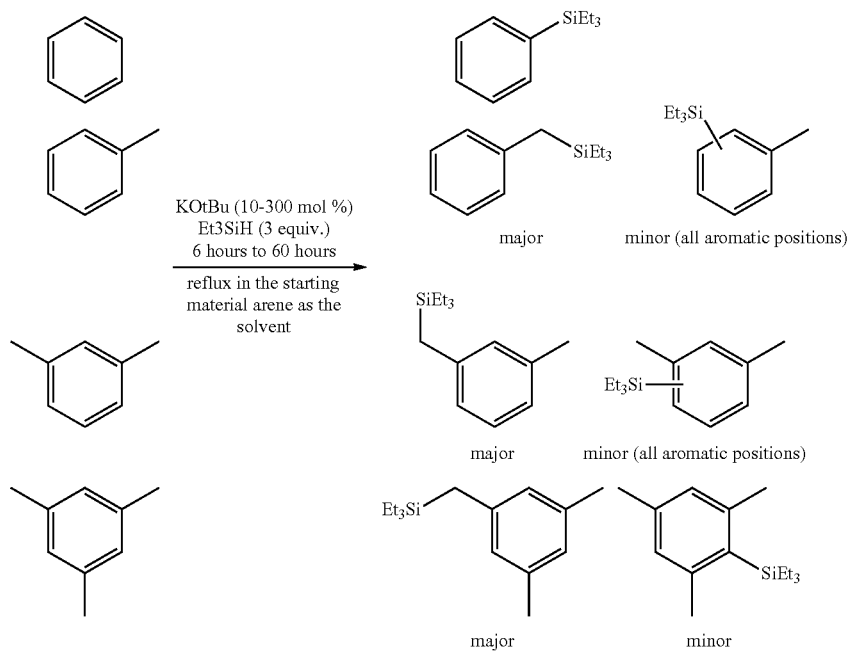

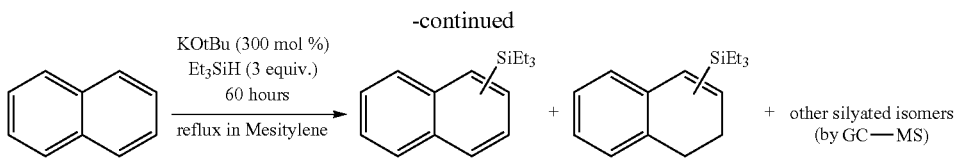

In many instances the formation of the solvent-derived silylated products was observed at elevated temperatures during experiments aimed at C—O, C—N, or C—S bond cleavage when using toluene or mesilylene as solvents at the elevated temperatures used in the reductive cleavage reactions. Since it was not possible to separate the resulting products from their respective parent solvents by column chromatography or distillation, at this point it was difficult to assess their yields, but they are tentatively estimated to be in 5-10% range based on Et$_3$SiH. In case of toluene, the identity of products was confirmed by comparison of the NMR spectra obtained with the literature data (Rychnovsky, et al. *J. Org. Chem.* 2003, 68, 10135.) Thus, it was concluded that the major product is benzyl triethylsilane (17), which is also consistent with the GC-MS analysis of fragmentation patterns of isomeric products. Likewise, it appeared that silylation of mesilylene proceeds predominantly into the benzylic (or alpha) position. HRMS [C$_{15}$H$_{26}$Si] calculated 234.1804, measured 234.1804).

Example 6.4.2: Direct C(sp$^3$)-H Silylation Reactions

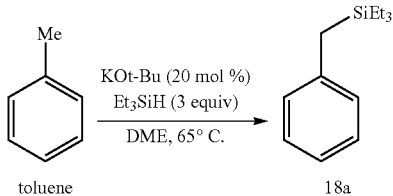

Benzyltriethylsilane 18a: The reaction was conducted according to the General Procedure by heating KOt-Bu (11.2 mg, 0.1 mmol, 20 mol %), toluene (46 mg, 0.5 mmol, 1 equiv), Et$_3$SiH (243 µL, 1.5 mmol, 3 equiv) and DME (0.5 mL) at 65° C. for 108 h. C(sp$^3$):C(sp$^2$)=18:1. The GC yield of desired product 18a is 53%. The analytically pure product (25.0 mg, 24% yield) was obtained as a colorless oil after evaporation of starting material and volatiles under vacuum (60 millitorr, 23° C.). Note: compound 18a is volatile and readily removed under vacuum. Rf=0.8 (100% hexanes); $^1$H NMR (500 MHz, CDCl$_3$) δ 7.22 (m, 2H), 7.09-7.05 (m, 1H), 7.05-7.02 (m, 2H), 2.12 (s, 2H), 0.96-0.91 (t, 9H), 0.53 (q, J=7.9 Hz, 6H).

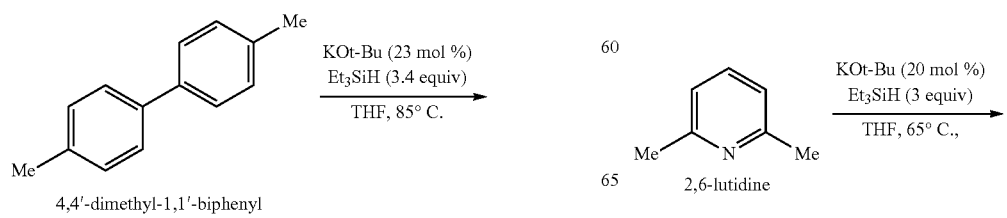

Triethyl((4-methyl-[1,1'-biphenyl]-4-yl)methyl)silane 18b: The reaction was conducted according to the General Procedure by heating KOt-Bu (11.2 mg, 0.1 mmol, 23 mol %), 4,4'-dimethyl-1,1'-biphenyl (80.0 mg, 0.44 mmol), Et$_3$SiH (240 µL, 1.5 mmol, 3.4 equiv), and 0.5 mL of THF at 85° C. for 96 h. The ratio of mono-silylation product to bis-silylation product is 16:1. A mixture of desired product 18b and starting material 4,4'-dimethyl-1,1'-biphenyl (69.7 mg of mixture, contains 56.6 mg of 18b, 43% yield, calculated based on 1H NMR) was obtained after purification by silica gel flash chromatography (100% hexanes). A small fraction of analytically pure compound 18b was obtained as a colorless oil after subsequent purification by silica gel flash chromatography. Rf=0.5 (100% hexanes); $^1$H NMR (500 MHz, CDCl$_3$) δ 7.50-7.47 (m, 2H), 7.46-7.42 (m, 2H), 7.25-7.21 (m, 2H), 7.11-7.04 (m, 2H), 2.39 (s, 3H), 2.14 (s, 2H), 0.95 (t, J=7.9 Hz, 9H), 0.54 (q, J=8.0 Hz, 6H); $^{13}$C NMR (126 MHz, CDCl$_3$) δ 139.7, 138.5, 136.7, 136.5, 129.6, 128.6, 126.8, 126.7, 21.4, 21.2, 7.5, 3.1; IR (Neat Film, NaCl) 3022, 2951, 2909, 2873, 1610, 1497, 1455, 1416, 1238, 1209, 1153, 1005, 845, 806, 773, 729 cm$^{-1}$; HRMS (EI+) calc'd for C$_{20}$H$_{28}$Si [M+.]: 296.1960, found 296.1954.

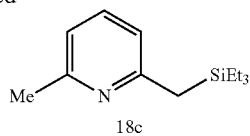

18c

2-Methyl-6-((triethylsilyl)methyl)pyridine 18c: The reaction was conducted according to the General Procedure by heating KOt-Bu (11.2 mg, 0.1 mmol, 20 mol %), 2,6-lutidine (53.5 mg, 0.5 mmol), Et$_3$SiH (240 μL, 1.5 mmol, 3 equiv), and 0.5 mL of THF at 65° C. for 120 h. The desired product 18c (58.6 mg, 53% yield) was obtained after purification by silica gel flash chromatography (gradient elution, 5%→10% EtOAc in hexanes) as a colorless oil. Note: compound 18c is volatile and is readily removed under vacuum. Rf=0.3 (5% EtOAc in hexanes); $^1$H NMR (500 MHz, CDCl$_3$) δ 7.36 (t, J=7.6 Hz, 1H), 6.90-6.73 (m, 2H), 2.47 (s, 3H), 2.32 (s, 2H), 0.98-0.83 (m, 9H), 0.58-0.48 (m, 6H); $^{13}$C NMR (126 MHz, CDCl$_3$) δ 160.8, 157.4, 135.9, 119.0, 118.4, 25.4, 24.5, 7.2, 3.3; IR (Neat Film, NaCl) 3060, 2951, 2874, 1587, 1575, 1450, 1414, 1372, 1269, 1238, 1145, 1078, 1016, 919, 796, 748, 726 cm$^{-1}$; HRMS calc'd for C$_{13}$H$_{24}$NSi [M+H]+: 222.1678, found 222.1666.

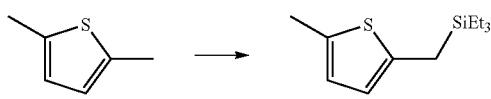

Silylation of 2,5-dimethyl thiophene: The reaction was conducted according to the General Procedure by heating 2,5-dimethyl thiophene (56 mg, 0.5 mmol, 1 equiv.), KOt-Bu (11.2 mg, 0.1 mmol, 0.2 equiv.) and Et$_3$SH (3 equiv.) in tetrahydrofuran for 45 hours at 65° C. GC-MS of the crude product mixture yielded a mass peak associated with the monosilated derivative. $^1$H NMR data were consistent with formation of 2-methyl-5-(triethylsilylmethyl)thiophene, $^1$H NMR (500 MHz, THF-d8) δ 6.52-6.42 (m, LH), 6.41-6.29 (m, 1H), 2.35 (s, 3H), 2.23 (s, 2H), 1.00-0.92 (m, 9H), 0.63-0.53 (m, 6H). $^{13}$C NMR (126 MHz, THF-d8) δ 140.78, 136.28, 125.96, 124.03, 15.73, 15.45, 7.97, 4.08. HRMS: [C$_{12}$H$_{22}$SSi] calculated 226.1212, measured 226.1220

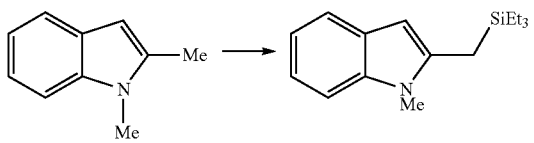

Silylation of N-methyl-2-methylindole: The reaction was conducted according to the General Procedure by heating 1,2-dimethylindole (73 mg, 0.5 mmol, 1 equiv.), KOt-Bu (17 mg, 0.15 mmol, 0.3 equiv) and Et$_3$SiH (319 microliters, 2.0 mmol, 4 equiv.) in 1 mL of tetrahydrofuran for 65 hours at 65° C. After aqueous work up, the crude reaction mixture was purified by chromatography on silica using an 80:1:4 mixture of hexanes:Et$_2$O:Et$_3$N respectively to obtain 74 mg (57%) of the title compound as a colourless oil. $^1$H NMR (500 MHz, THF-d$_8$) δ 7.35-7.29 (m, 1H), 7.19 (dd, J=8.1, 0.9 Hz, 1H), 6.97 (ddd, J=8.2, 7.1, 1.2 Hz, 1H), 6.90 (ddd, J=8.0, 7.1, 1.1 Hz, 1H), 6.06 (d, J=0.8 Hz, 1H), 3.64 (s, 3H), 2.25 (d, J=0.7 Hz, 2H), 0.96 (t, J=7.9 Hz, 9H), 0.71-0.58 (m, 6H), $^{13}$C NMR (126 MHz, THF-d$_8$) δ 139.50, 138.30, 129.69, 120.24, 119.70, 119.47, 109.27, 98.96, 29.75, 11.73, 7.62, 4.16. HRMS: [C$_{16}$H$_{25}$NSi] calculated 259.1756, measured 259.1754. The HSQC spectrum of this reaction product has previously been reported in U.S. Pat. No. 9,000,167.

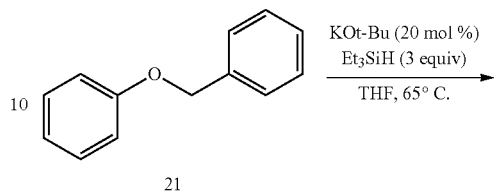

Triethyl(phenoxy(phenyl)methyl)silane 22: The reaction was conducted according to the General Procedure by heating KOt-Bu (11.2 mg, 0.1 mmol, 20 mol %), (benzyloxy)benzene 21 (92.0 mg, 0.5 mmol), Et$_3$SiH (240 μL, 1.5 mmol, 3 equiv), and 0.25 mL of THF at 65° C. for 120 h. The desired product 22 (68.4 mg, 46% yield) was obtained after purification by silica gel flash chromatography (100% hexanes) as a colorless oil. Rf=0.3 (100% hexanes); $^1$H NMR (500 MHz, CDCl$_3$) δ 7.46-7.37 (m, 4H), 7.38-7.28 (m, 4H), 7.30-7.20 (m, 2H), 5.80 (s, 1H), 0.92 (t, J=7.9 Hz, 9H), 0.66-0.55 (m, 6H); $^{13}$C NMR (126 MHz, CDCl$_3$) δ 145.3, 128.1, 128.1, 126.9, 126.9, 126.4, 126.3, 6.7, 4.9; IR (Neat Film, NaCl) 3063, 3026, 2954, 2875, 1598, 1492, 1454, 1413, 1302, 1239, 1188, 1090, 1065, 1006, 974, 833, 740, 700 cm$^{-1}$; HRMS (EI+) calc'd for C$_{19}$H$_{25}$OSi [(M+H)–H2]+: 297.1675, found 297.1668.

Aromatic amines are also amenable to silylation. In the following case, GC-MS identified the following scheme was operable under the conditions provided:

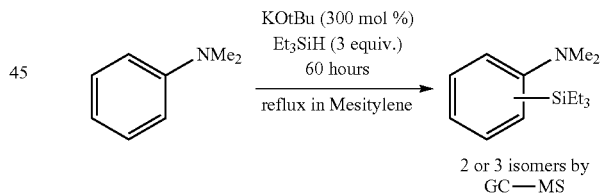

2 or 3 isomers by GC—MS

At lower temperatures, this reaction appeared to provide a mixture of product, with no single product identifiable. It is possible, though not confirmed, that the apparent normal proclivity to silylate ortho to the exocyclic amine was inhibited by the steric bulk associated with the two methyl groups.

Example 6.5: Silylation of Dibenzofuran at Elevated Temperatures

Experiments were conducted using the General Procedures, unless otherwise indicated. Yields were reproducible within ±2%. It is noteworthy here that low levels of base, especially substoichiometric amounts of base relative to the substrate, even at these elevated temperatures, resulted in the highest yields of silylated products, relative to cleavage products.

TABLE 4

Results of silylation of dibenzofuran at elevated temperatures

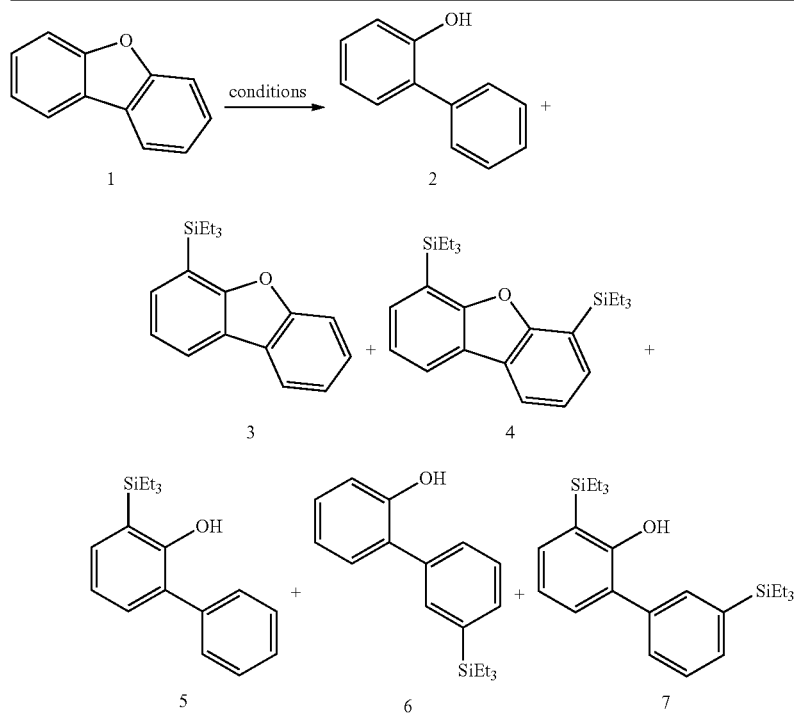

| Entry | Et$_3$SiH (equiv) | Base (equiv) | Solvent | T, °C. | Conv (%)$^a$ | 2 | 3 | 4 | 5 | 6 | 7 |
|---|---|---|---|---|---|---|---|---|---|---|---|
| 1 | 0 | KOt-Bu (2) | Toluene | 100 | 0 | — | — | — | — | — | — |
| 2 | 5 | None | Toluene | 100 | 0 | — | — | — | — | — | — |
| 3$^a$ | 5 | KOt-Bu (2) | Toluene | 100 | 70 | 34 | 28 | 4 | — | — | — |
| 4$^b$ | 5 | KOt-Bu (2) | Toluene | 100 | 98 | 38 | 16 | 10 | 21 | 2 | 7 |
| 5$^c$ | 5 | KOt-Bu (2) | Toluene | 100 | 98 | 5 | 28 | 46 | — | — | — |
| 6 | 4 | KOt-Bu (2) | Toluene | 100 | 100 | 41 | 17 | 15 | 12 | 1 | 9 |
| 7 | 3 | KOt-Bu (2) | Toluene | 100 | 96 | 42 | 20 | 9 | 13 | 1 | 4 |
| 8 | 2 | KOt-Bu (2) | Toluene | 100 | 87 | 34 | 30 | 10 | 6 | 1 | 3 |
| 9 | 1 | KOt-Bu (2) | Toluene | 100 | 56 | 19 | 29 | 1 | 2 | — | 1 |
| 10 | 5 | KOt-Bu (0.5) | Toluene | 100 | 89 | 12 | 48 | 20 | 9 | — | 1 |
| 11 | 2 | KOt-Bu (5) | Toluene | 100 | 66 | 9 | 43 | 8 | 2 | — | — |
| 12 | 3 | KOt-Bu (2) | Toluene | 100 | 97 | 63 | 10 | 1 | 22 | — | 2 |
| 13 | 5 | KH (1) | Dioxane | 100 | 49 | 1 | 43 | 5 | — | — | — |
| 14 | 5 | KOt-Bu (2) | Dioxane | 100 | 70 | 25 | 28 | 10 | 4 | 1 | 1 |
| 15$^d$ | — | KOt-Bu (2) | Et$_3$SiH | 100 | 99 | 26 | 13 | 25 | 11 | 1 | 21 |
| 16 | 5 | KOt-Bu (2) | Toluene | 80 | 98 | 29 | 18 | 26 | 9 | — | 7 |
| 17 | 3 | KOt-Bu (3) | Mesitylene | 165 | 100 | 85 | 3 | — | 5 | 2 | — |
| 18$^e$ | 3 | KOt-Bu (3) | Mesitylene | 165 | 100 | 95 | — | — | — | — | — |
| 19 | 2 | KOt-Bu (2) | Mesitylene | 165 | 100 | 62 | 8 | 1 | 12 | 1 | — |
| 20 | 3 | KOt-Bu (2) | Mesitylene | 165 | 97 | 52 | 17 | 5 | 16 | 1 | 2 |
| 21 | 1 | KOt-Bu (1) | Mesitylene | 165 | 57 | 30 | 21 | — | — | — | — |

TABLE 4-continued

Results of silylation of dibenzofuran at elevated temperatures

| | | | | | | | | | | | |
|---|---|---|---|---|---|---|---|---|---|---|---|
| 22 | 3 | KOt-Bu (0.5) | Mesitylene | 165 | 85 | 29 | 35 | 15 | 4 | — | 2 |
| 23 | 5 | KOt-Bu (5) | Mesitylene | 165 | 100 | 77 | 3 | 0 | 3 | 8 | — |
| 24 | 3 | KH (3) | Mesitylene | 165 | 100 | 66 | 3 | 0 | 5 | 11 | — |
| 25 | 3 | KOEt (3) | Mesitylene | 165 | 100 | 85 | 4 | 0 | 1 | 8 | — |
| 26 | 3 | KOEt (3) | Mesitylene | 165 | 95 | 77 | 10 | 11 | — | — | — |
| 27 | 3 | KOEt (3) | Toluene | 100 | 40 | 19 | 19 | 2 | — | — | — |
| 28 | 3 | KOMe (3) | Mesitylene | 165 | 64 | 31 | 27 | 2 | 3 | 1 | — |
| 29 | 3 | NaOt-Bu (3) | Mesitylene | 165 | 0 | — | — | — | — | — | — |
| 30 | 3 | LiOt-Bu (3) | Mesitylene | 165 | 0 | — | — | — | — | — | — |
| 31 | 3 | NaOEt (3) | Mesitylene | 165 | 0 | — | — | — | — | — | — |
| 32[f] | 3 | CsOR (2) | Toluene | 100 | 89 | 75 | 3 | 11 | — | — | — |
| 33 | 3 | KOt-Bu (3) | Benzene | 85 | 96 | 37 | 20 | 13 | 12 | — | 9 |
| 34 | 5 | KOt-Bu (2) | DMF | 100 | 0 | — | — | — | — | — | — |
| 35 | 5 | KOt-Bu (2) | DMA | 100 | 0 | — | — | — | — | — | — |
| 36 | 5 | KOt-Bu (2) | Diglyme | 100 | 0 | — | — | — | — | — | — |
| 37 | 5 | KOt-Bu (2) | t-BuOH | 100 | 0 | — | — | — | — | — | — |
| 38 | 5 | KOt-Bu (2) | Diisopropyl carbonol | 100 | 0 | — | — | — | — | — | — |
| 39 | 3 | KOt-Bu (3) | Methyl cyclohexane | 160 | 100 | 82 | — | — | 13 | — | — |
| 40[g] | PMHS (10) | KOt-Bu (3) | Methyl cyclohexane | 85 | 5-7 | — | — | — | — | — | — |

[a] GC yields and conversions are reported using tridecane as the standard
[b] the reaction was performed in 0.05 M solution.
[c] reaction conducted open to an Ar line
[d] the reaction was performed in neat Et$_3$SiH.
[e] with 1,4-cyclohexadiene (100 equivalent) co-solvent
[f] R = 2-ethylhexyl.
[g] using polymethylhydrosiloxane (PMHS) instead of Et$_3$SiH as organosilane

Example 6.6: Silylation of Aryl Alkyl Ethers at Elevated Temperatures

Silylations of aryl alkyl ethers at elevated temperatures were conducted under the conditions applied to diaryl ethers to probe the cleavage selectivity of sp$^2$ versus sp$^3$ C—O bond. At the elevated temperatures of these experiments, the reaction of 2-methoxynaphthalene gave 2-naphthol as the major product in moderate yield (Scheme 1). GC-MS analysis of the crude reaction mixture indicated the presence of trace amounts of naphthalene along with 2-methylnaphthalene and further reduced species, including products of partial aromatic reduction. Compounds presumably derived from 2-naphthol silylation were also detected. Likewise, cleavage of 2-ethoxynapthalene under the same conditions gave 2-naphthol in slightly higher yield, but with the same or analogous side products. Sterically bulkier ethers were investigated to probe the versatility and possible mechanism of the C—O bond cleavage. Despite the large alkyl substituent adjacent to the ether oxygen, reaction of 2-neopentyloxynaphthalene provided 2-naphthol in approximately the same yield as with the less bulky substrates. Even 2-tert-butyloxynapthalene was cleaved to give the expected naphthol in 55% yield (Scheme 1). Control experiments performed at identical conditions but without triethylsilane provided 2-naphthol in cases of 2-ethoxy- and 2-tert-butyloxynapthalene albeit with substantially diminished yields. Since 2-methoxy- and 2-neopentyloxy-substrates remained intact in such silane-free cleavages, a b elimination mechanism is likely to be operative. When attempting to reduce 4-tert-butyl and 4-methyl anisoles under the standard conditions, the yields of the corresponding phenols were high, likely because of more challenging silylation of the substituted phenyl ring for the steric reasons (Scheme 2).

Scheme 1. Reductive Cleavage of Aryl Alkyl Ethers at Elevated Temperatures

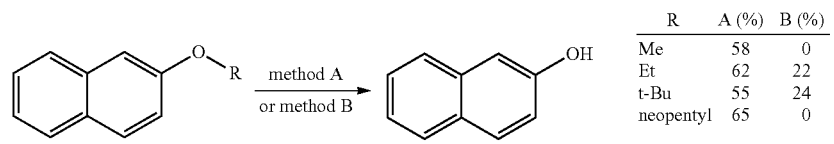

| R | A (%) | B (%) |
|---|---|---|
| Me | 58 | 0 |
| Et | 62 | 22 |
| t-Bu | 55 | 24 |
| neopentyl | 65 | 0 |

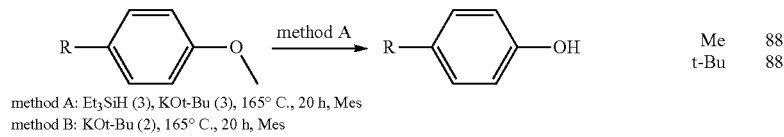

| | Me | 88 |
|---|---|---|
| | t-Bu | 88 | method A: Et$_3$SiH (3), KOt-Bu (3), 165° C., 20 h, Mes
method B: KOt-Bu (2), 165° C., 20 h, Mes Overall, the selectivity for alkyl C—O bond scission contrasts with that observed in Ni— and borane catalyzed C—O cleavage reactions where aryl C—O reduction occurs. It is also notable that under these conditions only trace amounts of naphthalene ring hydrogenation products were observed, which contrasts with the results of silane-based ionic hydrogenations reported in the literature.

It was instructive to compare the cleavages of methoxy-substituted diaryl ethers 8 and 11 (Scheme 2) with the results presented above. While aryl alkyl ethers show strong preference for the reduction of alkyl oxygen over aryl oxygen bonds, both methoxy substrates in Scheme 2 demonstrate a reversal of regioselectivity, furnishing almost exclusively aryl oxygen bond rupture products. While not intending to be bound by the correctness of this theory, this effect may be attributed to the presence of a donor oxygen atom ortho to the C—O bond undergoing rupture. Supporting this inference is the high selectivity of the reductive ring-opening of dibenzofuran derivative 8 that mainly leads to 10. Likewise, preferred formation of phenol and anisole is observed with similar selectivity over phenols 12 and 13 in the cleavage of lignin model 11. One may speculate that such an effect can be rationalized by the oxygen atom resonance stabilization of the positive charge build up during electrophilic activation of the C—O bond that is being broken. In order to test this hypothesis, compound 3 was subject to the reaction conditions and isolated the ring opened phenols 5 and 6 along with the desilylated products 1 and 2 (Scheme 2, inset C). In the absence of resonance stabilization, the selectivity of cleavage was reversed in favour of isomer 5. It is also worth noting that, as formation of 1 and 2 demonstrates, the silylation reaction is thus reversible under the typical reaction conditions. After having illustrated the potential for the challenging 4-O-5 lignin models 8 and 11, this method was tested with an oligomeric ether 14 that contains six C$_{ar}$—O bonds (Scheme 2, inset D). Remarkably, at 165° C. in mesilylene quantitative conversion of 14 was achieved and gave phenol, benzene, resorcinol and other unidentified products with merely 0.5 equivalent of silane per aryl oxygen bond.

In Scheme 2, compounds 1 to 7 refer to the corresponding compounds described in Example 6.5.

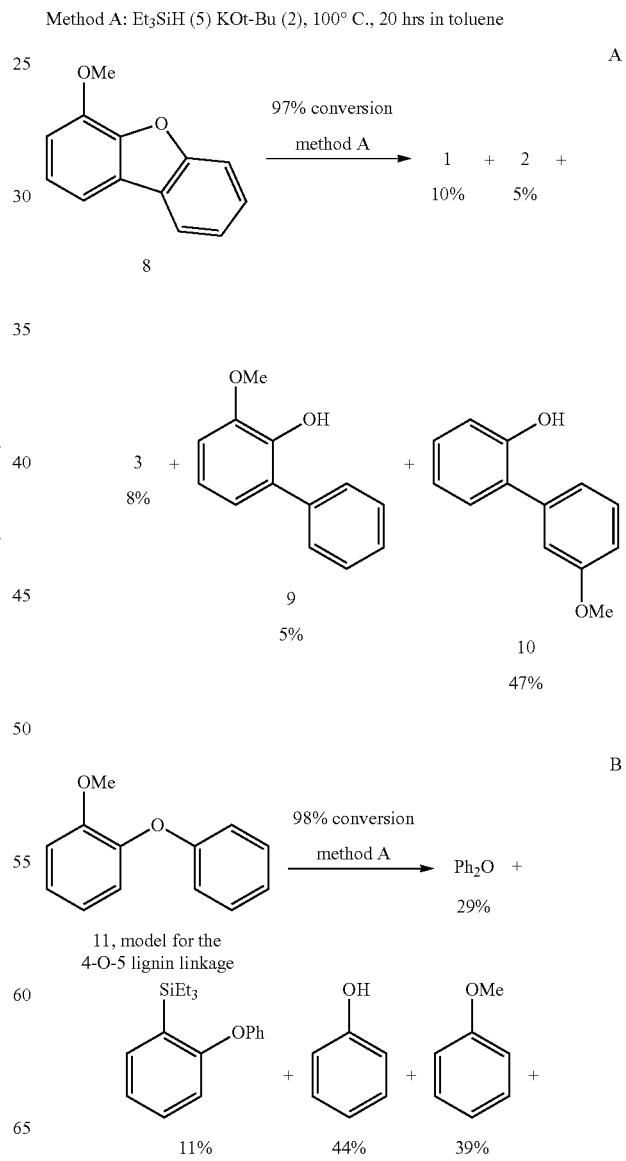

Scheme 2.

Method A: Et$_3$SiH (5) KOt-Bu (2), 100° C., 20 hrs in toluene

-continued

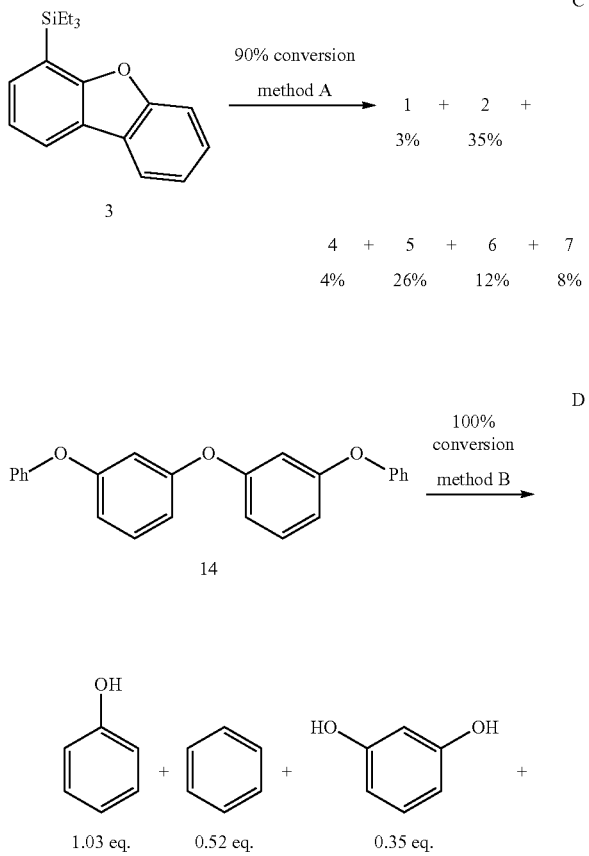

Method B: Et₃SiH (3) KOt-Bu (3), 165° C., 20 hrs in mesitylene

Example 6.7: Silylation of Aryl Alkyl Ethers and Thioethers at Ambient or Near Ambient Temperatures

Example 6.7.1: Triethyl(2-methoxyphenyl)silane

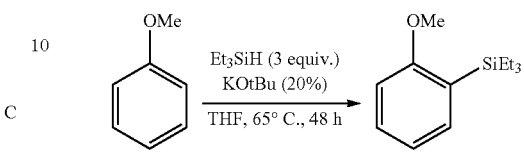

The reaction was conducted according to the General Procedure by heating anisole (54 mg, 0.5 mmol, 1 equiv.), KOt-Bu (11 mg, 0.1 mmol, 0.2 equiv) and Et₃SiH (239 microliters, 1.5 mmol, 3 equiv.) in 1 mL of tetrahydrofuran for 65 hours at 65° C. After aqueous work up, the crude reaction mixture was purified by chromatography on silica using hexanes (isochratic) to obtain 59 mg (54%) of the title compound as a colourless oil. $^1$H NMR (500 MHz, THF-d8) δ 7.40-7.17 (m, 2H), 7.01-6.81 (m, 2H), 3.77 (s, 3H), 1.02-0.85 (m 9H), 0.87-0.74 (m, 6H). $^{13}$C NMR (126 MHz, THF-d8) δ 164.58, 135.52, 130.42, 123.92, 120.08, 109.23, 54.09, 6.93, 3.22.

The reaction was conducted according to the General Procedure by heating KOt-Bu (11.2 mg, 0.1 mmol, 20 mol %), anisole (54.0 mg, 0.5 mmol, 1 equiv), and Et₃SiH (243 µL, 1.5 mmol, 3 equiv) without any added solvent at 85° C. for 72 h. ortho:(meta+para)>20:1. The GC yield of desired product 17a is 65%. The analytically pure product (47.7 mg, 43% yield) was obtained as a colorless oil after evaporation of starting material and volatiles under vacuum (60 millitorr, 23° C.). Note: compound 17a is volatile and can be removed under vacuum. Rf=0.3 (10% Et2O in hexanes). 1H NMR (500 MHz, CDCl₃) δ 7.41-7.30 (m, 2H), 6.97 (m, 1H), 6.87-6.81 (m, 1H), 3.80 (s, 3H), 1.05-0.90 (m, 9H), 0.91-0.77 (m, 6H).

Example 6.7.2: Triethyl(3-methoxynaphthalen-2-yl)silane

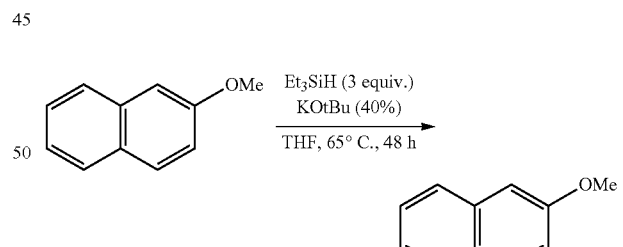

The reaction was conducted according to the General Procedure by heating 2-methoxynaphthalene (79 mg, 0.5 mmol, 1 equiv.), KOt-Bu (19.6 mg, 0.18 mmol, 0.35 equiv.) and Et₃SiH (319 microliters, 2.0 mmol, 4 equiv.) in 1 mL of tetrahydrofuran for 48 hours at 65° C. After aqueous work up, the crude reaction mixture was purified by chromatography on silica eluting with hexanes (isochratic) to obtain 79 mg (58%) of the title compound as colourless oil. $^1$H NMR (500 MHz, THF-d8) δ 7.84 (s, 1H), 7.78-7.73 (d, 1H), 7.73-7.68 (d, 1H), 7.38 (ddd, J=8.2, 6.8, 1.3 Hz, 1H), 7.27 (ddd, J=8.1, 6.8, 1.2 Hz, 1H), 7.15 (s, 1H), 3.90 (s, 3H), 1.01-0.90 (m, 9H), 0.68-0.53 (m, 6H). $^{13}$C NMR (126 MHz, THF-d$_8$) δ 163.03, 137.88, 136.83, 130.10, 128.58, 128.09, 127.29, 127.21, 124.03, 104.57, 55.25, 8.02, 7.48. HRMS: [C$_{17}$H$_{24}$OSi] calculated 272.1608, measured 272.1596. The HSQC spectra of the 2-methoxynaphthalene and its reaction product has previously been reported in U.S. Pat. No. 9,000,167.

Interestingly, the reaction starting 1-methoxynaphthalene did not result in silylated product:

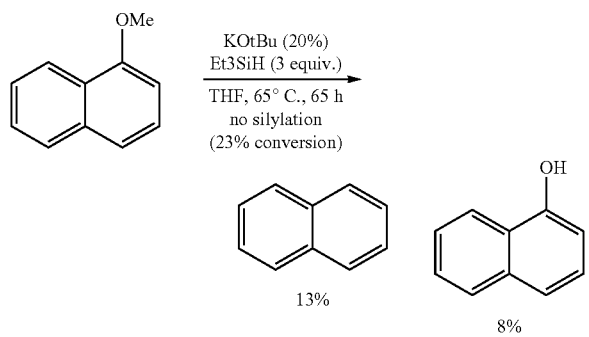

The reaction was conducted according to the General Procedure by heating 1-methoxynaphthalene (79 mg, 0.5 mmol, 1 equiv.), KOt-Bu (11.2 mg, 0.1 mmol, 0.1 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis. Analysis by GC-MS and GC-FID (tridecane standard) revealed the formation of aryl C—O cleavage product naphthalene and alkyl C—O bond cleavage product naphthol in 13 and 8 percent yield respectively, notably to the complete exclusion of any silylated species.

Example 6.7.3: Silylation of Diphenyl Ether

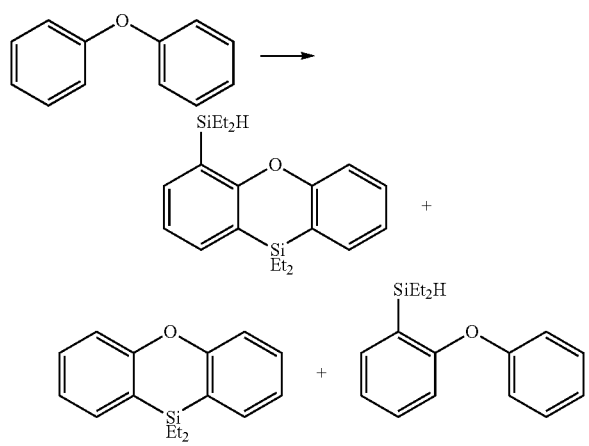

The reaction was conducted according to the General Procedure by heating phenyl ether (85 mg, 0.5 mmol, 1 equiv.), KOt-Bu (11 mg, 0.10 mmol, 0.2 equiv) and Et$_2$SiH$_2$ (194 microliters, 1.5 mmol, 3 equiv.) in 1 mL of tetrahydrofuran for 65 hours at 65° C. After aqueous work up, the crude reaction mixture was purified by chromatography on silica using an 80:2 mixture of hexanes:triethylamine to obtain 68 mg (20%) of the title compound as a colourless oily solid. $^1$H NMR (500 MHz, THF-d$_8$) δ 7.64-7.57 (m, 2H), 7.55 (dd, J=7.3, 1.8 Hz, 1H), 7.41 (ddd, J=8.3, 7.2, 1.8 Hz, 1H), 7.15 (dd, J=8.3, 1.0 Hz, 1H), 7.14-7.09 (m, 2H), 4.34 (Si—H) (p-like, J=1.2 Hz, 1H), 1.06-0.95 (m, 12H), 0.92-0.82 (m, 8H). $^{13}$C NMR (126 MHz, THF-d$_8$) δ 166.04, 161.43, 139.74, 137.00, 135.55, 135.05, 132.12, 130.19, 128.79, 123.56, 123.37, 118.41, 9.06, 7.93, 6.70, 4.83. HRMS: [C$_{20}$H$_{27}$OSi$_2$] calculated 339.1601, measured 339.1607

A second fraction of the reaction mixture yielded 34 mg (39%) of the cyclized derivative. $^1$H NMR (500 MHz, THF-d$_8$) δ 7.57-7.50 (m, 2H), 7.40 (ddd, J=8.3, 7.2, 1.8 Hz, 2H), 7.15 (dd, J=8.6, 0.7 Hz, 2H), 7.11 (td, J=7.2, 1.0 Hz, 2H), 0.99-0.95 (m, 4H), 0.92-0.86 (m, 6H). $^{13}$C NMR (126 MHz, THF-d$_8$) δ 161.54, 134.96, 132.07, 123.41, 118.80, 117.39, 7.95, 6.72. HRMS: [C$_{16}$H$_{19}$OSi] calculated 255.1205, measured 255.1206. The HSQC spectra of these reaction products have previously been reported in U.S. Pat. No. 9,000,167.

A third fraction was obtained, containing a product in low yield (ca. 7%) whose spectral characteristics appear to be consistent with the structure of the monosilylated product shown above.

In a second set of experiments, when oxydibenzene was used as the solvent, the reaction more cleanly produced the monosilylated derivative, triethyl(2-phenoxyphenyl)silane 17b:

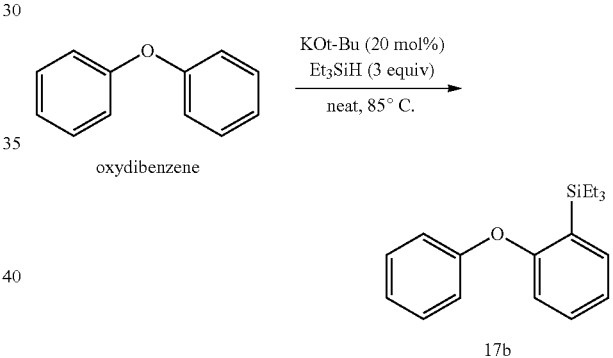

The reaction was conducted according to the General Procedure by heating KOt-Bu (11.2 mg, 0.1 mmol, 20 mol %), oxydibenzene (85.0 mg, 0.5 mmol), and Et$_3$SiH (240 μL, 1.5 mmol, 3 equiv) without solvent at 85° C. for 120 h. The desired product 17b (84.5 mg, 55% yield) was obtained after purification by silica gel flash chromatography (100% hexanes) as a colorless oil. Rf=0.4 (100% hexanes); $^1$H NMR (500 MHz, CDCl$_3$) δ 7.52-7.46 (m, 1H), 7.38-7.25 (m, 3H), 7.10 (t, J=7.4 Hz, 2H), 7.00 (d, J=7.9 Hz, 2H), 6.81 (d, J=8.1 Hz, 1H), 0.97 (t, J=7.9 Hz, 9H), 0.85 (q, J=7.9 Hz, 6H).

Example 6.7.4: Silylation of 1,4-dimethoxybenzene

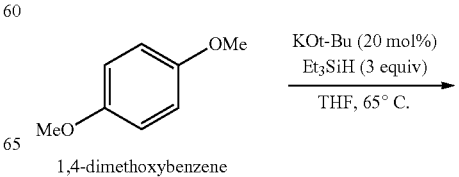

-continued

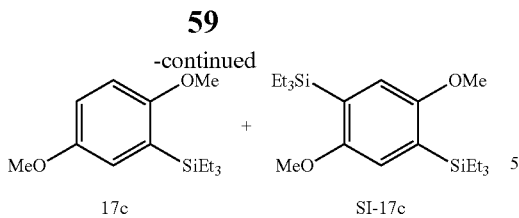

17c SI-17c

The reaction was conducted according to the General Procedure by heating KOt-Bu (11.2 mg, 0.1 mmol, 20 mol %), 1,4-dimethoxybenzene (69.1 mg, 0.5 mmol), and Et$_3$SiH (240 µL, 1.5 mmol, 3 equiv), in 0.5 mL of THF at 65° C. for 72 h. The desired product 17c (53.1 mg, 42% yield) and bis-silylated byproduct SI-17c (16.1 mg, 8% yield) were obtained after purification by silica gel flash chromatography (100% hexanes).

(2,5-Dimethoxyphenyl)triethylsilane 17c: Colorless oil, Rf=0.5 (100% hexanes); $^1$H NMR (500 MHz, CDCl$_3$) δ 6.93 (d, J=3.1 Hz, 1H), 6.85 (dd, J=8.8, 3.1 Hz, 1H), 6.76 (d, J=8.8 Hz, 1H), 3.80 (s, 3H), 3.74 (s, 3H), 0.99-0.91 (m, 9H), 0.85-0.74 (m, 6H); $^{13}$C NMR (126 MHz, CDCl$_3$) δ 158.8, 153.3, 126.7, 122.2, 122.3, 114.1, 55.7, 55.5, 7.6, 3.7; IR (Neat Film, NaCl) 2952, 2873, 1580, 1478, 1463, 1398, 1272, 1220, 1177, 1050, 1026, 872, 800, 769, 732 cm$^{-1}$; HRMS (EI+) calc'd for C$_{14}$H$_{24}$O$_2$Si [M+.]: 252.1546, found 252.1540.

(2,5-Dimethoxy-1,4-phenylene)bis(triethylsilane) SI-17c: White solid, Rf=0.8 (100% hexanes); $^1$H NMR (500 MHz, CDCl$_3$) δ 6.81 (s, 2H), 3.75 (s, 6H), 0.95 (td, J=7.9, 0.9 Hz, 9H), 0.85-0.77 (m, 6H); $^{13}$C NMR (126 MHz, CDCl$_3$) δ 158.5, 127.1, 116.9, 55.6, 7.7, 3.8; IR (Neat Film, NaCl) 2948, 2870, 1459, 1418, 1345, 1262, 1203, 1107, 1045, 999, 868, 727, 700 cm$^{-1}$; HRMS (EI+) calc'd for C$_{20}$H$_{38}$Si$_2$O$_2$ [M+.]: 366.2410, found 366.2415.

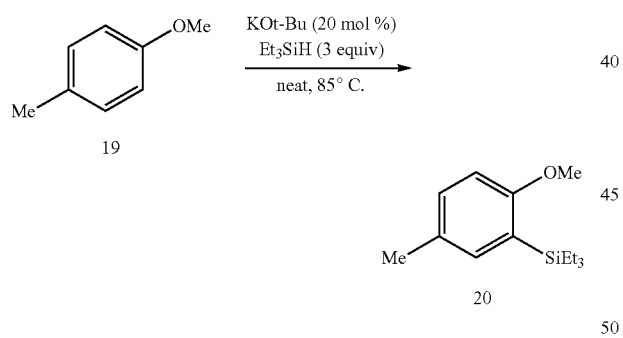

Triethyl(2-methoxy-5-methylphenyl)silane 20: The reaction was conducted according to the General Procedure by heating KOt-Bu (11.2 mg, 0.1 mmol, 20 mol %), 1-methoxy-4-methylbenzene 19 (61.0 mg, 0.5 mmol), and Et$_3$SiH (240 µL, 1.5 mmol, 3 equiv) at 85° C. for 120 h. The desired product 20 (38.5 mg, 32% yield) was obtained after purification by silica gel flash chromatography (100% hexanes) as a colorless oil. Rf=0.4 (100% hexanes); $^1$H NMR (500 MHz, CDCl$_3$) δ 7.17-7.08 (m, 2H), 6.74 (dt, J=8.7, 1.3 Hz, 1H), 3.76 (s, 3H), 2.30 (s, 3H), 0.97-0.92 (m, 9H), 0.85-0.79 (m, 6H); $^{13}$C NMR (126 MHz, CDCl$_3$) δ 162.7, 136.7, 130.9, 129.2, 125.0, 109.5, 55.2, 20.8, 7.8, 3.7; IR (Neat Film, NaCl) 2951, 2873, 1595, 1480, 1464, 1385, 1238, 1175, 1147, 1081, 1034, 1004, 876, 806, 708 cm$^{-1}$; HRMS (EI+) calc'd for C$_{14}$H$_{24}$OSi [M+.]: 236.1596, found 236.1598

Example 6.7.5: Triethyl((phenylthio)methyl)silane

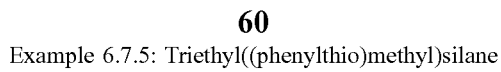
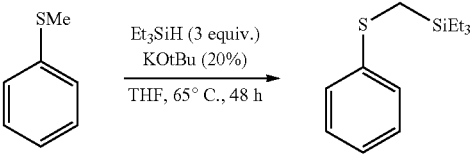

The reaction was conducted according to the General Procedure by heating thioanisole (62 mg, 0.5 mmol, 1 equiv.), KOt-Bu (11 mg, 0.1 mmol, 0.2 equiv) and Et$_3$SiH (239 microliters, 1.5 mmol, 3 equiv.) in 1 mL of tetrahydrofuran for 65 hours at 65° C. After aqueous work up, the crude reaction mixture was purified by chromatography on silica using hexanes (isochratic) to obtain 81 mg (68%) of the title compound as a colourless oil, $^1$H NMR (500 MHz, THF-d8) δ 7.31-7.26 (m, 2H), 7.25-7.19 (m, 2H), 7.11-7.01 (m, 1H), 1.03 (t, J=7.9 Hz, 9H), 0.78-0.60 (m, 6H). $^{13}$C NMR (126 MHz, THF-d8) δ 140.73, 128.31, 125.69, 124.19, 13.01, 6.62, 3.06. HRMS: [C$_{13}$H$_{21}$SSi] calculated 237.1140, measured 237.1133. The HSQC spectra of the thioanisole and its reaction product have previously been reported in U.S. Pat. No. 9,000,167.

Example 6.8: Experiments with C—N and C—S Heteroaryl Compounds at Elevated Temperatures Experiments were also conducted with C—N and C—S heteroaryl compounds. In the case of compounds comprising C—N bonds, reactivity appeared to be similar to that seen for C—O bonds, and it is reasonably expected that the wide ranging methods used for the latter will result in results in similar reactivity in the former:

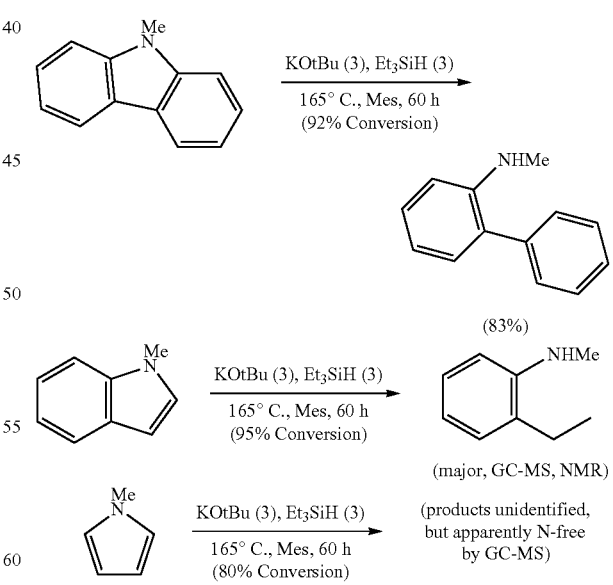

In the case of compounds comprising C—S compounds, the methods appear to generally result in complete desulfurization of the molecules, at least under the aggressive conditions of these experiments, reflecting the higher reactivity of these types of substrates (but compare with Examples 6.9.34 to 38). This difference in reactivities may reflect the differences in bond energies between the C—O, C—N, and C—S bonds (compare C—X bond dissociation energies in phenol (111), aniline (104), and thiophenol (85, all in kcal/mol). Of particular interest is the desulfurization of even hindered dibenzothiophenes under relatively mild conditions. In none of these conversions were single C—S products detected:

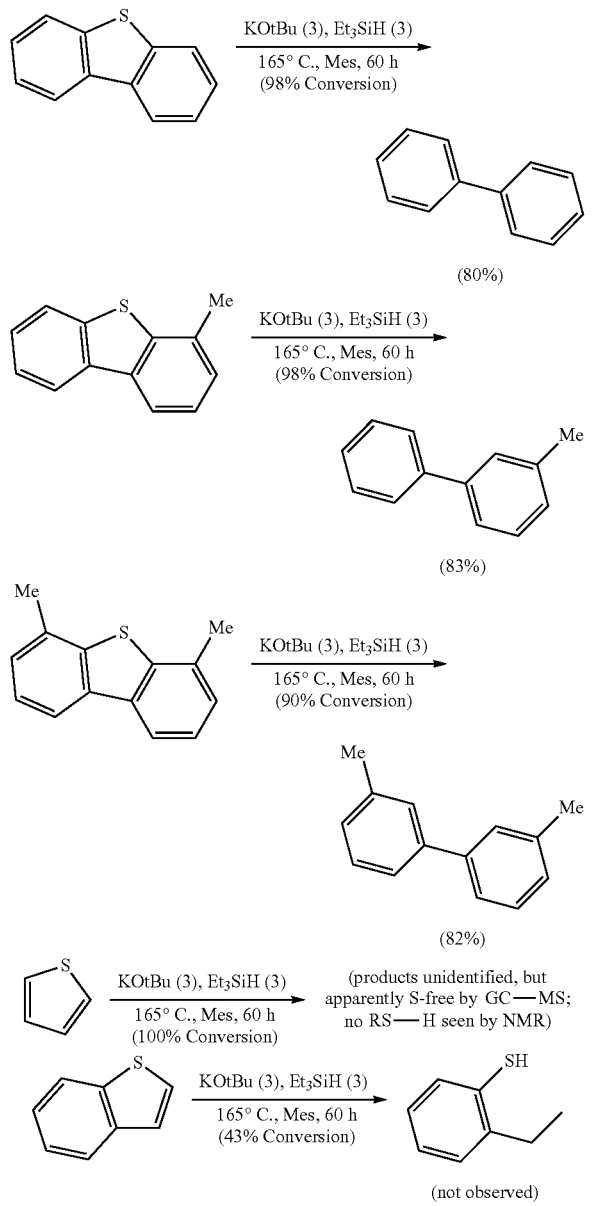

(Products unidentified, except no Ar—S observed by GC—MS; no RS—H by NMR)

Example 6.9: Experiments with Heteroaryl Compounds at Ambient or Near-Ambient Temperatures A series of experiments were done at ambient or near ambient temperatures (65° C. or below) to test the regioselectivity of several of the more reactive heteroaryl compounds. The test conditions and results are shown below. Yields for all reactions are either by isolation (chromatography on silica gel, or bulb-to-bulb distillation) or by GC-FID or NMR analysis using internal standard for quantification. Note that C-3 silylated heteroarenes were found in some cases to be prone to protodesilylation on silica gel. In these cases, bulb-to-bulb distillation was used or, alternatively, silica gel chromatography with ca. 3% triethyl amine added to the eluent, or a combination of both methods. Products were identified as indicated by $^1$H, $^{13}$C NMR, and Heteronuclear Single Quantum Coherence (HSQC) spectroscopy, or GC-MS, or a combination of both, where possible using comparisons with authentic samples.

Example 6.9.1: 1-methyl-2-(triethylsilyl)-1H-indole 2a

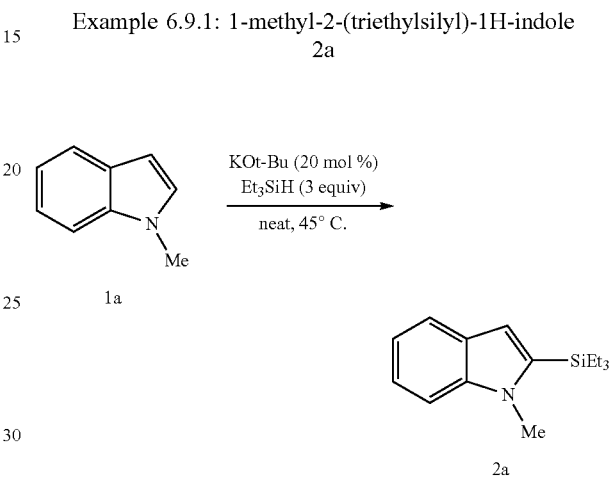

The reaction was conducted according to the General Procedure by heating KOt-Bu (11.2 mg, 0.1 mmol, 20 mol %), N-methylindole 1a (65.5 mg, 0.5 mmol, 1 equiv) and Et$_3$SiH (243 µL, 1.5 mmol, 3 equiv) at 45° C. for 96 h, C2:C3>20:1. The desired product 2a (95.6 mg, 78% yield) was obtained as a colorless oil after purification by silica gel flash chromatography (gradient elution, 2→3% CH$_2$Cl$_2$ in hexanes), Rf=0.4 (10% CH$_2$Cl$_2$ in hexanes); $^1$H NMR (500 MHz, CDCl$_3$) δ 7.70 (dt, J=7.9, 1.1 Hz, 1H), 7.40 (dq, J=8.3, 1.0 Hz, 1H), 7.30 (ddd, J=8.3, 7.0, 1.3 Hz, 1H), 7.16 (ddd, J=7.9, 6.9, 1.0 Hz, 1H), 6.81 (d, J=1.1 Hz, 1H), 3.90 (s, 3H), 1.13-1.05 (m, 9H), 1.03-0.95 (m, 6H); $^{13}$C NMR (125 MHz, CDCl$_3$) δ 140.4, 138.3, 128.7, 122.0, 120.7, 119.1, 113.1, 109.1, 33.1, 7.7, 4.2. IR (Neat Film, NaCl) 2953, 2909, 2874, 1492, 1464, 1415, 1372, 1356, 1299, 1233, 1166, 1101, 1069, 1007, 973, 797 cm$^{-1}$; HRMS (ESI+) calc'd for C$_{15}$H$_{24}$NSi [M+H]+: 246.1673, found 246.1674. The HSQC spectrum of this reaction product has previously been reported in U.S. Pat. No. 9,000,167.

This material was also made at scale as follows. A 500 mL oven-dried Schlenk flask equipped with a stir bar and stoppered with a rubber septum was evacuated and refilled once with argon. KOt-Bu (18.8 grams, 167.9 mmols, 20 mol %) was weighed out on the bench and added to the flask under a strong flow of argon. The charged flask was then evacuated and refilled with argon. 1-Methylindole (95% purity, AKSci, undistilled, yellow oil; 95.1 mL, 762.4 mmol, 1.0 equiv) and Et$_3$SiH (182.6 mL, 1142 mmol, 1.5 equiv), which were previously degassed, were added through the septum by syringe. The mixture was then cooled to −78° C. (dry ice/acetone) and evacuated/backfilled with argon for three cycles. The cooling bath was removed and the flask was allowed to warm to room temperature under a positive pressure of argon. The flask was then transferred to a heating mantle set at 45° C. and stirred for 72 hours. The flask with the resultant deep red-purple solution was removed from heating and allowed to cool to room temperature, diluted with anhydrous Et2O (50 mL) and filtered to remove solid residue. After the solvent was removed in vacuo, a stirbar was added and the transparent deep amber solution was stirred under high vacuum (100 millitorr) for several hours to remove remaining volatiles. The mixture was then subjected to distillation under vacuum. The desired product 2a was obtained as a pale yellow oil (141.88 g, 76% yield).

Example 6.9.2: 1-methyl-3-(triethylsilyl)-1H-indole

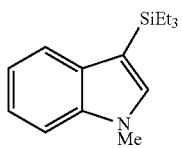

The reaction was conducted according to the General Procedure by heating N-methylindole (66 mg, 0.5 mmol, 1 equiv.), KOt-Bu (56 mg, 0.5 mmol, 1 equiv.) and Et$_3$SiH (88 microliters, 0.55 mmol, 1.1 equiv.) in 1 mL of tetrahydrofuran for 312 hours at 23° C. After aqueous work up, the crude reaction mixture was purified by chromatography on silica eluting with 95:5 hexanes:NEt$_3$ (isochratic) to obtain 103 mg (84%) of the title compound as a colourless oil. $^1$H NMR (500 MHz, THF-d8) δ 7.63 (dt, J=7.9, 1.0 Hz, 1H), 7.32 (dt, J=8.2, 0.9 Hz, 1H), 7.15 (s, 1H), 7.12 (ddd, J=8.2, 7.0, 1.1 Hz, 1H), 7.01 (ddd, J=8.0, 7.0, 1.1 Hz, 1H), 3.78 (s, 3H), 1.06-0.95 (m, 9H), 0.95-0.83 (m, 6H). $^{13}$C NMR (126 MHz, THF-d8) δ 138.63, 135.94, 133.37, 121.44, 120.88, 118.79, 108.96, 104.39, 31.61, 7.04, 4.11. The HSQC spectrum of this reaction product has previously been reported in U.S. Pat. No. 9,000,167.

Example 6.9.3: 1-methyl-3-(triethylsilyl)-1H-indole 2b

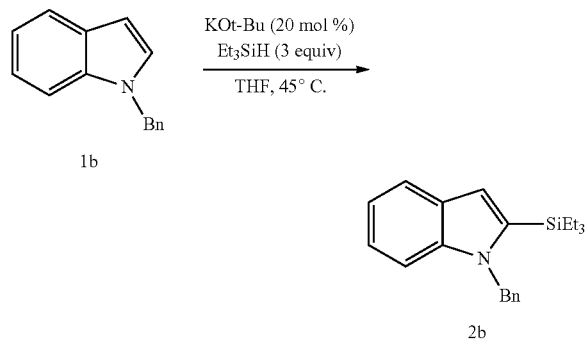

The reaction was conducted according to the General Procedure by heating KOt-Bu (11.2 mg, 0.1 mmol, 20 mol %), N-benzylindole 1b (103.5 mg, 0.5 mmol, 1 equiv), Et$_3$SiH (2.43 μL, 1.5 mmol, 3 equiv), and 0.5 mL of THF at 45° C. for 40 h. C2:C3>20:1. The desired product 2b (132.2 mg, 82% yield) was obtained as a colorless oil after purification by silica gel flash chromatography (10% CH$_2$Cl$_2$ in hexanes). Rf=0.3 (10% CH$_2$Cl$_2$ in hexanes); $^1$H NMR (500 MHz, CDCl$_3$) δ 7.81-7.77 (m, 1H), 7.38-7.29 (m, 3H), 7.26-7.19 (m, 3H), 7.02 (ddd, J=6.9, 2.2, 1.0 Hz, 2H), 6.97 (s, 1H), 5.59 (s, 2H), 1.08-1.04 (m, 9H), 0.94-0.89 (m, 6H); $^{13}$C NMR (125 MHz, CDCl$_3$) δ 140.2, 138.5, 138.3, 129.1, 128.7, 127.3, 125.9, 122.3, 120.7, 119.5, 114.1, 110.2, 50.2, 7.5, 4.0. IR (Neat Film, NaCl) 3060, 3029, 2954, 2909, 2875, 1606, 1495, 1466, 1452, 1416, 1377, 1353, 1333, 1300, 1238, 1196, 1164, 1115, 1096, 1014, 798, 734 cm$^{-1}$; HRMS (ESI+) calc'd for C21H28NSi [M+H]+: 322.1986, found 322.1985.

The reaction was conducted according to the General Procedure by heating 1-benzylindole (62 mg, 0.5 mmol, 1 equiv.), KOt-Bu (11 mg, 0.1 mmol, 0.2 equiv) and and Et$_3$SiH (239 microliters, 1.5 mmol, 3 equiv.) in 1 mL of tetrahydrofuran for 48 hours at 23° C. After aqueous work up, the crude reaction mixture was purified by chromatography on silica using hexanes (isochratic) to obtain 50 mg (31%) of the title compound as a colourless oily solid. $^1$H NMR (500 MHz, THF-d8) δ 7.56 (ddd, J=7.7, 1.3, 0.7 Hz, 1H), 7.25-7.07 (m, 4H), 7.02 (ddd, J=8.2, 6.9, 1.3 Hz, 1H), 6.98 (ddd, J=7.9, 6.9, 1.1 Hz, 1H), 6.92-6.86 (m, 2H), 6.80 (d, J=0.9 Hz, 1H), 5.52 (s, 2H), 1.06-0.88 (m, 9H), 0.85-0.69 (m, 6H).

Example 6.9.4: 1-Ethyl-2-(triethylsilyl)-1H-indole 2c

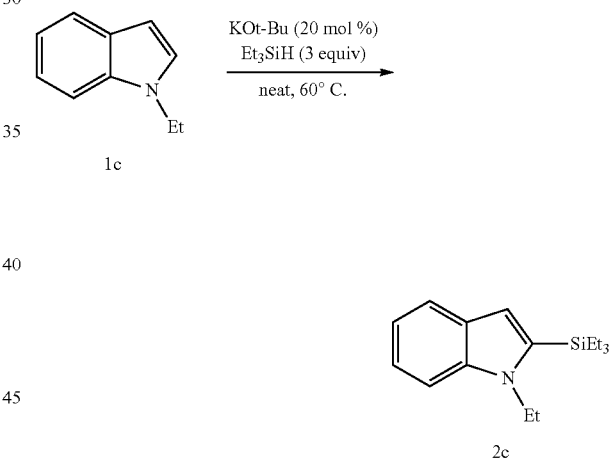

The reaction was conducted according to the General Procedure by heating KOt-Bu (11.2 mg, 0.1 mmol, 20 mol %), N-ethylindole 1c (72.5 mg, 0.5 mmol, 1 equiv), and Et$_3$SiH (243 μL, 1.5 mmol, 3 equiv) at 60° C. for 84 h. C2:C3>20:1. The desired product 2c (92.4 mg 71% yield) was obtained as a colorless oil after purification by silica gel flash chromatography (5% CH$_2$Cl$_2$ in hexanes). Rf=0.4 (10% CH$_2$Cl$_2$ in hexanes); $^1$H NMR (500 MHz, CDCl$_3$) δ 7.67 (dt, J=7.9, 0.9 Hz, 1H), 7.40 (dt, J=8.2, 0.9 Hz, 1H), 7.25 (ddd, J=8.2, 7.0, 1.2 Hz, 1H), 7.13 (ddd, J=7.9, 7.0, 1.0 Hz, 1H), 6.75 (d, J=1.0 Hz, 1H), 4.31 (q, J=7.2 Hz, 2H), 1.46 (t, J=7.2 Hz, 3H), 1.08-1.04 (m, 9H), 0.99-0.92 (m, 6H); $^{13}$C NMR (125 MHz, CDCl$_3$) δ 139.0, 137.4, 129.1, 121.7, 120.7, 119.0, 113.0, 109.4, 41.5, 15.5, 7.5, 4.0. IR (Neat Film, NaCl) 2953, 2909, 2874, 1491, 1466, 1416, 1378, 1347, 1335, 1299, 1218, 1165, 1090, 1069, 1012, 956, 900, 820, 787, 773, 750, 733 cm$^{-1}$; HRMS (MM: ESI-APCI+) calc'd for C$_{16}$H$_{26}$NSi [M+H]+: 260.1829, found 260.1829.

Example 6.9.5: 1-Phenyl-2-(triethylsilyl)-1H-indole 2d

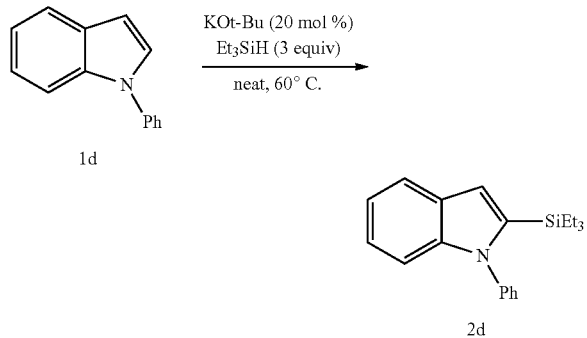

The reaction was conducted according to the General Procedure by heating KOt-Bu (7.4 mg, 0.07 mmol, 20 mol %), N-phenylindole 1d (63.2 mg, 0.33 mmol, 1 equiv), and Et$_3$SiH (160 μL, 1.0 mmol, 3 equiv) at 60° C. for 84 h. C2:C3>20:1. The desired product 2d (45.6 mg, 45% yield) was obtained as a white solid after purification by silica gel flash chromatography (3% CH$_2$Cl$_2$ in hexanes). Rf=0.5 (10% CH$_2$Cl$_2$ in hexanes); $^1$H NMR (500 MHz, CDCl$_3$) δ 7.74-7.67 (m, 1H), 7.58-7.47 (m, 3H), 7.44-7.36 (m, 2H), 7.21-7.12 (m, 2H), 7.12-7.05 (m, 1H), 6.93 (d, J=0.9 Hz, 1H), 0.92 (t, J=7.9 Hz, 9H), 0.68-0.55 (m, 6H); $^{13}$C NMR (125 MHz, CDCl$_3$) δ 141.6, 140.8, 139.1, 129.2, 128.8, 128.7, 128.3, 122.4, 120.5, 119.8, 114.9, 110.5, 7.5, 4.0. IR (Neat Film, NaCl) 3058, 2952, 2909, 2873, 1597, 1498, 1465, 1428, 1362, 1297, 1237, 1214, 1122, 1071, 1012, 976, 922, 820, 793, 736 cm$^{-1}$; HRMS (MM: ESI-APCI+) calc'd for C$_{20}$H$_{26}$NSi [M+H]+: 308.1829, found 308.1824.

Example 6.9.6: 1-(Methoxymethyl)-2-(triethylsilyl)-1H-indole 2e

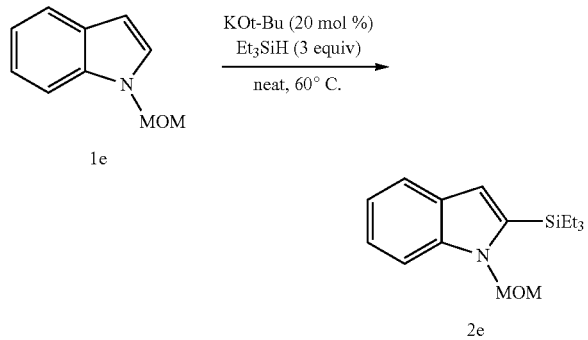

The reaction was conducted according to the General Procedure by heating KOt-Bu (11.2 mg, 0.1 mmol, 20 mol %), Nmethoxymethylindole 1e (80.5 mg, 0.5 mmol, 1 equiv) and Et$_3$SiH (243 μL, 1.5 mmol, 3 equiv) at 60° C. for 84 h. C2:C3=10:1. The desired product 2e (75.1 mg, 55% yield) was obtained as a colorless oil after purification by silica gel flash chromatography (3% EtOAc in hexanes). Rf=0.3 (5% EtOAc in hexanes); $^1$H NMR (500 MHz, CDCl$_3$) δ 7.67 (dt, J=7.8, 1.0 Hz, 1H), 7.53 (dq, J=8.3, 0.9 Hz, 1H), 7.28 (ddd, J=8.3, 7.0, 1.2 Hz, 1H), 7.17 (ddd, J=7.9, 7.0, 1.0 Hz, 1H), 6.86 (d, J=0.9 Hz, 1H), 5.55 (s, 2H), 3.30 (s, 3H), 1.10-1.01 (m, 9H), 1.01-0.92 (m, 6H); $^{13}$C NMR (125 MHz, CDCl$_3$) δ 140.7, 138.3, 129.2, 122.6, 120.8, 120.0, 115.6, 109.8, 76.8, 55.6, 7.5, 4.1. IR (Neat Film, NaCl) 2952, 2908, 2874, 1495, 1466, 1416, 1393, 1344, 1311, 1299, 1224, 1166, 1126, 1104, 1091, 1045, 1004, 961, 913, 797, 762, 735 cm$^{-1}$; HRMS (MM: ESI-APCI+) calc'd for C$_{16}$H$_{26}$NOSi [M+H]+: 276.1778, found 276.1769.

Example 6.9.7: 2-(Triethylsilyl)-1-((2-(trimethylsilyl)ethoxy)methyl)-1H-indole 2f

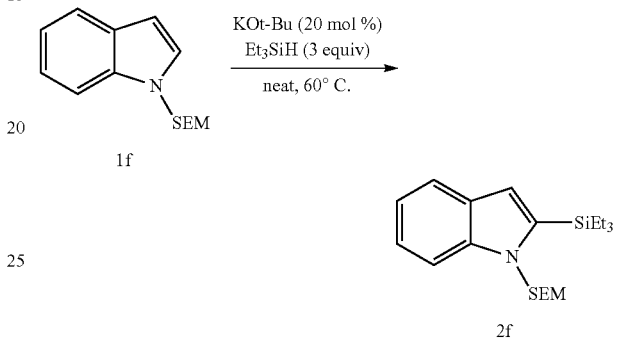

The reaction was conducted according to the General Procedure by heating KOt-Bu (11.2 mg, 0.1 mmol, 20 mol %), N-(2-trimethylsilyl-ethoxymethyl)-1H-indole 1f (123.5 mg, 0.5 mmol, 1 equiv) and Et$_3$SiH (243 μL, 1.5 mmol, 3 equiv) at 60° C. for 84 h, C2:C3>20:1. The desired product 2f (121.4 mg, 67% yield) was obtained as a colorless oil after purification by silica gel flash chromatography (15% CH$_2$Cl$_2$ in hexanes). Rf=0.2 (10% CH$_2$Cl$_2$ in hexanes); $^1$H NMR (500 MHz, CDCl$_3$) δ 7.62 (dt, J=7.8, 1.0 Hz, 1H), 7.50 (dq, J=8.3, 0.9 Hz, 1H), 7.24 (ddd, J=8.3, 7.0, 1.2 Hz, 1H), 7.12 (ddd, J=7.9, 7.0, 0.9 Hz, 1H), 6.80 (d, J=0.9 Hz, 1H), 5.54 (s, 2H), 3.54-3.48 (m, 2H), 1.04-0.98 (m, 9M, 0.96-0.90 (m, 8H), −0.02 (s, 9H); $^{13}$C NMR (125 MHz, CDCl$_3$) δ 140.5, 138.1, 129.1, 122.4, 120.7, 119.9, 115.3, 109.8, 75.2, 65.6, 18.1, 7.6, 4.0, −1.3. IR (Neat Film, NaCl) 2952, 2875, 1495, 1466, 1443, 1417, 1378, 1343, 1312, 1299, 1249, 1167, 1081, 1003, 972, 939, 894, 859, 836, 796, 760, 749, 734 cm$^{-1}$; HRMS (MM: ESI-APC+) calc'd for C$_{20}$H$_{36}$NOSi$_2$ [M+H]+: 362.2330, found 362.2340.

Example 6.9.8: Reaction of 4-methyl-N-methylindole with Et$_3$SiH

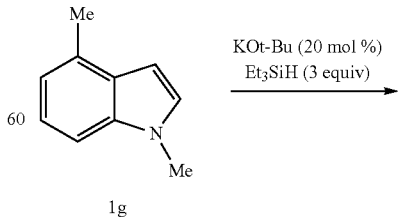

condition A: THF, 25° C., 120 h:
condition B: neat, 45° C., 84 h:

-continued

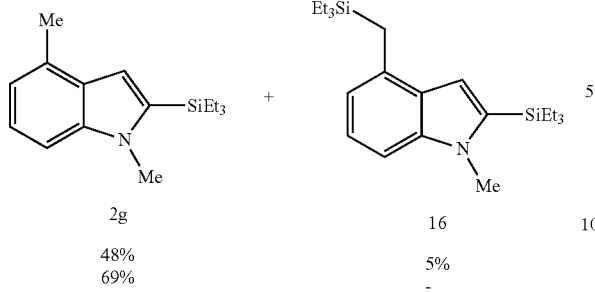

2g
48%
69%

16
5%
-

The reaction was conducted according to the General Procedure. For condition A: The reaction was performed with KOt-Bu (11.2 mg, 0.1 mmol, 20 mol %), 4-methyl-N-methylindole 1g (72.5 mg, 0.5 mmol, 1 equiv), Et$_3$SiH (243 µL, 1.5 mmol, 3 equiv), and 0.5 mL of THF at 25° C. for 120 h. C2:C3>20:1. The desired mono-silylation product 2g (61.8 mg, 48% yield) and bis-silylation 16 (9.7 mg, 5% yield) were obtained after purification by silica gel flash chromatography (gradient elution, 2→3% CH$_2$Cl$_2$ in hexanes). For condition B: The reaction was performed with KOt-Bu (11.2 mg, 0.1 mmol, 20 mol %), 4-methyl-Nmethylindole 1g (72.5 mg, 0.5 mmol, 1 equiv) and Et$_3$SiH (243 µL, 1.5 mmol, 3 equiv) at 45° C. for 84 h. C2:C3>20:1. Only mono silylation product 2g (89.7 mg, 69% yield) was formed and obtained after purification by silica gel flash chromatography (3% CH$_2$Cl$_2$ in hexanes).

1,4-Dimethyl-2-(triethylsilyl)-1H-indole 2g: Colorless oil; Rf=0.4 (10% CH$_2$Cl$_2$ in hexanes); $^1$H NMR (500 MHz, CDCl$_3$) δ 7.23-7.14 (m, 2H), 6.91 (dt, J=6.7, 1.0 Hz, 1H), 6.75 (d, J=0.9 Hz, 1H), 3.85 (s, 3H), 2.60 (s, 3H), 1.07-1.00 (m, 9H), 0.98-0.92 (m, 6H); $^{13}$C NMR (125 MHz, CDCl$_3$) δ 140.2, 137.6, 130.2, 128.6, 122.2, 119.4, 111.5, 106.8, 33.2, 18.8, 7.7, 4.3. IR (Neat Film, NaCl) 2953, 2910, 2874, 1586, 1502, 1454, 1415, 1366, 1323, 1280, 1238, 1160, 1140, 1077, 1004, 953, 765, 752, 735 cm$^{-1}$; HRMS (MM: ESI-APCI+) calc'd for C$_{16}$H$_{26}$NSi [M+H]+: 260.1829, found 260.1823.

1-Methyl-2-(triethylsilyl)-4-((triethylsilyl)methyl)-1H-indole 16: Colorless oil; Rf=0.4 (10% CH$_2$Cl$_2$ hexanes); $^1$H NMR (500 MHz, C6D6) δ 7.28 (dd, J=8.2, 7.1 Hz, 6.98 (d, J=8.3 Hz, 1H), 6.97-6.94 (m, 2H), 3.31 (s, 3H), 2.50 (s, 2H), 1.01 (t, J=7.8 Hz, 9H), 0.95 (t, J=7.9 Hz, 9H), 0.83 (q, J=7.8 Hz, 6H), 0.58 (q, J=7.9 Hz, 6H); $^{13}$C NMR (125 MHz, C6D6) δ 141.1, 136.0, 133.3, 122.8, 118.9, 113.0, 105.8, 32.9, 19.2, 7.7, 4.5, 4.1. IR (Neat Film, NaCl) 2952, 2909, 2874, 1579, 1498, 1454, 1443, 1414, 1359, 1322, 1285, 1237, 1151, 1070, 1008, 980, 774, 734 cm$^{-1}$; HRMS (EI+) calc'd for C$_{22}$H$_{39}$NSi$_2$ [M.+]: 373.2621, found 373.2624.

Example 6.9.9:
1,5-Dimethyl-2-(triethylsilyl)-1H-indole 2h

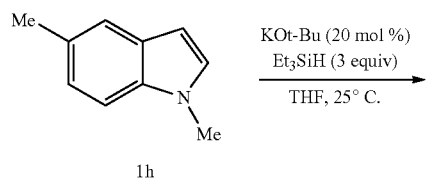

-continued

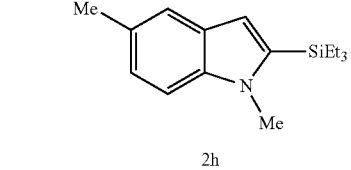

2h

The reaction was conducted according to the General Procedure by heating KOt-Bu (11.2 mg, 0.1 mmol, 20 mol %), 5-methyl-N-methylindole 1h (72.5 mg, 0.5 mmol, 1 equiv), Et$_3$SiH (243 µL, 1.5 mmol, 3 equiv), and 0.5 mL of THF at 25° C. for 96 h. C2:C3>20:1. The desired product 2h (88.7 mg, 68% yield) was obtained as a colorless oil after purification by silica gel flash chromatography (10% CH$_2$Cl$_2$ in hexanes). Rf=0.3 (10% CH$_2$Cl$_2$ in hexanes); $^1$H NMR (500 MHz, CDCl$_3$) δ 7.39 (s, 1H), 7.25-7.19 (m, 1H), 7.05 (dd, J=8.4, 1.6 Hz, 1H), 6.63 (d, J=0.8 Hz, 1H), 3.81 (s, 3H), 2.45 (s, 3H), 1.03-0.97 (m, 9H), 0.93-0.86 (m, 6H). $^{13}$C NMR (125 MHz, CDCl$_3$) δ 138.8, 138.3, 128.9, 128.3, 123.6, 120.2, 112.4, 108.8, 33.1, 21.5, 7.7, 4.1. IR (Neat Film, NaCl) 2952, 2909, 2873, 1505, 1456, 1358, 1321, 1236, 1181, 1104, 1069, 1003, 833, 788, 736 cm$^{-1}$; HRMS (ESI+) calc'd for C$_{16}$H$_{26}$NSi [M+H]+: 260.1826, found 260.1827.

Example 6.9.10: Reaction of 5-methyl-N methyl indole with Et$_3$SiH

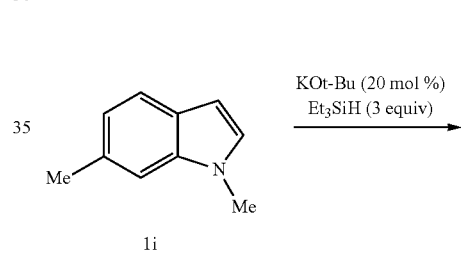

condition A: THF, 25° C., 120 h:
condition B: neat, 45° C., 84 h:

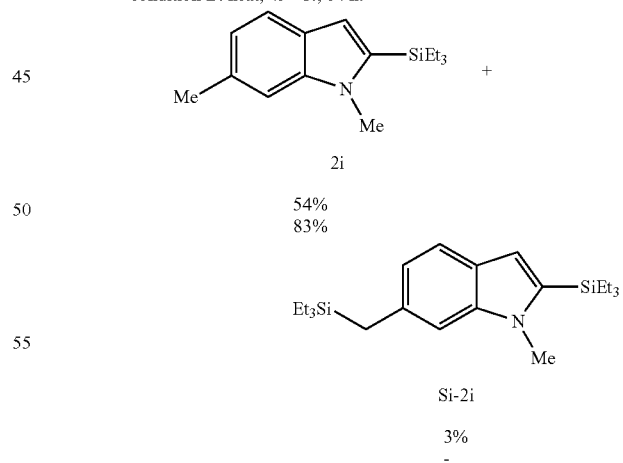

2i
54%
83%

Si-2i
3%
-

The reaction was conducted according to the General Procedure. For condition A: The reaction was performed with KOt-Bu (11.2 mg, 0.1 mmol, 20 mol %), 6-methyl-N-methylindole 1i (72.5 mg, 0.5 mmol, 1 equiv), Et$_3$SiH (243 µL, 1.5 mmol, 3 equiv), and 0.5 mL of THF at 25° C. for 120 h. C2:C3>20:1. The desired mono silylation product 2i (69.5 mg, 54% yield) and bis-silylation SI-2i (5.2 mg, 3% yield) were obtained after purification by silica gel flash chromatography (gradient elution, 2→3% CH$_2$Cl$_2$ in hexanes). For condition B: The reaction was performed with KOt-Bu (11.2 mg, 0.1 mmol, 20 mol %), 6-methyl-N-methylindole 1i (72.5 mg, 0.5 mmol, 1 equiv) and Et$_3$SiH (2.43 μL, 1.5 mmol, 3 equiv) at 45° C. for 84 h. C2:C3>20:1. Only mono silylation product 2i (108.1 mg, 83% yield) was formed and obtained after purification by silica gel flash chromatography (3% CH$_2$Cl$_2$ in hexanes).

1,6-Dimethyl-2-(triethylsilyl)-1H-indole 2i: Colorless oil; Rf=0.4 (10% CH$_2$O$_2$ in hexanes); $^1$H NMR (500 MHz, CDCl$_3$) δ 7.55 (d, J=8.0 Hz, 1H), 7.18 (s, 1H), 6.98 (ddd, J=8.0, 1.4, 0.7 Hz, 1H), 6.73 (d, J=0.9 Hz, 1H), 3.85 (s, 3H), 2.57 (s, 3H), 1.08-1.03 (m, 9H), 0.98-0.92 (m, 6H); $^{13}$C NMR (125 MHz, CDCl$_3$) δ 140.9, 137.6, 131.8, 126.7, 121.0, 120.3, 113.0, 109.1, 33.0, 22.0, 7.6, 4.2. IR (Neat Film, NaCl) 2953, 2910, 2874, 1617, 1480, 1451, 1413, 1376, 1360, 1333, 1296, 1233, 1065, 1003, 941, 808, 781, 736 cm$^{-1}$; HRMS (ESI+) calc'd for C$_{16}$H$_{26}$NSi [M+H]+: 260.1826, found 260.1823.

1-Methyl-2-(triethylsilyl)-6-((triethylsilyl)methyl)-1H-indole SI-2i: Colorless oil; Rf=0.4 (10% CH$_2$Cl$_2$ hexanes); $^1$H NMR (500 MHz, C6D6) δ 7.64 (dd, J=7.9, 0.8 Hz, 1H), 6.99-6.93 (m, 2H), 6.81 (d, J=0.9 Hz, 1H), 3.41 (s, 3H), 2.31 (s, 2H), 1.02-0.93 (m, 18H), 0.79 (q, J=7.7 Hz, 6H), 0.58 (q, J=7.9 Hz, 6H); $^{13}$C NMR (125 MHz, C6D6) δ 141.9, 136.3, 134.6, 126.7, 121.2, 120.9, 114.0, 108.3, 32.7, 22.4, 7.8, 7.7, 4.5, 3.7. IR (Neat Film, NaCl) 2952, 2909, 2874, 1615, 1568, 1479, 1463, 1414, 1361, 1336, 1319, 1299, 1234, 1195, 1157, 1090, 1065, 1009, 948, 842, 817, 787, 771, 736 cm$^{-1}$; HRMS (EI+) calc'd for C$_{22}$H$_{39}$NSi$_2$ [M.+]: 373.2621, found 373.2609.

Example 6.9.11:
1,7-Dimethyl-2-(triethylsilyl)-1H-indole 2j

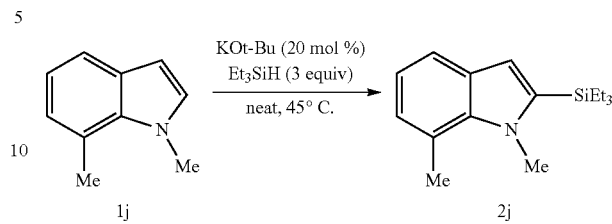

The reaction was conducted according to the General Procedure by heating KOt-Bu (11.2 mg, 0.1 mmol, 20 mol %), 7-methyl-Nmethylindole 1j (72.5 mg, 0.5 mmol, 1 equiv) and Et$_3$SiH (243 μL, 1.5 mmol, 3 equiv) at 45° C. for 84 h. C2:C3>20:1. The desired product 2j (78.9 mg, 61% yield) was obtained as a colorless oil after purification by silica gel flash chromatography (3% CH$_2$Cl$_2$ in hexanes). Rf=0.4 (10% CH$_2$Cl$_2$ in hexanes); $^1$H NMR (500 MHz, CDCl$_3$) δ 7.43 (d, J=7.7 Hz, 1H), 6.94-6.87 (m, 2H), 6.66 (s, 1H), 4.11 (s, 3H), 2.80 (s, 3H), 1.03-0.97 (m, 9H), 0.92-0.85 (m, 6H); $^{13}$C NMR (125 MHz, CDCl$_3$) δ 139.2, 139.1, 129.7, 125.0, 121.0, 119.4, 119.0, 113.6, 36.8, 20.6, 7.7, 4.2. IR (Neat Film, NaCl) 2953, 2909, 2873, 1503, 1459, 1415, 1396, 1377, 1358, 1340, 1315, 1304, 1238, 1156, 1113, 1086, 1063, 1004, 861, 798, 742 cm$^{-1}$; HRMS (ESI+) calc'd for C$_{16}$H$_{26}$NSi [M+H]+: 260.1826, found 260.1828.

Example 6.9.12: Reaction of
N-methyl-5-methoxyindole 1k with Et$_3$SiH

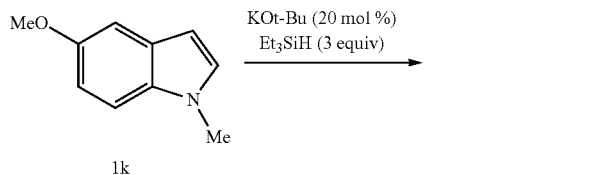

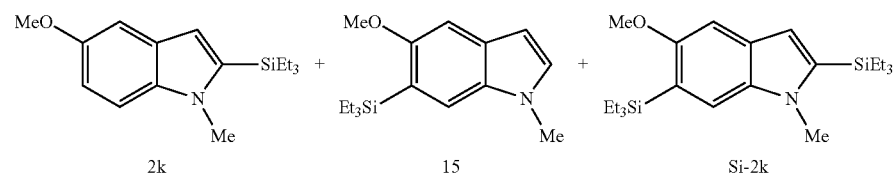

| | 2k | 15 | Si-2k |
|---|---|---|---|
| condition A: THF, 25° C., 120 h: | 43% | 9% | 22% |
| condition B: THF, 25° C., 72 h: | 64% | - | - |

The reaction was conducted according to the General Procedure. For condition A: The reaction was performed with KOt-Bu (11.2 mg, 0.1 mmol, 20 mol %), N-methyl-5-methoxyindole 1k (80.7 mg, 0.5 mmol, 1 equiv), Et₃SiH (243 μL, 1.5 mmol, 3 equiv), and 0.5 mL of THF at 25° C. for 120 h. C2:C3>20:1. The C2-silylation product 2k (58.7 mg, 43% yield), C6-silylation product 15 (12.5 mg, 9% yield), and bis-silylation product SI-2k (42.9 mg, 22% yield), were obtained after purification by silica gel flash chromatography (gradient elution, 5→10→25% CH₂Cl₂ in hexanes). For condition B: The reaction was performed with KOt-Bu (11.2 mg, 0.1 mmol, 20 mol %), N-methyl-5-methoxyindole 1k (80.5 mg, 0.5 mmol, 1 equiv), Et₃SiH (243 μL, 1.5 mmol, 3 equiv), and 0.5 mL of THF at 25° C. for 72 h. C2:C3>20:1. The desired product 2k (87.6 mg, 64% yield) was obtained after purification by silica gel flash chromatography (gradient elution, 5→10→25% CH₂Cl₂ in hexanes) and a minor amount (<5%) of byproducts were observed.

5-Methoxy-1-methyl-2-(triethylsilyl)-1H-indole 2k: White solid; Rf=0.2 (33% CH₂Cl₂ in hexanes); $^1$H NMR (500 MHz, CDCl₃) δ 7.21 (s, 1H), 7.07 (d, J=2.4 Hz, 1H), 6.89 (dd, J=8.8, 2.5 Hz, 1H), 6.63 (d, J=0.8 Hz, 1H), 3.85 (s, 3H), 3.81 (s, 3H), 1.03-0.96 (m, 9H), 0.93-0.86 (m, 6H); $^{13}$C NMR (125 MHz, CDCl₃) δ 154.0, 139.0, 135.9, 128.8, 112.6, 112.3, 109.8, 102.0, 56.1, 33.2, 7.7, 4.1. IR (Neat Film, NaCl) 2950, 2909, 2872, 1503, 1450, 1413, 1334, 1237, 1208, 1173, 1147, 1102, 1072, 1027, 997, 843, 801, 735, 716 cm$^{-1}$; HRMS (ESI+) calc'd for C₁₆H₂₆NOSi [M+H]+: 276.1778, found 276.1776.

5-Methoxy-1-methyl-2,6-bis(triethylsilyl)-1H-indole SI-2k: White solid, Rf=0.6 (33% CH₂Cl₂ in hexanes); $^1$H NMR (500 MHz, CDCl₃) δ 7.30 (s, 1H), 7.01 (s, 1H), 6.64 (d, J=0.8 Hz, 1H), 3.85 (s, 3H), 3.83 (s, 3H), 1.06-0.97 (m, 18H), 0.95-0.86 (m, 12H); $^{13}$C NMR (125 MHz, CDCl₃) δ 159.1, 138.9, 136.1, 130.1, 120.8, 116.3, 112.2, 99.7, 55.5, 33.2, 7.9, 7.7, 4.3, 4.1. IR (Neat Film, NaCl) 2952, 2874, 2908, 1608, 1556, 1475, 1454, 1407, 1363, 1337, 1236, 1205, 1172, 1144, 1123, 1072, 1004, 971, 837 cm$^{-1}$; HRMS (ESI+) calc'd for C₂₂H₄₀NOSi₂ [M+H]+: 390.2643, found 390.2632.

5-Methoxy-1-methyl-6-(triethylsilyl)-1H-indole 15: Colorless oil; Rf=0.4 (33% CH₂Cl₂ in hexanes); $^1$H NMR (500 MHz, CDCl₃) δ 7.27 (s, 1H), 7.01 (s, 1H), 7.00 (d, J=3.0 Hz, 1H), 6.38 (dd, J=3.0, 0.8 Hz, 1H), 3.82 (s, 3H), 3.78 (s, 3H), 1.00-0.94 (m, 9H), 0.91-0.83 (m, 6H); $^{13}$C NMR (125 MHz, CDCl₃) δ 159.2, 132.5, 130.1, 129.3, 120.2, 116.5, 100.4, 100.3, 55.5, 33.0, 7.9, 4.1. IR (Neat Film, NaCl) 2950, 2908, 2873, 1612, 1554, 1505, 1471, 1414, 1310, 1268, 1231, 1190, 1148, 1123, 1059, 1017, 984, 831 cm$^{-1}$; HRMS (ESI+) calc'd for C₁₆H₂₆NOSi [M+H]+: 276.1778, found 276.1765.

Example 6.9.13: 5-(Benzyloxy)-1-methyl-2-(triethylsilyl)-1H-indole 2l

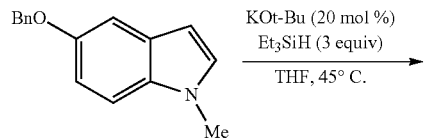

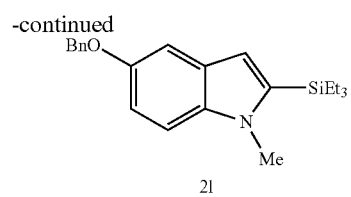

The reaction was conducted according to the General Procedure by heating KOt-Bu (11.2 mg, 0.1 mmol, 20 mol %), N-methyl-5-benzyloxyindole 1l (118.5 mg, 0.5 mmol, 1 equiv), Et₃SiH (243 μL, 1.5 mmol, 3 equiv), and 0.5 mL of THF at 45° C. for 64 h. C2:C3>20:1. The desired product 2l (119.4 mg, 68% yield) was obtained as a yellow solid after purification by silica gel flash chromatography (25% CH₂Cl₂ in hexanes). Rf=0.4 (5% EtOAc in hexanes). $^1$H NMR (500 MHz, CDCl₃) δ 7.48 (d, J=7.0 Hz, 2H), 7.41-7.36 (m, 2H), 7.35-7.29 (m, 1H), 7.22 (d, J=8.9 Hz, 1H), 7.14 (d, J=2.4 Hz, 1H), 6.97 (dd, J=8.8, 2.4 Hz, 1H), 6.62 (d, J=0.8 Hz, 1H), 5.11 (s, 2H), 3.81 (s, 3H), 1.04-0.96 (m, 9H), 0.96-0.84 (m, 6H); $^{13}$C NMR (125 MHz, CDCl₃) δ 153.3, 139.1, 138.1, 136.2, 129.0, 128.6, 127.8, 127.6, 113.4, 112.5, 109.8, 104.0, 71.3, 33.2, 7.6, 4.2. IR (Neat Film, NaCl) 2951, 2908, 2872, 1492, 1452, 1422, 1336, 1288, 1237, 1192, 1150, 1102, 1075, 1018, 840, 812, 751, 735 cm$^{-1}$; HRMS (MM: ESI-APCI+) calc'd for C₂₂H₃₀NOSi [M+H]+: 352.2091, found 352.2093.

Example 6.9.14: Reaction of 5-(methoxymethyl)-1N-methylindole 1m with Et₃SiH

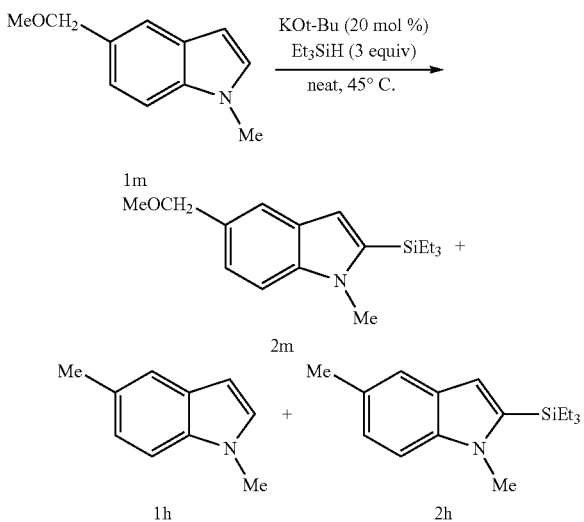

The reaction was conducted according to the General Procedure by heating KOt-Bu (11.2 mg, 0.1 mmol, 20 mol %), 5-(methoxymethyl)-N-methylindole 1m (87.5 mg, 0.5 mmol, 1 equiv) and Et₃SiH (243 μL, 1.5 mmol, 3 equiv) at 45° C. for 84 h. C2:C3>20:1. The desired product 2m (69.3 mg, 48% yield), byproducts 1h (2.5 mg, 2% yield) and 2h (11.3 mg, 9% yield) were obtained after purification by silica gel flash chromatography (gradient elution, 25→50% CH₂Cl₂ in hexanes).

5-(Methoxymethyl)-1-methyl-2-(triethylsilyl)-1H-indole 2m: Colorless oil, Rf=0.4 (50% CH₂Cl₂ in hexanes); $^1$H NMR (500 MHz, CDCl$_3$) δ 7.59 (d, J=0.8 Hz, 1H), 7.33 (d, J=8.4 Hz, 1H), 7.25 (d, J=8.4 Hz, 1H), 6.73 (d, J=0.8 Hz, 1H), 4.59 (s, 2H), 3.85 (s, 3H), 3.38 (s, 3H), 1.06-0.99 (m, 9H), 0.96-0.90 (m, 6H); $^{13}$C NMR (125 MHz, CDCl$_3$) δ 140.0, 138.9, 128.8, 128.5, 122.6, 120.5, 113.0, 109.1, 75.6, 57.6, 33.2, 7.6, 4.1. IR (Neat Film, NaCl) 2952, 2873, 2817, 1504, 1455, 1415, 1357, 1324, 1297, 1236, 1188, 1153, 1137, 1094, 1069, 1004, 971, 878, 840, 798, 783, 726 cm$^{-1}$; HRMS (ESA+) calc'd for C$_{17}$H$_{28}$NOSi [M+H]+: 290.1935, found 290.1948.

Example 6.9.15:
1-Methyl-5-phenyl-2-(triethylsilyl)-1H-indole 2n

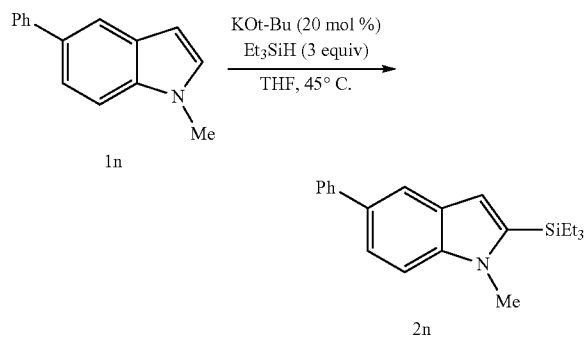

The reaction was conducted according to the General Procedure by heating KOt-Bu (11.2 mg, 0.1 mmol, 20 mol %), 5-phenyl-N-methylindole 1n (103.5 mg, 0.5 mmol, 1 equiv), Et$_3$SiH (243 μL, 1.5 mmol, 3 equiv), and 0.5 mL of THF at 45° C. for 108 h. C2:C3>20:1. The desired product 2n (77.8 mg, 48% yield) was obtained as a white solid after purification by silica gel flash chromatography (gradient elution, 5→10% CH$_2$Cl$_2$ in hexanes). Rf=0.3 (10% CH$_2$Cl$_2$ in hexanes); $^1$H NMR (500 MHz, CDCl$_3$) δ 7.90 (s, 1H), 7.72 (d, J=7.6 Hz, 2H), 7.55 (d, J=8.5 Hz, 1H), 7.53-7.47 (m, 2H), 7.44 (d, J=8.5 Hz, 1H), 7.37 (t, J=7.4 Hz, 1H), 6.85 (s, 1H), 3.91 (s, 3H), 1.09 (t, J=7.8 Hz, 9H), 1.03-0.95 (m, 6H); $^{13}$C NMR (125 MHz, CDCl$_3$) δ 142.9, 140.0, 139.3, 132.8, 129.2, 128.7, 127.5, 126.3, 122.0, 119.2, 113.5, 109.4, 33.2, 7.6, 4.2. IR (Neat Film, NaCl) 2950, 2908, 2873, 1600, 1485, 1455, 1361, 1325, 1301, 1214, 1162, 1074, 1004, 1086, 887, 820, 807, 787, 759, 733 cm$^{-1}$; HRMS (MM: ESI-APCI+) calc'd for C$_{21}$H$_{28}$NSi [M+H]+: 322.1986, found 322.1984.

Example 6.9.16: Reaction of N-methylindole 1a with Et$_2$SiH$_2$

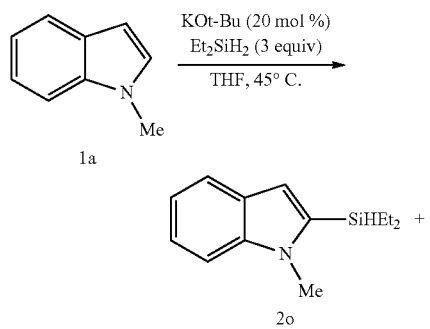

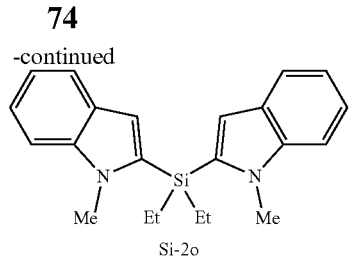

The reaction was conducted according to the General Procedure by heating KOt-Bu (11.2 mg, 0.1 mmol, 20 mol %), N-methylindole 1a (65.5 mg, 0.5 mmol, 1 equiv), Et$_2$SiH$_2$ (194 μL, 1.5 mmol, 3 equiv), and 0.5 mL of THF at 45° C. for 72 h. C2:C3>20:1. The silylation product 2o (73.4 mg, 68% yield) and a minor bisindotyl silane byproduct SI-2o were obtained after purification by silica gel flash chromatography (gradient elution, 1→2→5% CH$_2$Cl$_2$ in hexanes).

2-(Diethylsilyl)-1-methyl-1H-indole 2o: Colorless oil; Rf=0.4 (10% CH$_2$Cl$_2$ in hexanes); $^1$H NMR (500 MHz, CDCl$_3$) δ 7.66 (dt, J=7.9, 1.0 Hz, 1H), 7.37 (dt, J=8.3, 1.1 Hz, 1H), 7.28-7.25 (m, 1H), 7.16-7.09 (m, 1H), 6.79 (d, J=0.9 Hz, 1H), 4.50-4.43 (m, 1H), 3.88 (s, 3H), 1.14-1.06 (m, 6H), 1.00-0.93 (m, 4H); $^{13}$C NMR (125 MHz, CDCl$_3$) δ 140.2, 136.6, 128.6, 122.2, 120.8, 119.3, 112.8, 109.3, 32.8, 8.4, 3.7. IR (Neat Film, NaCl) 2954, 2908, 2872, 2110, 1492, 1464, 1412, 1371, 1357, 1327, 1301, 1233, 1166, 1101, 1071, 1009, 974, 987, 815, 785 cm$^{-1}$; HRMS (MM: ESI-APCI+) calc'd for C13H20NSi. [M+H]+: 218.1360, found 218.1354.

Diethylbis(1-methyl-1H-indol-2-yl)silane SI-2o: Colorless oil; Rf=0.2 (10% CH$_2$Cl$_2$ in hexanes); $^1$H NMR (500 MHz, CDCl$_3$) δ 7.68 (dt, J=7.9, 1.0 Hz, 2H), 7.31 (dt, J=8.3, 1.0 Hz, 2H), 7.25 (ddd, J=8.2, 6.9, 1.2 Hz, 2H), 7.13 (ddd, J=7.9, 6.9, 1.1 Hz, 2H), 6.92 (d, J=0.9 Hz, 2H), 3.57 (s, 6H), 1.31 (q, J=8.4 Hz, 4H), 1.07 (t, J 7.9 Hz, 6H); $^{13}$C NMR (125 MHz, CDCl$_3$) δ 140.7, 136.5, 128.7, 122.5, 120.9, 119.4, 113.8, 109.4, 32.7, 7.5, 4.5. IR (Neat Film, NaCl) 2955, 2874, 1492, 1463, 1414, 1355, 1327, 1299, 1233, 1166, 1101, 1072, 1008, 799, 751 cm$^{-1}$; HRMS (MM: ESI-APCI+) calc'd for C$_{22}$H$_{27}$N$_2$Si [M+H]+: 347.1938, found 347.1934.

Example 6.9.17:
1-Benzyl-2-(diethylsilyl)-1H-indole 2p

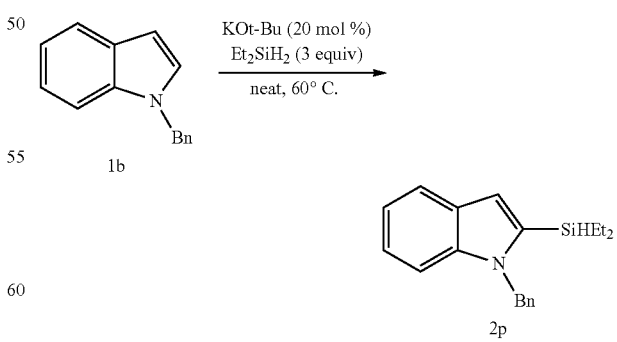

The reaction was conducted according to the General Procedure by heating KOt-Bu (11.2 mg, 0.1 mmol, 20 mol %), N-benzyl indole 1b (103.5 mg, 0.5 mmol, 1 equiv) and Et$_2$SiH$_2$ (194 μL, 1.5 mmol, 3 equiv) at 60° C. for 72 h.

C2:C3>20:1. The desired product 2p (114.1 mg, 78% yield) was obtained as a colorless oil after purification by silica gel flash chromatography (5% CH$_2$cl$_2$ in hexanes). Rf=0.5 (25% CH$_2$Cl$_2$ in hexanes); $^1$H NMR (500 MHz, CDC$_3$) δ 7.75 (dt, J=7.7, 1.0 Hz, 1H), 7.36-7.26 (m, 4H), 7.26-7.15 (m, 2H), 7.07-7.01 (m, 2H), 6.94 (d, J=0.9 Hz, 1H), 5.56 (s, 2H), 4.44 (p, J=3.3 Hz, 1H), 1.12-1.03 (m, 6H), 0.94-0.79 (m, 4H). $^{13}$C NMR (125 MHz, CDCl$_3$) δ 140.1, 138.5, 136.7, 129.0, 128.7, 127.4, 126.1, 122.5, 120.8, 119.6, 113.7, 110.1, 49.8, 8.3, 3.6. IR (Neat Film, NaCl) 2954, 2873, 2114, 1605, 1494, 1466, 1450, 1413, 1353, 1334, 1301, 1233, 1198, 1164, 1116, 1095, 972, 815 cm$^{-1}$; HRMS (MM: ESI-APCI+) calc'd for C$_{19}$H$_{24}$NSi [M+H]+: 294.1673, found 294.1668.

Example 6.9.18:
2-(Diethylsilyl)-1-phenyl-1H-indole 2g

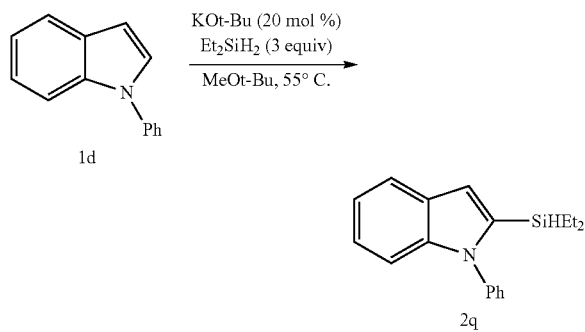

The reaction was conducted according to the General Procedure by heating KOt-Bu (11.2 mg, 0.1 mmol, 20 mol %), N-phenyl indole 1d (96.5 mg, 0.5 mmol, 1 equiv), Et$_2$SiH$_2$ (194 μL, 1.5 mmol, 3 equiv), and 0.5 mL of MeOt-Bu at 55° C. for 96 h. C2:C3>20:1. The desired product 2q (76.9 mg, 55% yield) was obtained as a yellow oil after purification by silica gel flash chromatography (10% CH$_2$Cl$_2$ in hexanes). Rf=0.6 (10% CH$_2$Cl$_2$ in hexanes); $^1$H NMR (500 MHz, CDCl$_3$) δ 7.76-7.74 (m, 1H), 7.60-7.55 (m, 2H), 7.53-7.47 (m, 3H), 7.30-7.17 (m, 3H), 7.03 (d, J=0.9 Hz, 1H), 4.30 (p, J=3.3 Hz, 1H), 1.02-0.98 (m, 6H), 0.79-0.63 (m, 4H); $^{13}$C NMR (125 MHz, CDCl$_3$) δ 141.1, 140.3, 137.1, 129.4, 128.8, 128.1, 128.0, 122.8, 120.7, 120.1, 115.1, 110.5, 8.2, 3.4. IR (Neat Film, NaCl) 3058, 2953, 2872, 2117, 1597, 1498, 1466, 1433, 1415, 1363, 1300, 1215, 1202, 1146, 1121, 1072, 1013, 978, 921, 902, 823, 759, 748, 737 cm$^{-1}$, HRMS (MM: ESI-APCI+) calc'd for C$_{18}$H$_{22}$NSi [M+H]+: 280.1516, found 280.1515.

Example 6.9.19:
2-(Diethylsilyl)-1-(methoxymethyl)-1H-indole 2r

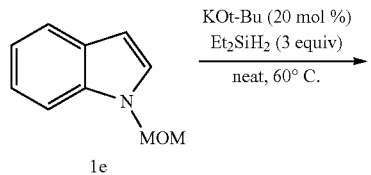

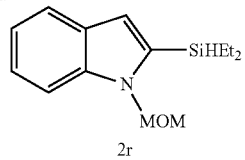

The reaction was conducted according to the General Procedure by heating KOt-Bu (11.2 mg, 0.1 mmol, 20 mol %), N-methoxymethylindole 1e (80.5 mg, 0.5 mmol, 1 equiv) and Et$_2$SiH$_2$ (193 μL, 1.5 mmol, 3 equiv) at 60° C. for 96 h. C2:C3>20:1. The desired product 2r (81.0 mg, 66% yield) was obtained as a colorless oil after purification by silica gel flash chromatography (3% EtOAc in hexanes). Rf=0.3 (5% EtOAc in hexanes); $^1$H NMR (500 MHz, CDCl$_3$) δ 7.67 (dt, J=7.9, 1.0 Hz, 1H), 7.54 (ddd, J=8.3, 2.0, 0.9 Hz, 1H), 7.29 (ddd, J=8.3, 7.0, 1.2 Hz, 1H), 7.18 (ddd, J=7.9, 7.0, 1.0 Hz, 1H), 6.88 (d, J=0.9 Hz, 1H), 5.60 (s, 2H), 4.49 (p, J=3.3 Hz, 1H), 3.29 (s, 3H), 1.14-1.08 (m, 6H), 1.03-0.94 (m, 4H); $^{13}$C NMR (125 MHz, CDCl$_3$) δ 140.4, 136.6, 129.2, 122.8, 120.9, 120.2, 115.1, 109.9, 76.6, 55.6, 8.3, 3.8. IR (Neat Film, NaCl) 2954, 2874, 2819, 2115, 1496, 1467, 1443, 1413, 1393, 1360, 1344, 1314, 1300, 1282, 1226, 1190, 1166, 1127, 1102, 1091, 1047, 1009, 974, 914, 896, 818, 749, 736 cm$^{-1}$; HRMS (MM: ESI-APCI+) calc'd for C$_{14}$H$_{22}$NOSi [M+H]+: 248.1465, found 248.1459.

Example 6.9.20: 2-(Diethylsilyl)-1-((2-(trimethylsilyl)ethoxy)methyl)-1H-indole 2s

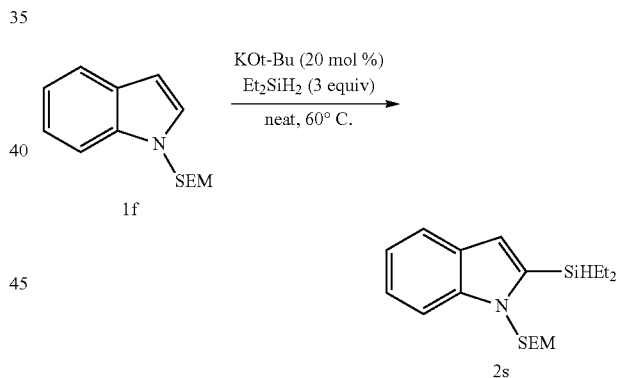

The reaction was conducted according to the General Procedure by heating KOt-Bu (11.2 mg, 0.1 mmol, 20 mol %), N-(2-trimethylsilyl-ethoxymethyl)-1H-indole 1f (123.5 mg, 0.5 mmol, 1 equiv) and Et$_2$SiH$_2$ (194 μL, 1.5 mmol, 3 equiv) at 60° C. for 84 h. C2:C3>20:1. The desired product 2s (106.7 mg, 64% yield) was obtained after purification by silica gel flash chromatography (14% CH$_2$Cl$_2$ in hexanes) as a colorless oil. Rf=0.2 (10% CH$_2$Cl$_2$ in hexanes); $^1$H NMR (500 MHz, CDCl$_3$) δ 7.65 (dt, J=7.9, 1.0 Hz, 1H), 7.53 (dt, J=8.3, 0.9 Hz, 1H), 7.27 (ddd, J=8.3, 7.0, 1.2 Hz, 1H), 7.15 (ddd, J=7.9, 7.0, 0.9 Hz, 1H), 6.84 (d, J=0.8 Hz, 1H), 5.61 (s, 2H), 4.48 (p, J=3.3 Hz, 1H), 3.55-3.48 (m, 2H), 1.14-1.04 (m, 6H), 1.03-0.88 (m, 6H), −0.02 (s, 9H); $^{13}$C NMR (125 MHz, CDCl$_3$) δ 140.2, 136.5, 129.1, 122.7, 120.8, 120.1, 114.7, 110.1, 75.0, 65.6, 18.0, 8.4, 3.7, −1.3. IR (Neat Film, NaCl) 2953, 2874, 2116, 1496, 1466, 1443, 1413, 1379, 1343, 1318, 1300, 1249, 1219, 1165, 1081, 1010, 974, 922, 895, 859, 835, 748, 735 cm$^{-1}$; HRMS (MM: ESIAPCI+) calc'd for C$_{18}$H$_{32}$NOSi$_2$ [M+H]+: 334.2017, found 334.2028.

Example 6.9.21:
2-(Diethylsilyl)-1,3-dimethyl-1H-indole 2t

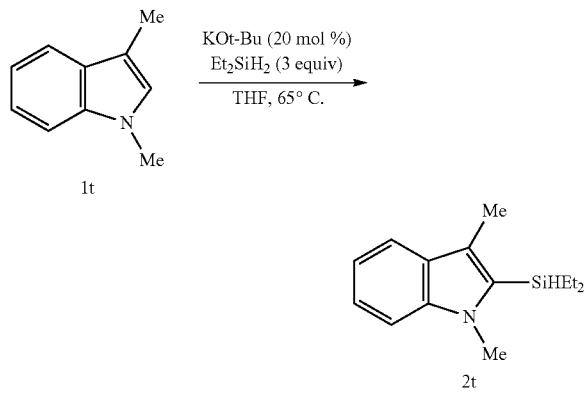

The reaction was conducted according to the General Procedure by heating KOt-Bu (11.2 mg, 0.1 mmol, 20 mol %), 1,3-dimethyl-1H-indole 1t (72.6 mg, 0.5 mmol, 1 equiv), Et$_2$SiH$_2$ (193 μL, 1.5 mmol, 3 equiv), and 0.5 mL of THF at 65° C., for 120 h. The desired product 2t (84.2 mg, 65% yield) was obtained as a colorless oil after purification by silica gel flash chromatography (100% hexanes). Rf=0.6 (100% hexanes); $^1$H NMR (500 MHz, C6D6) δ 7.67 (d, J=7.9 Hz, 1H), 7.30 (dd, J=8.3, 6.9 Hz, 1H), 7.22 (t, J=7.4 Hz, 1H), 7.10 (d, J=8.2 Hz, 1H), 4.59 (p, J=3.7 Hz, 1H), 3.31 (s, 3H), 2.46 (s, 3H), 0.98 (t, J=7.8 Hz, 6H), 0.77 (qd, J=7.9, 3.9 Hz, 4H); $^{13}$C NMR (125 MHz, C6D6) δ 140.6, 131.5, 129.8, 122.7, 122.3, 119.4, 119.0, 109.4, 32.4, 10.9, 8.8, 4.7. IR (Neat Film, NaCl) 2952, 2871, 2125, 1509, 1460, 1351, 1317, 1237, 1167, 1138, 1011, 975, 839, 803, 737 cm$^{-1}$; HRMS (EI+) calc'd for C$_{14}$H$_{21}$NSi [M.+]: 231.1443, found 231.1446.

Example 6.9.22:
2-(Ethyldimethylsilyl)-1-methyl-1H-indole 2u

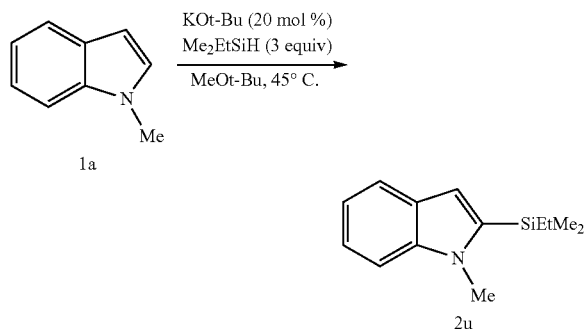

The reaction was conducted according to the General Procedure by heating KOt-Bu (11.2 mg, 0.1 mmol, 20 mol %), N-methylindole 1a (66.8 mg, 0.5 mmol, 1 equiv), EtMe$_2$SiH (197 μL, 1.5 mmol, 3 equiv) and 0.5 mL of MeOt-Bu at 45° C. for 120 h. C2:C3>20:1. The desired product 2u (58.5 mg, 54% yield) was obtained as a colorless oil after purification by silica gel flash chromatography (3% CH$_2$Cl$_2$ in hexanes). Rf=0.4 (10% CH$_2$Cl$_2$ in hexanes); $^1$H NMR (500 MHz, CDCl$_3$) δ 7.67 (dt, J=7.8, 1.0 Hz, 1H), 7.37 (dd, J=8.3, 0.9 Hz, 1H), 7.28 (ddd, J=8.2, 6.9, 1.1 Hz, 1H), 7.14 (ddd, J=7.9, 6.9, 1.0 Hz, 1H), 6.77 (d, J=0.9 Hz, 1H), 3.89 (s, 3H), 1.11-1.02 (m, 3H), 0.95-0.90 (m, 2H), 0.43 (s, 6H); $^{13}$C NMR (125 MHz, CDCl$_3$) δ 140.3, 140.2, 128.5, 122.1, 120.7, 119.2, 112.0, 109.1, 33.1, 7.8, 7.6, −2.6 IR (Neat Film, NaCl) 2954, 2908, 2873, 1492, 1464, 1418, 1356, 1326, 1300, 1249, 1233, 1166, 1131, 1101, 1071, 1007, 958, 897, 821 cm$^{-1}$; HRMS (MM: ESI-APCI+) calc'd for C$_{13}$H$_{19}$NSi [M+H]+: 217.1280; measured 217.1287.

This product was also prepared by heating N-methylindole 1a (62 mg, 0.5 mmol, 1 equiv.), KOt-Bu (11 mg, 0.1 mmol, 0.2 equiv) and EtMe$_2$SiH (198 microliters, 1.5 mmol, 3 equiv.) in 1 mL of tetrahydrofuran for 48 hours at 23° C. After aqueous work up, the crude reaction mixture was purified by chromatography on silica using hexanes (isochratic) to obtain 80 mg (74%) of the title compound as a colourless oil. $^1$H NMR (500 MHz, THF-d8) δ 7.48 (d, J=7.9 Hz, 1H), 7.31 (dd, J=8.4, 1.0 Hz, 1H), 7.10 (ddd, J=8.2, 6.9, 1.2 Hz, 1H), 6.95 (ddd, J=7.9, 6.9, 0.9 Hz, 1H), 6.64 (d, J=0.9 Hz, 1H), 3.84 (s, 3H), 1.05-0.95 (m, 3H), 0.89 (d, J=7.9 Hz, 2H), 0.38 (s, 6H). $^{13}$C NMR (126 MHz, THF-d8) δ 140.45, 138.94, 128.58, 121.45, 120.10, 118.51, 113.53, 111.90, 108.67, 32.17, 7.37, 6.77, −3.67.

Example 6.9.23:
1-Benzyl-2-(ethyldimethylsilyl)-1H-indole 2v

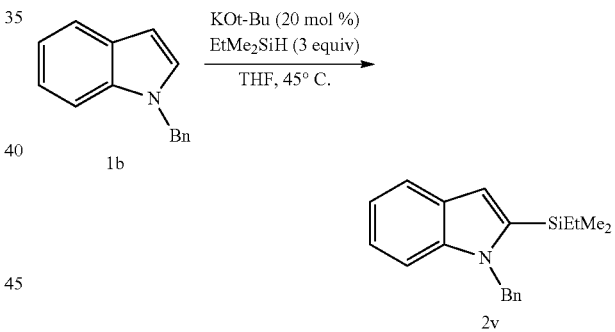

The reaction was conducted according to the General Procedure by heating KOt-Bu (11.2 mg, 0.1 mmol, 20 mol %), N-benzylindole 1b (102.5 mg, 0.5 mmol, 1 equiv), EtMe$_2$SiH (197 μL, 1.5 mmol, 3 equiv) and 0.5 mL of THF at 45° C. for 96 h. C2:C3>20:1. The desired product 2v (87.9 mg, 60% yield) was obtained as a colorless oil after purification by silica gel flash chromatography (10% CH$_2$Cl$_2$ in hexanes). Rf=0.3 (10% CH$_2$Cl$_2$ in hexanes); $^1$H NMR (500 MHz, CDCl$_3$) δ 7.75-7.69 (m, 1H), 7.34-7.23 (m, 3H), 7.23-7.11 (m, 3H), 6.96 (ddd, J=6.8, 2.2, 1.2 Hz, 2H), 6.88 (s, 1H), 5.54 (s, 2H), 1.00 (t, J=7.9 Hz, 3H), 0.79 (q, J=7.8 Hz, 2H), 0.32 (s, 6H); $^{13}$C NMR (125 MHz, CDCl$_3$) δ 140.5, 140.1, 138.4, 128.9, 128.7, 127.3, 125.9, 122.4, 120.8, 119.6, 112.9, 110.1, 50.1, 7.8, 7.5, −2.6. IR (Neat Film, NaCl) 3060, 3028, 2954, 2910, 2873, 1605, 1495, 1466, 1450, 1377, 1353, 1334, 1300, 1249, 1196, 1164, 1115, 1096, 1014, 958, 823, 780, 725 cm$^{-1}$; HRMS (MM: ESI-APCI+) calc'd for C$_{19}$H$_{23}$NSi [M+H]+: calculated 293.1600, found 293.1590

In a second experiment, 1-benzylindole (104 mg, 0.5 mmol, 1 equiv.), KOt-Bu (17 mg, 0.15 mmol, 0.3 equiv) and EtMe₂SiH (198 microliters, 1.5 mmol, 3 equiv.) in was stirred in 1 mL of tetrahydrofuran for 65 hours at 25° C. After aqueous work up, the crude reaction mixture was purified by chromatography on silica using an 80:1:4 mixture of hexanes:diethyl ether:triethylamine respectively to obtain 107 mg (73%) of the title compound as a colourless oil. $^1$H NMR (500 MHz, THF-d₈) δ 7.55 (ddd, 7.7, 1.4, 0.8 Hz, 1H), 7.22-7.16 (m, 2H), 7.16-7.09 (m, 2H), 7.02 (ddd, J=8.2, 6.9, 1.4 Hz, 1H), 6.97 (ddd, J=8.0, 6.9, 1.2 Hz, 1H), 6.86 (ddd, 7.2, 1.3, 0.7 Hz, 2H), 6.78 (d, J=0.9 Hz, 1H), 5.51 (d, J=1.1 Hz, 2H), 0.95-0.90 (m, 3H), 0.24 (s, 6H). $^{13}$C NMR (126 MHz, THF-d8) δ 141.31, 140.50, 139.94, 130.09, 129.39, 127.90, 126.71, 122.96, 121.45, 120.10, 113.93, 110.81, 50.62, 8.50, 7.93, −2.40.

Example 6.9.24:
1-Benzyl-2-(dimethyl(phenyl)silyl)-1H-indole 2w

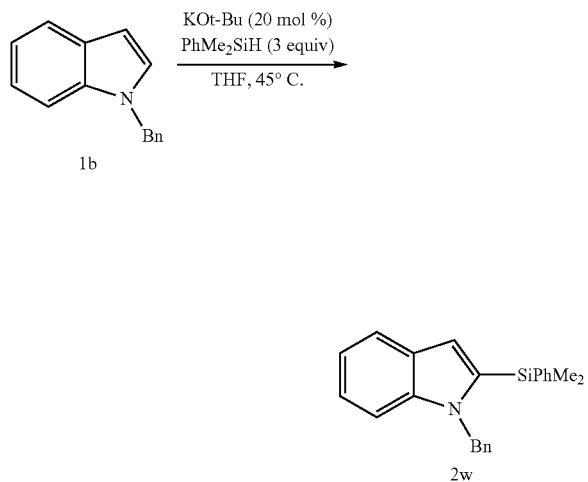

The reaction was conducted according to the General Procedure by heating KOt-Bu (11.2 mg, 0.1 mmol, 20 mol %), N-benzylindole 1b (103.5 mg, 0.5 mmol, 1 equiv), PhMe₂SiH (230 μL, 1.5 mmol, 3 equiv) and 0.5 mL of THF at 45° C., for 96 h. C2:C3>20:1. A mixture of starting material 1b and product 2w (174.5 mg of mixture, contains 133.9 mg of 2w, 78% yield, calculated based on $^1$H NMR) was obtained after purification by silica gel flash chromatography (2% EtOAc in hexanes). Analytically pure compound 2w was obtained as a white solid after subsequent purification by Preparative HPLC (3% EtOAc in hexanes). Rf=0.4 (5% EtOAc in hexanes); $^1$H NMR (500 MHz, CDCl₃) δ 7.71-7.66 (m, 1H), 7.51-7.48 (m, 2H), 7.40-7.35 (m, 1H), 7.34-7.29 (m, 2H), 7.21-7.16 (m, 3H), 7.14-7.08 (m, 3H), 6.90 (d, J=0.7 Hz, 1H), 6.78-6.75 (m, 2H), 5.25 (s, 2H), 0.50 (s, 6H); $^{13}$C NMR (125 MHz, CDCl₃) δ 140.4, 139.4, 138.3, 137.5, 134.2, 129.6, 128.9, 128.6, 128.1, 127.2, 125.9, 122.6, 121.0, 119.6, 114.1, 110.2, 50.0, −1.7. IR (Neat Film, NaCl) 3064, 3027, 2956, 1605, 1587, 1494, 1466, 1450, 1427, 1353, 1335, 1301, 1250, 1197, 1164, 1116, 1106, 1096, 1014, 905, 822 cm$^{-1}$; HRMS (MM: ESI-APCI+) calc'd for C₂₃H₂₄NSi [M+H]+ 342.1673, found 342.1676.

Example 6.9.25:
1-Methyl-2-(tributylsilyl)-1H-indole 2x

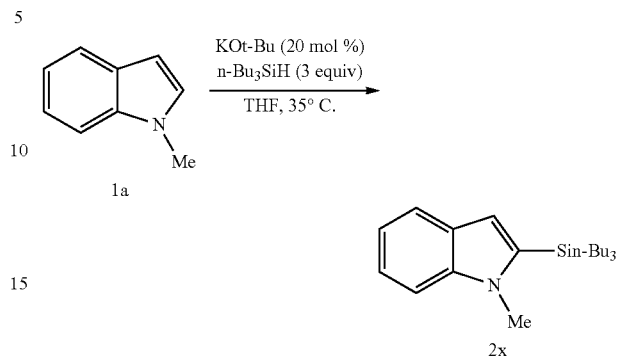

The reaction was conducted according to the General Procedure by heating KOt-Bu (11.2 mg, 0.1 mmol, 20 mol %), N-methylindole 1a (65.6 mg, 0.5 mmol, 1 equiv), n-Bu₃SiH (385 μL, 1.5 mmol, 3 equiv), and 0.5 mL of THF at 35° C. for 65 h. C2:C3>20:1. The desired product 2x (123.5 mg, 75% yield) was obtained as a white solid after purification by silica gel flash chromatography (100% hexanes). Rf=0.5 (100% hexanes). $^1$H NMR (500 MHz, CDCl₃) δ 7.61 (dt, J=7.9, 1.0 Hz, 1H), 7.37-7.30 (m, 1H), 7.22 (ddd, J=8.2, 6.9, 1.1 Hz, 1H), 7.08 (ddd, J=7.9, 6.9, 1.0 Hz, 1H), 6.69 (d, J=0.9 Hz, 1H), 3.84 (s, 3H), 1.38-1.27 (m, 12H), 0.94-0.86 (m, 15H); $^{13}$C NMR (125 MHz, CDCl₃) δ 140.2, 139.0, 128.6, 121.7, 120.5, 118.9, 112.7, 108.9, 32.9, 26.6, 26.1, 13.6, 12.7; IR (Neat Film, NaCl) 2955, 2922, 2871, 2855, 1492, 1464, 1411, 1375, 1356, 1325, 1298, 1232, 1196, 1166, 1102, 1070, 897, 885, 799, 788, 749, 732 cm$^{-1}$; HRMS (EI+) calc'd for C₂₁H₃₅NSi [M.+]: 329.2539, found 329.2523

Example 6.9.26: 1-Methyl-2-(triethylsilyl)-1H-pyrrolo[3,2-b]pyridine 4a

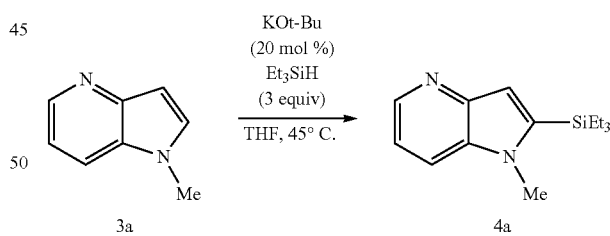

The reaction was conducted according to the General Procedure by heating KOt-Bu (4.5 mg, 0.04 mmol, 20 mol %), N-methyl-4-azaindole 3a (26.4 mg, 0.2 mmol, 1 equiv), Et₃SiH (98 μL, 0.6 mmol, 3 equiv) and 0.2 mL of THF at 45° C. for 96 h. C2:C3=6:1. A mixture of C2- and C3-silylation products (16.2 mg, 33% yield) was obtained after purification by silica gel flash chromatography (50% EtOAc in hexanes). Analytically pure C2-silylation 4a was obtained as a colorless oil after subsequent purification by Preparative TLC (50% EtOAc in hexanes). Rf=0.1 (33% EtOAc in hexanes); $^1$H NMR (500 MHz, CDCl₃) δ 8.44 (dd, J=4.6, 1.4 Hz, 1H), 7.60 (dt, J=8.3, 1.2 Hz, 1H), 7.09 (dd, J=8.3, 4.6 Hz, 1H), 6.90 (d, J=0.9 Hz, 1H), 3.83 (s, 3H), 1.03-0.97 (m, 9H), 0.96-0.89 (m, 6H); $^{13}$C NMR (125 MHz, CDCl$_3$) δ 147.0, 143.0, 142.7, 133.0, 116.4, 116.1, 113.8, 33.1, 7.6, 4.0. IR (Neat Film, NaCl) 2953, 2909, 2874, 1596, 1557, 1455, 1434, 1413, 1355, 1317, 1288, 1237, 1134, 1064, 1004, 800 cm$^{-1}$; HRMS calc'd for C$_{14}$H$_{23}$N$_2$Si [M+H]+: 247.1625, found 247.1621.

Example 6.9.27: 1-Methyl-2-(triethylsilyl)-1H-pyrrolo[3,2-c]pyridine 4b

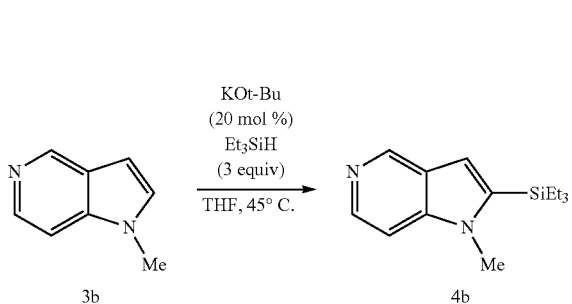

The reaction was conducted according to the General Procedure by heating KOt-Bu (11.2 mg, 0.1 mmol, 20 mol %), N-methyl-5-azaindole 3b (66.0 mg, 0.5 mmol, 1 equiv), Et$_3$SiH (243 μL, 1.5 mmol, 3 equiv), and 0.5 mL of THF at 45° C. for 120 h. C2:C3>20:1. The desired product 4b (37.9 mg, 31% yield) was obtained as a yellow oil after purification by silica gel flash chromatography (100% EtOAc). Rf=0.2 (100% EtOAc); $^1$H NMR (500 MHz, CDCl$_3$) δ 8.87 (d, J=1.1 Hz, 1H), 8.28 (d, J=5.9 Hz, 1H), 7.24-7.18 (m, 1H), 6.80 (d, J=0.9 Hz, 1H), 3.82 (s, 3H), 1.02-0.96 (m, 9H), 0.94-0.87 (m, 6H); $^{13}$C NMR (125 MHz, CDCl$_3$) δ 143.7, 143.6, 140.8, 140.4, 125.7, 112.9, 104.5, 32.9, 7.6, 4.0. IR (Neat Film, NaCl) 2953, 2909, 2874, 1597, 1563, 1485, 1463, 1435, 1415, 1368, 1334, 1310, 1291, 1219, 1184, 1123, 1069, 1004, 900, 809 cm$^{-1}$; HRMS (ESI+) calc'd for C$_{14}$H$_{23}$N$_2$Si [M+H]+: 247.1625, found 247.1626.

Example 6.9.28: 1-Methyl-2-(triethylsilyl)-1H-pyrrolo[2,3-c]pyridine 4c

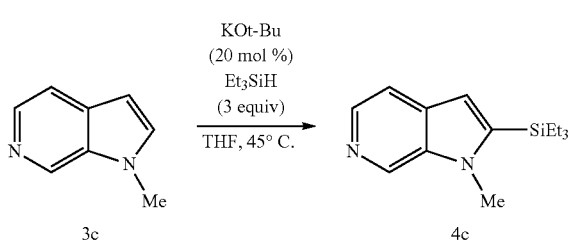

The reaction was conducted according to the General Procedure by heating KOt-Bu (5.8 mg, 0.52 mmol, 20 mol %), N-methyl-6-azaindole 3c (35.0 mg, 0.26 mmol, 1 equiv), Et$_3$SiH (126 μL, 0.78 mmol, 3 equiv), and 0.3 mL of THF at 45° C. for 94 h. C2:C3>20:1. The desired product 4c (32.9 mg, 50% yield) was obtained as a yellow oil after purification by silica gel flash chromatography (gradient elution, 2.5→5% MeOH in CH$_2$Cl$_2$). Rf=0.3 (5% MeOH in CH$_2$Cl$_2$); $^1$H NMR (500 MHz, CDCl$_3$) δ 8.76 (s, 1H), 8.20 (d, J=5.5 Hz, 1H), 7.47 (dd, J=5.5, 1.1 Hz, 1H), 6.68 (d, J=0.8 Hz, 1H), 3.93 (s, 3H), 1.03-0.97 (m, 9H), 0.95-0.89 (m, 6H); $^{13}$C NMR (125 MHz, CDCl$_3$) δ 143.5, 138.1, 137.2, 133.0, 132.6, 114.7, 112.0, 33.3, 7.5, 3.9. IR (Neat Film, NaCl) 2952, 2909, 2874, 1594, 1559, 1496, 1475, 1457, 1415, 1358, 1333, 1315, 1286, 1241, 1167, 1120, 1070, 1004, 817, 808 cm$^{-1}$; HRMS (EST+) calc'd for C$_{14}$H$_{23}$N$_2$Si [M+H]+: 247.1625, found 247.1620.

Example 6.9.29: 1-Methyl-2-(triethylsilyl)-1H-pyrrolo[2,3-b]pyridine 4d

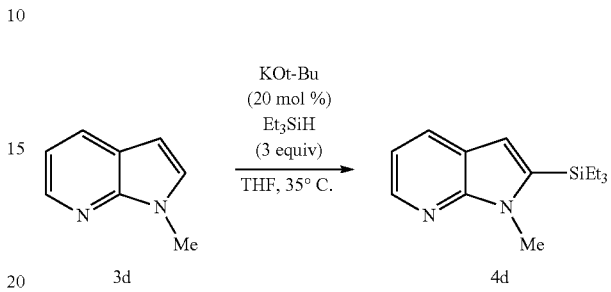

The reaction was conducted according to the General Procedure by heating KOt-Bu (11.2 mg, 0.1 mmol, 20 mol %), N-methyl-7-azaindole 3d (66 mg, 0.5 mmoL, 1 equiv), Et$_3$SiH (243 μL, 1.5 mmol, 3 equiv), and 0.5 mL of THF at 35° C. for 63 h. C2:C3>20:1. The desired product 4d (87.1 mg, 71% yield) was obtained as a colorless oil after purification by silica gel flash chromatography (gradient elution, 0→10% EtOAc in hexanes). Rf=0.3 (10% EtOAc in hexanes); 1HNMR (500 MHz, CDCl$_3$) δ 8.33 (dd, J=4.7, 1.6 Hz, 1H), 7.87 (dd, J=7.8, 1.6 Hz, 1H), 7.02 (dd, J=7.8, 4.7 Hz, 1H), 6.67 (s, 1H), 3.95 (s, 3H), 1.04-0.97 (m, 9H), 0.96-0.88 (m, 6H); $^{13}$C NMR (125 MHz, CDCl$_3$) δ 151.0, 143.2, 139.2, 128.3, 120.7, 115.3, 111.0, 31.4, 7.6, 3.9. IR (Neat Film, NaCl) 3052, 2953, 2910, 2874, 1590, 1570, 1489, 1444, 1403, 1302, 1286, 1226, 1162, 1134, 1107, 1066, 1004, 906, 804, 772, 739 cm$^{-1}$; HRMS (FAB+) calc'd for C$_{14}$H$_{23}$N$_2$Si [M+H]+: 247.1631, found 247.1637. The HSQC spectrum of this reaction product has previously been reported in U.S. Pat. No. 9,000,167.

Example 6.9.30: 1-Methyl-2-(triethylsilyl)-1H-pyrrolo[2,3-b]pyridine 4e

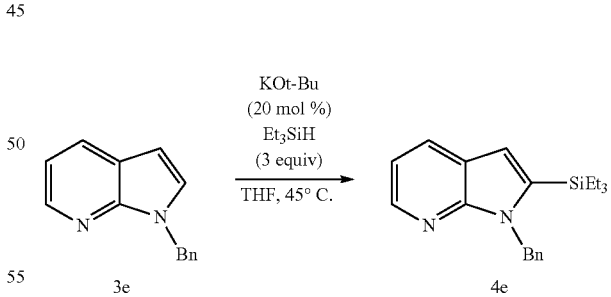

The reaction was conducted according to the General Procedure by heating KOt-Bu (11.2 mg, 0.1 mmol, 20 mol %), N-benzyl-7-azaindole 3e (104.0 mg, 0.5 mmol, 1 equiv), Et$_3$SiH (243 μL, 1.5 mmol, 3 equiv), and 0.5 mL of THF at 45° C. for 144 h. C2:C3>20:1. The desired product 4e (89.4 mg, 56% yield) was obtained as a colorless oil purification by silica gel flash chromatography (gradient elution, 2.5→5% EtOAc in hexanes). Rf=0.3 (5% EtOAc in hexanes); $^1$H NMR (500 MHz, CDCl$_3$) δ 8.34 (dd, J=4.7, 1.6 Hz, 1H), 7.94 (dd, J=7.8, 1.6 Hz, 1H), 7.25-7.16 (m, 3H), 7.07 (dd, J=7.8, 4.6 Hz, 1H), 6.87-6.85 (m, 2H), 6.79 (s, 1H), 5.69 (s, 214), 0.91-0.83 (m, 9H), 0.74-0.69 (m, 6H); $^{13}$C NMR (125 MHz, CDCl$_3$) δ 151.2, 143.7, 139.04, 138.96, 128.6, 128.4, 127.0, 125.9, 120.5, 115.7, 112.2, 47.8, 7.4, 3.7. IR (Neat Film, NaCl) 2954, 2874, 1589, 1570, 1495, 1452, 1439, 1422, 1378, 1357, 1309, 1239, 1157, 1103, 1004, 909, 803, 777 cm$^{-1}$; HRMS (MM: ESIAPCI+) calc'd for C$_{20}$H$_{27}$N$_2$Si [M+H]+: 323.1938, found 323.1947.

Example 6.9.31: 1-Benzyl-2-(diethylsilyl)-1H-pyrrolo[2,3-b]pyridine 4f

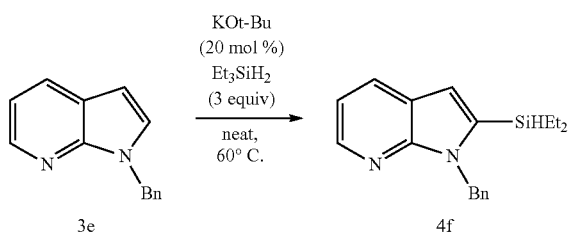

The reaction was conducted according to the General Procedure by heating KOt-Bu (11.2 mg, 0.1 mmol, 20 mol %), N-benzyl-7-azaindole 3e (104.5 mg, 0.5 mmol, 1 equiv) and Et$_2$SiH$_2$ (194 µL, 1.5 mmol, 3 equiv) at 60° C. for 84 h. C2:C3>20:1. The desired product 4f (96.2 mg, 65% yield) was obtained as a yellow oil after purification by silica gel flash chromatography (3% EtOAc in hexanes). Rf=0.4 (10% EtOAc in hexanes); $^1$H NMR (500 MHz, CDCl$_3$) δ 8.37 (dd, J=4.7, 1.6 Hz, 1H), 7.95 (dd, J=7.8, 1.6 Hz, 1H), 7.30-7.16 (m, 3H), 7.09 (dd, J=7.8, 4.6 Hz, 1H), 7.01-6.99 (m, 2H), 6.80 (s, 1H), 5.71 (s, 2H), 4.32 (p, J=3.3 Hz, 1H), 0.95 (t, J=7.9 Hz, 6H), 0.78-0.63 (m, 4H); $^{13}$C NMR (125 MHz, CDCl$_3$) δ 150.9, 143.8, 138.9, 137.4, 128.6, 128.5, 127.2, 126.6, 120.5, 115.8, 111.7, 47.6, 8.1, 3.4. IR (Neat NaCl) 2955, 2873, 2120, 1590, 1568, 1495, 1453, 1439, 1422, 1358, 1300, 1235, 1156, 1100, 1009, 973, 910, 808 cm$^{-1}$; HRMS (MM: ESI-APCI+) calc'd for C$_{18}$H$_{23}$N$_2$Si [M+H]+: 295.1625, found 295.1636.

Example 6.9.32: 1-Benzyl-2-(dimethyl(phenyl)silyl)-1H-pyrrolo[2,3-b]pyridine 4g

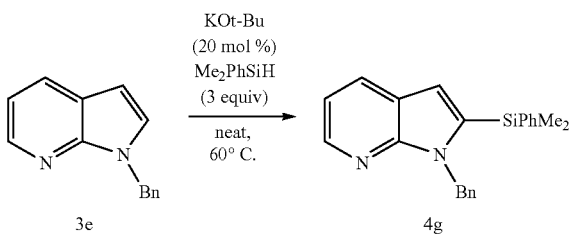

The reaction was conducted according to the General Procedure by heating KOt-Bu (11.2 mg, 0.1 mmol, 20 mol %), N-benzyl-7-azaindole 3e (103.9 mg, 0.5 mmol, 1 equiv) and PhMe$_2$SiH (230 µL, 1.5 mmol, 3 equiv) at 60° C. for 96 h. C2:C3>20:1. The desired product 4g (118.0 mg, 69% yield) was obtained as a yellow oil after purification by silica gel flash chromatography (3% EtOAc in hexanes). Rf=0.4 (10% EtOAc in hexanes); $^1$H NMR (500 MHz, CDCl$_3$) δ 8.35 (dd, J=4.7, 1.6 Hz, 1H), 7.97 (dd, J=7.8, 1.6 Hz, 1H), 7.49-7.45 (m, 2H), 7.41-7.38 (m, 1H), 7.37-7.32 (m, 2H), 7.20-7.13 (m, 3H), 7.08 (dd, J=7.8, 4.6 Hz, 1H), 6.84 (s, 1H), 6.77-6.68 (m, 2H), 5.46 (s, 2H), 0.42 (s, 6H); $^{13}$C NMR (125 MHz, CDCl$_3$) δ 151.3, 144.0, 140.0, 138.8, 136.9, 134.2, 129.7, 128.8, 128.5, 128.1, 127.0, 126.1, 120.4, 115.9, 112.2, 47.6, −2.0. IR (Neat Film, NaCl) 3050, 3027, 2956, 1589, 1569, 1495, 1439, 1427, 1359, 1309, 1250, 1156, 1107, 1029, 987, 910, 822 cm$^{-1}$; HRMS (MM: ESI-APCI+) calc'd for C$_{22}$H$_{23}$N$_2$Si [M+H]+: 343.1625, found 343.1635.

Example 6.9.33: Benzofuran-2-yltriethyl silane

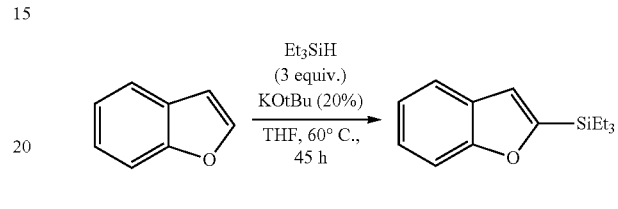

The reaction was conducted according to the General Procedure by heating benzofuran (59 mg, 0.5 mmol, 1 equiv.), KOt-Bu (19.6 mg, 0.18 mmol, 0.35 equiv.) and Et$_3$SiH (239 microliters, 1.5 mmol, 3 equiv.) in 1 mL of tetrahydrofuran for 45 hours at 60° C. After aqueous work up, the crude reaction mixture was purified by chromatography on silica eluting with hexanes (isochratic) to obtain 44 mg (38%) of the title compound as a colourless oil. $^1$H NMR (500 MHz, Acetone-d6) δ 7.64 (ddd, J=7.7, 1.3, 0.7 Hz, 1H), 7.53 (dd, J=8.2, 0.9 Hz, 1H), 7.30 (ddd, J=8.3, 7.2, 1.3 Hz, 1H), 7.22 (ddd, J=7.7, 7.2, 1.0 Hz, 1H), 7.16 (J=1.0 Hz, 1H), 1.09-0.98 (m, 9H), 0.92-0.84 (m, 6H). The HSQC spectrum of this reaction product has previously been reported in U.S. Pat. No. 9,000,167.

Example 6.9.34: Benzo[b]thiophen-2-yltriethylsilane 4h

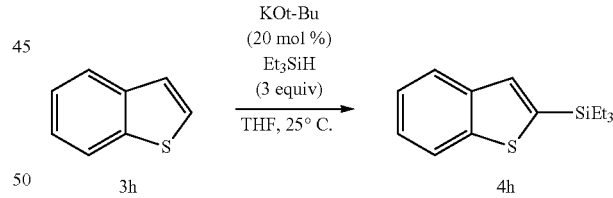

(Note: the product of this reaction was previously mischaracterized as benzo[b]thiophen-3-yltriethylsilane. The spectral data has been re-interpreted to provide the structure given here). The reaction was conducted according to the General Procedure by heating KOt-Bu (11.2 mg, 0.1 mmol, 20 mol %), benzo[b]thiophene 3h (67.0 mg, 0.5 mmol, 1 equiv), Et$_3$SiH (243 µL, 1.5 mmol, 3 equiv), and 0.5 mL of THF at 25° C. for 60 h. The desired product 4h (120.3, 97% yield) was obtained as a colorless oil after purification by silica gel flash chromatography (100% hexanes), Rf=0.6 (100% hexanes). $^1$H NMR (500 MHz, CDCl$_3$) δ 7.91 (m, 1H), 7.87-7.81 (m, 1H), 7.49 (m, 1H), 7.41-7.29 (m, 2H), 1.07-1.03 (m, 9H), 0.96-0.85 (m, 6H). The HSQC spectrum of this reaction product has previously been reported in U.S. Pat. No. 9,000,167.

This material was also made at scale as follows. In a nitrogen-filled glove box, KOt-Bu (1.7 g, 115 mmol, 20 mol %), benzo[b]thiophene 3h (10.1 g, 75 mmol, 1 equiv), Et$_3$SiH (23.3 mL, 146 mmol, 2 equiv), and 75 mL of THF were added to a 250 mL media jar equipped with a magnetic stir bar and sealed with a polypropylene cap. The reaction mixture was stirred at 25° C. for 60 h. The jar was then removed from the glovebox, opened carefully (caution: gas released!), and diluted with anhydrous Et$_2$O (30 mL). The reaction was filtered, the solvent was removed in vacuo and the residual volatiles were removed under high vacuum (30 millitorr; 23° C.). The desired product 4h (17.3 g, 93% yield) was obtained as a colorless oil after purification by silica gel flash chromatography (100% hexanes).

Example 6.9.35:
Benzo[b]thiophen-2-yldimethyl(phenyl)silane 4i

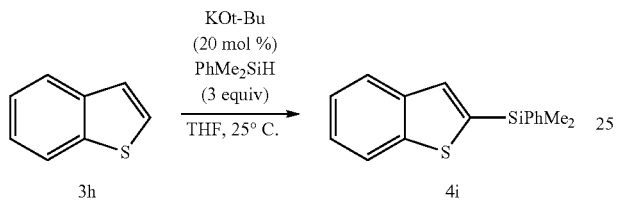

(Note: the product of this reaction was previously mischaracterized as benzo[b]thiophen-3-yldimethyl(phenyl)silane. The spectral data has been re-interpreted to provide the structure given here). The reaction was conducted according to the General Procedure by heating KOt-Bu (11.2 mg, 0.1 mmol, 20 mol %), benzo[b]thiophene 3h (67.0 mg, 0.5 mmol, 1 equiv), PhMe$_2$SiH (230 μL, 11.5 mmol, 3 equiv), and 0.5 mL of THF at 25° C. for 60 h. The desired product 4i (116.6 mg, 87% yield) was obtained as a colorless oil after purification by silica gel flash chromatography (100% hexanes). Rf=0.5 (100% hexanes). $^1$H NMR (500 MHz, CDCl$_3$) δ 7.94-7.87 (m, 1H), 7.87-7.79 (m, 1H), 7.68-7.59 (m, 2H), 7.51 (d, J=0.8 Hz, 1H), 7.46-7.39 (m, 3H), 7.38-7.31 (m, 2H), 0.69 (s, 6H).
$^{13}$C NMR (126 MHz, CDCl$_3$) δ 144.01, 141.12, 140.18, 137.29, 134.13, 132.41, 129.70, 128.09, 124.45, 124.18, 123.69, 122.33, −1.42, HRMS: [C$_{16}$H$_{16}$SSi] calculated 268.0743, measured 268.0742

Example 6.9.36:
2-(5-(Triethylsilyl)thiophen-2-yl)pyridine 4j

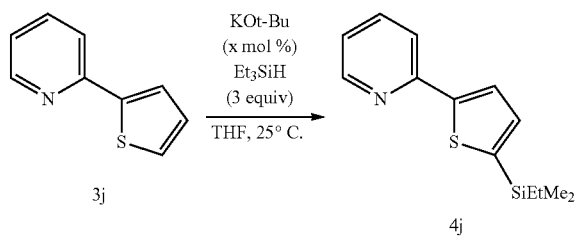

condition A: 0.5 mmol, 20 mol % KOt-Bu, 35 h 94%
condition B: 5 mmol, 3.5 mol % KOt-Bu, 96 h 82%

The reactions were conducted according to the General Procedure. Condition A: The reaction was performed with KOt-Bu (11.2 mg, 0.1 mmol, 20 mol %), 2-(thiophen-2-yl)pyridine 3j (80.5 mg, 0.5 mmol, 1 equiv), Et$_3$SiH (243 μL, 1.5 mmol, 3 equiv), and 0.5 mL of THF at 25° C. for 35 h. The desired product 4j (129.3 mg, 94% yield) was obtained as a colorless oil after purification by silica gel flash chromatography (5% EtOAc in hexanes). Condition B: The reaction was performed with KOt-Bu (19.6 mg, 0.18 mmol, 3.5 mol %), 2-(thiophen-2-yl)pyridine 3j (0.81 g, 5 mmol, 1 equiv), Et$_3$SiH (2.43 mL, 15 mmol, 3 equiv), and 3.0 mL of THF at 25° C. for 96 h. The desired product 4j (1.13 g, 82% yield) was obtained as a colorless oil after purification by silica gel flash chromatography (5% EtOAc in hexanes). Rf=0.3 (5% EtOAc in hexanes); $^1$H NMR (500 MHz, CDCl$_3$) δ 8.56 (d, J=4.7 Hz, 1H), 7.61 (dt, J=3.9, 1.7 Hz, 3H), 7.23 (d, J=3.3 Hz, 1H), 7.08 (q, J=4.8 Hz, 1H), 1.01 (t, J=7.9 Hz, 9H), 0.82 (q, 7.9 Hz, 6H). $^{13}$C NMR (125 MHz, CDCl$_3$) δ 152.8, 149.8, 149.6, 139.7, 136.6, 135.6, 125.7, 121.8, 119.0, 7.4, 4.5; IR (Neat Film, NaCl) 3054, 3001, 2953, 2909, 2874, 1585, 1563, 1528, 1517, 1464, 1436, 1422, 1377, 1315, 1290, 1238, 1207, 1151, 1077, 1066, 1047, 1007, 990, 962, 807, 774, 737 cm$^{-1}$; HRMS (FAB+) calc'd for C$_{15}$H$_{22}$NSSi [M+H]+: 276.1242, found 276.1239.

Example 6.9.37:
2-(5-(Ethyldimethylsilyl)thiophen-2-yl)pyridine 4k

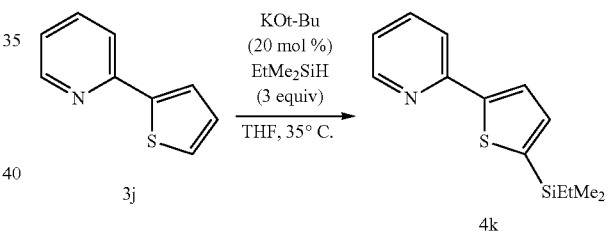

The reaction was conducted according to the General Procedure by heating KOt-Bu (11.2 mg, 0.1 mmol, 20 mol %), 2-(thiophen-2-yl)pyridine 3j (80.5 mg, 0.5 mmol, 1 equiv), EtMe$_2$SiH (198 μL, 1.5 mmol, 3 equiv), and 0.5 mL of THF at 35° C. for 48 h. The desired product 4k (107.4 mg, 87% yield) was obtained as a colorless oil after purification by silica gel flash chromatography (10% Et$_2$O in hexanes). Rf=0.4 (10% Et2O in hexanes); $^1$H NMR (500 MHz, CDCl$_3$) δ 8.58 (ddd, J=4.9, 1.8, 1.1 Hz, 1H), 7.72-7.63 (m, 2H), 7.62 (d, J=3.5 Hz, 1H), 7.24 (d, J=3.5 Hz, 1H), 7.13 (ddd, J=6.7, 4.9, 2.0 Hz, 1H), 1.05-0.96 (m, 3H), 0.78 (qd, J=7.8, 0.8 Hz, 2H), 0.32 (s, 6H); $^{13}$C NMR (125 MHz, CDCl$_3$) δ 152.7, 149.7, 149.6, 141.9, 136.6, 135.0, 125.6, 121.7, 118.9, 8.3, 7.2, −2.5; IR (Neat Film, NaCl) 3054, 3001, 2953, 2909, 2874, 1585, 1563, 1528, 1517, 1464, 1436, 1422, 1315, 1290, 1248, 1207, 1151, 1077, 1066, 1047, 1007, 990, 964, 836, 812, 774, 752, 737, 712 cm$^{-1}$; HRMS (FAB+) calc'd for C$_{13}$H$_{18}$NSSi [(M+H)+−H2]: 248.0929, found 248.0935.

Example 6.9.38:
2-(5-(Dimethyl(phenyl)silyl)thiophen-2-yl)pyridine 4l

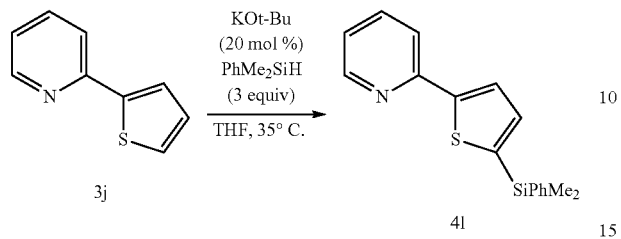

The reaction was conducted according to the General Procedure by heating KOt-Bu (11.2 mg, 0.1 mmol, 20 mol %), 2-(thiophen-2-yl)pyridine 3j (80.5 mg, 0.5 mmol, 1 equiv), PhMe$_2$SiH (230 µL, 1.5 mmol, 3 equiv), and 1.0 mL of THF at 35° C. for 48 h. The desired product 4l (118.1 mg, 80% yield) was obtained as a colorless oil after purification by silica gel flash chromatography (10% Et$_2$O in hexanes). Rf=0.3 (10% Et2O in hexanes); $^1$H NMR (500 MHz, CDCl$_3$) δ 8.60-8.54 (m, 1H), 7.72-7.56 (m, 5H), 7.43-7.33 (m, 3H), 7.26 (m, 1H), 7.14 (m, 1H), 0.63 (s, 6H); $^{13}$C NMR (125 MHz, CDCl$_3$) δ 152.4, 150.3, 149.5, 140.6, 137.3, 136.6, 136.0, 133.8, 129.3, 127.8, 125.6, 121.8, 118.9, −1.6; IR (Neat Film, NaCl) 3067, 2955, 1586, 1563, 1527, 1463, 1423, 1316, 1290, 1249, 1207, 1151, 1112, 1077, 1005, 989, 963, 807, 773, 731 cm$^{-1}$; HRMS (FAB+) calc'd for C$_{17}$H$_{18}$NSSi [M+H]+: 296.0929, found 296.0938.

Example 6.9.39:
Triethyl(5-pentylthiophen-2-yl)silane 4m

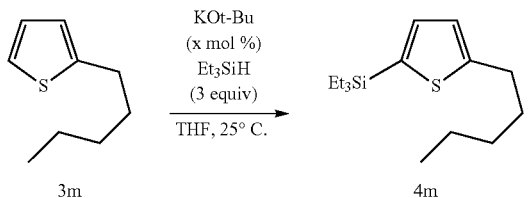

condition A: 0.5 mmol, 20 mol % KOt-Bu, 48 h 96%
condition B: 5 mmol, 1 mol % KOt-Bu, 96 h 92%

The reaction was conducted according to the General Procedure, Condition A: The reaction was performed with KOt-Bu (11.2 mg, 0.1 mmol, 20 mol %), 2-pentylthiophene 3m (77.0 mg, 0.5 mmol, 1 equiv), Et$_3$SiH (243 µL, 1.5 mmol, 3 equiv), and 0.5 mL of THF at 25° C. for 48 h. The desired product 4m (130.0 mg, 96% yield) was obtained as a colorless oil after purification by silica gel flash chromatography (100% hexanes). Condition B: The reaction was performed with KOt-Bu (5.6 mg, 0.05 mmol, 1 mol %), 2-pentylthiophene 3m (770.4 mg, 5.0 mmol, 1 equiv), Et$_3$SiH (2.43 mL, 15 mmol, 3 equiv), and 3.0 mL of THF at 25° C. for 96 h. The desired product 4m (1.23 g, 92% yield) was obtained as a colorless oil after purification by silica gel flash chromatography (100% hexanes). Rf=0.6 (100% hexanes); $^1$H NMR (500 MHz, CDCl$_3$) δ 7.12 (dd, J=3.3, 1.5 Hz, 1H), 6.91 (dt, J=3.3, 1.0 Hz, 1H), 2.90 (td, J=7.7, 1.2 Hz, 2H), 1.81-1.71 (m, 2H), 1.48-1.36 (m, 4H), 1.06 (t, J=7.8 Hz, 9H), 0.99-0.94 (m, 3H), 0.84 (qd, J=7.8, 1.0 Hz, 6H); $^{13}$C NMR (125 MHz, CDCl$_3$) δ 151.6, 134.7, 134.1, 125.5, 31.7, 31.6, 30.2, 22.6, 141, 7.5, 4.7; IR (Neat Film, NaCl) 3054, 2955, 2934, 2874, 1750, 1528, 1456, 1438, 1413, 1378, 1339, 1235, 1213, 1058, 1011, 988, 799, 736 cm$^{-1}$; HRMS (FAB+) calc'd for C$_{15}$H$_{27}$SSi [(M+H)−H2]+: 267.1603, found 267.1609.

Example 6.9.40: Triethyl(5-pentylfuran-2-yl)silane 4n

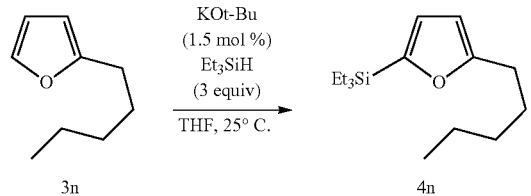

The reaction was conducted according to the General Procedure by heating KOt-Bu (8.4 mg, 0.075 mmol, 1.5 mol %), 2-pentylfuran 3n (691 mg, 5.0 mmol, 1 equiv), (2.43 mL, 15 mmol, 3 equiv) and 3 mL of THF at 25° C. for 96 h. The desired product 4n (1.15 g, 91% yield) was obtained as a colorless oil after purification by silica gel flash chromatography (100% hexanes). Rf=0.6 (100% hexanes); $^1$H NMR (500 MHz, CDCl$_3$) δ 6.53 (d, J=3.0 Hz, 1H), 5.96 (dt, J=3.0, 0.9 Hz, 1H), 2.67-2.60 (m, 2H), 1.64 (dq, J=9.4, 7.4 Hz, 2H), 1.36-1.28 (m, 4H), 1.05-0.95 (m, 9H), 0.92-0.85 (m, 3H), 0.74 (qd, J=7.8, 0.8 Hz, 6H); $^{13}$C NMR (125 MHz, CDCl$_3$) δ 161.2, 156.2, 121.5, 104.6, 31.6, 28.3, 27.9, 22.6, 14.1, 7.5, 3.6; IR (Neat Film, NaCl) 3108, 2954, 2933, 2874, 1807, 1721, 1588, 1493, 1459, 1414, 1378, 1340, 1237, 1186, 1173, 1118, 1084, 1011, 962, 923, 782, 736, 724 cm$^{-1}$; HRMS (FAB+) calc'd for C$_{15}$H$_{27}$OSi [(M+H)−H2]+: 251.1831, found 251.1821.

This material was also made at scale using the same procedure as for the multigram scale synthesis of 4h. The reaction was performed with KOt-Bu (1.6 g, 14.6 mmol, 20 mol %), 2-pentylfuran 3n (110.1 g, 73 mmol, 1 equiv), Et$_3$SiH (23.3 mL, 146 mmol, 2 equiv), and 73 mL of THF at 25° C. for 72 h. The desired product 4n (17.4 g, 95% yield) was obtained as a colorless oil after filtration, removal of volatiles under high vacuum (30 millitorr, 23° C.) and purification by silica gel flash chromatography (100% hexanes).

Example 6.9.41: Reaction of 2-pentylfuran 3n with Et$_2$SiH$_2$

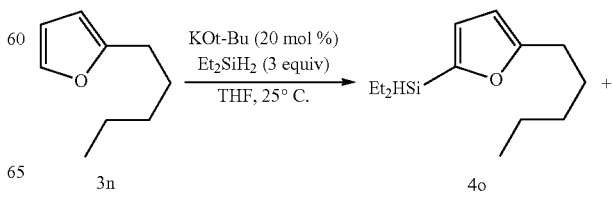

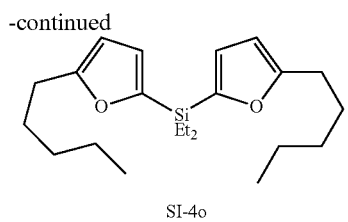

SI-4o

The reaction was conducted according to the General Procedure by heating KOt-Bu (11.2 mg, 0.1 mmol, 20 mol %), 2-pentylfuran 3n (69.1 mg, 0.5 mmol, 1 equiv), Et$_2$SiH$_2$ (195 μL, 1.5 mmol, 3 equiv), and 0.5 mL of THF at 25° C. for 76 h. The desired product 4o (87.4 mg, 78% yield) and silicon-tethered product SI-4o (12.4 mg, 8% yield) were obtained after purification by silica gel flash chromatography (100% hexanes).

Diethyl(5-pentylfuran-2-yl)silane 4o: Colorless oil, Rf=0.6 (100% hexanes); $^1$H NMR (500 MHz, CDCl$_3$) δ 6.63 (d, J=3.1 Hz, 1H), 6.00 (dt, J=3.1, 0.9 Hz, 1H), 4.21 (p, J=3.2 Hz, 1H), 2.75-2.64 (m, 2H), 1.73-1.62 (m, 2H), 1.38-1.32 (m, 4H), 1.11-1.04 (m, 6H), 0.95-0.90 (m, 3H), 0.88-0.81 (m, 4H); $^{13}$C NMR (125 MHz, CDCl$_3$) δ 161.8, 153.7, 122.7, 105.0, 31.6, 28.4, 27.9, 22.6, 14.1, 8.1, 3.2; IR (Neat Film, NaCl) 2955, 2931, 2873, 2120, 1588, 1493, 1461, 1233, 1082, 1010, 974, 925, 798, 715 cm$^{-1}$; HRMS (FAB+) calc'd for C$_{13}$H$_{23}$OSi [(M+H)−H2]+: 223.1518, found 223.1519.

Diethylbis(5-pentylfuran-2-yl)silane SI-4o: Colorless oil, Rf=0.7 (100% hexanes); $^1$H NMR (500 MHz, CDCl$_3$) δ 6.62 (d, J=3.1 Hz, 2H), 5.98 (dt, J=3.1, 0.9 Hz, 2H), 2.69-2.61 (m, 4H), 1.70-1.59 (m, 4H), 1.36-1.30 (m, 8H), 1.08-1.01 (m, 6H), 1.01-0.93 (m, 4H), 0.93-0.81 (m, 6H); $^{13}$C NMR (125 MHz, CDCl$_3$) δ 161.5, 153.7, 122.8, 104.8, 31.4, 28.2, 27.7, 22.4, 13.9, 7.2, 4.2; IR (Neat Film, NaCl) 2955, 2928, 2873, 2859, 1587, 1493, 1461, 1378, 1233, 1187, 1122, 1010, 961, 925, 783, 726 cm$^{-1}$; HRMS (EI+) calc'd for C$_{22}$H$_{36}$O$_2$Si [M.+]: 360.2485, found 360.2468.

Example 6.9.42: Tributyl(5-pentylfuran-2-yl)silane 4p

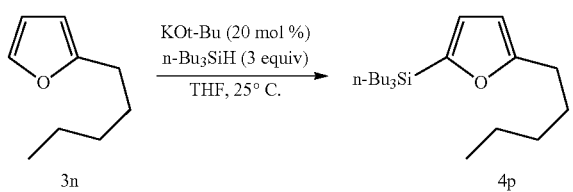

The reaction was conducted according to the General Procedure by heating KOt-Bu (11.2 mg, 0.1 mmol, 20 mol %), 2-pentylfuran 3n (69.1 mg, 0.5 mmol, 1 equiv), n-Bu$_3$SiH (386 μL, 1.5 mmol, 3 equiv), and 0.5 mL of THF at 25° C. for 108 h. The desired product 4p (137.8 mg, 82% yield) was obtained as a colorless oil after purification by silica gel flash chromatography (100% hexanes). Rf=0.71 (100% hexanes); $^1$H NMR (500 MHz, CDCl$_3$) (δ 6.50 (d, J=3.0 Hz, 1H), 5.95 (d, J=3.0, 1H), 2.67-2.60 (m, 2H), 1.69-1.59 (m, 2H), 1.39-1.24 (m, 16H), 0.94-0.83 (m, 12H), 0.79-0.69 (m, 6H); $^{13}$C NMR (125 MHz, CDCl$_3$) δ 161.0, 156.8, 121.3, 104.7, 31.6, 28.3, 28.0, 26.7, 26.2, 22.6, 14.1, 13.9, 12.3; IR (Neat Film, NaCl) 3107, 2956, 2923, 2871, 2857, 2099, 1677, 1588, 1493, 1464, 1410, 1376, 1341, 1296, 1271, 1217, 1187, 1175, 1082, 1050, 1010, 961, 925, 885, 781, 759, 732 cm$^{-1}$; HRMS (EI+) calc'd for C$_{21}$H$_{40}$OSi [M.+]: 336.2848, found 336.2859.

Example 6.9.43: 2,5-Bis(triethylsilyl)thiophene 4q

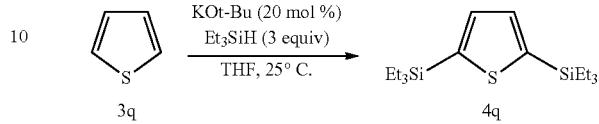

The reaction was conducted according to the General Procedure by heating KOt-Bu (11.2 mg, 0.1 mmol, 20 mol %), thiophene 3q (42.1 mg, 0.5 mmol, 1 equiv), Et$_3$SiH (243 μL, 1.5 mmol, 3 equiv), and 0.5 mL of THF at 25° C. for 72 h. The desired product 4q (134.2 mg, 86% yield) was obtained as a colorless oil after purification by silica gel flash chromatography (100% hexanes), Rf=0.6 (100% hexanes). $^1$H NMR (500 MHz, CDCl$_3$) δ 7.40 (s, 2H) 1.02-0.99 (m, 18H), 0.83-0.79 (m, 12H).

Example 6.9.44: Reaction of 1-benzyl-1H-pyrrole 3s with Et$_3$SiH

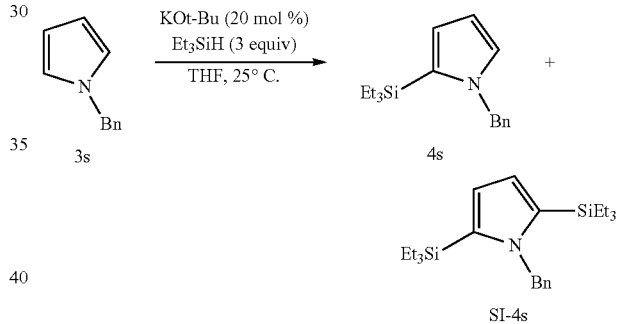

The reaction was conducted according to the General Procedure by heating KOt-Bu (11.2 mg, 0.1 mmol, 20 mol %), 1-benzyl-1H-pyrrole 3s (78.5 mg, 0.5 mmol, 1 equiv), Et$_3$SiH (243 μL, 1.5 mmol, 3 equiv), and 0.5 mL of THF at 25° C. for 108 h. The desired product 4s (100.3 mg, 74% yield) and bis-silylation product SI-4s (9.6 mg, 5%) were obtained after purification by silica gel flash chromatography (100% hexanes).

1-Benzyl-2-(triethylsilyl)-1H-pyrrole 4s: Colorless oil, Rf=0.3 (100% hexanes); $^1$H NMR (500 MHz, CDCl$_3$) δ 7.40-7.32 (m, 2H), 7.32-7.25 (m, 1H), 7.04-6.98 (m, 2H), 6.86 (dd, J=2.4, 1.5 Hz, 1H), 6.51 (dd, J=3.5, 1.5 Hz, 1H), 6.30 (dd, J=3.4, 2.4 Hz, 1H), 5.22 (s, 2H), 0.95 (t, J=7.8 Hz, 9H), 0.73 (q, J=7.8 Hz, 6H); $^{13}$C NMR (125 MHz, CDCl$_3$) δ 139.2, 129.9, 128.7, 127.5, 126.62, 126.56, 120.9, 108.9, 53.5, 7.6, 4.2; IR (Neat Film, NaCl) 3088, 3064, 3029, 2952, 2908, 2873, 1516, 1506, 1495, 1454, 1418, 1353, 1329, 1288, 1237, 1175, 1112, 1080, 1008, 969, 760 cm$^{-1}$; HRMS (EI+) calc'd for C$_{17}$H$_{25}$NSi [M.+]: 271.1756, found 271.1755.

1-Benzyl-2,5-bis(triethylsilyl)-1H-pyrrole SI-4s: Colorless oil, Rf=0.4 (100% hexanes); $^1$H NMR (500 MHz, CDCl$_3$) δ 7.29-7.21 (m, 2H), 7.21-7.15 (m, 1H), 6.72 (dq, J=7.1, 1.0 Hz, 2H), 6.52 (s, 2H), 5.28 (s, 2H), 0.85-0.82 (m, 18H), 0.63-0.52 (m, 12H), $^{13}$C NMR (125 MHz, CDCl$_3$) δ 140.4, 135.6, 128.2, 126.9, 125.5, 121.2, 53.3, 7.4, 3.9; IR (Neat Film, NaCl) 3027, 2952, 2909, 2874, 1605, 1498, 1485, 1454, 1416, 1377, 1343, 1277, 1237, 1161, 1075, 1002, 912, 775, 764, 731 cm$^{-1}$; HRMS (EI+) calc'd for C$_{23}$H$_{39}$NSi$_2$ [M.+]; 385.2621, found 385.2638.

Example 6.9.45:
1-Methyl-5-(triethylsilyl)-1H-pyrazole 4t

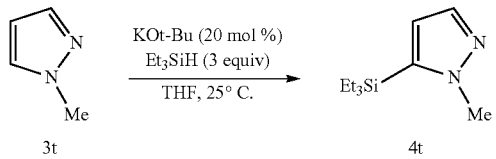

The reaction was conducted according to the General Procedure by heating KOt-Bu (11.2 mg, 0.1 mmol, 20 mol %), 1-methyl-1H-pyrazole 3t (41.1 mg, 0.5 mmol, 1 equiv), Et$_3$SiH (243 μL, 1.5 mmol, 3 equiv), and 0.5 mL of THF at 25° C. for 120 h. The desired product 4t (72.6 mg, 74% yield) was obtained as a colorless oil after purification by silica gel flash chromatography (1:1 Et2O: hexanes). Rf=0.3 (1:1 Et2O:hexanes). (Despotopoulou, C.; et al., *P Org. Lett.* 2009, 11, 3326) $^1$H NMR (500 MHz, CDCl$_3$) δ 7.47 (d, J=1.9 Hz, 1H), 6.37 (d, J=1.8 Hz, 1H), 3.95 (s, 3H), 0.96 (m, 9H), 0.83 (m, 6H).

Example 6.9.46:
Dibenzo[b,d]thiophen-4-yltriethylsilane 4u

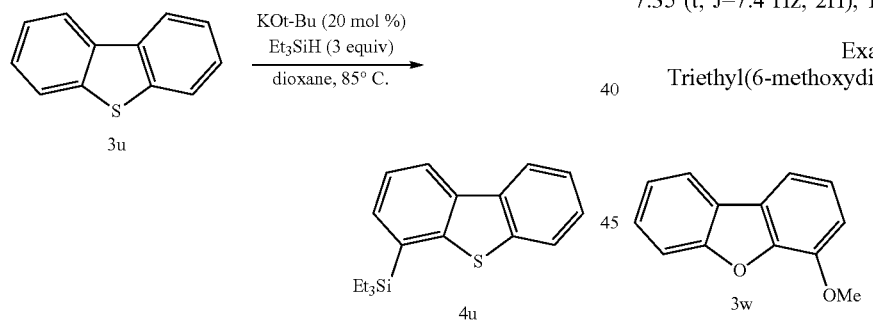

The reaction was conducted according to the General Procedure by heating KOt-Bu (11.2 mg, 0.1 mmol, 20 mol %), dibenzothiophene 3u (92 mg, 0.5 mmol, 1.0 equiv), Et$_3$SiH (243 μL, 1.5 mmol, 3.0 equiv), and 3 mL of dioxane at 85° C. for 72 h. The desired product 4u (55.4 mg, 38% yield) was obtained as a colorless oil after purification by silica gel flash chromatography (100% hexanes). Rf=0.7 (100% hexanes); $^1$H NMR (500 MHz, CDCl$_3$) δ 8.17 (m, 2H), 7.86 (m, 1H), 7.58 (m, 1H), 7.45 (m, 3H), 1.10-0.93 (m, 15H); $^{13}$C NMR (125 MHz, CDCl$_3$) 145.6, 139.3, 135.4, 134.7, 133.7, 131.5, 126.5, 124.2, 123.7, 122.4, 122.2, 121.4, 7.4, 3.2. IR (Neat Film, NaCl) 3060, 2953, 2908, 2873, 1450, 1440, 1415, 1366, 1283, 1250, 1238, 1098, 1080, 1042, 1019, 1003, 972, 812, 749, 733 cm$^{-1}$; HRMS (EI+) calc'd for C$_{18}$H$_{22}$SSi [M.+]: 298.1212, found 298.1214. The HSQC spectrum of this reaction product has previously been reported in U.S. Pat. No. 9,000,167.

Example 6.9.47: Reaction of dibenzo[b,d]furan 3v with Et$_3$SiH

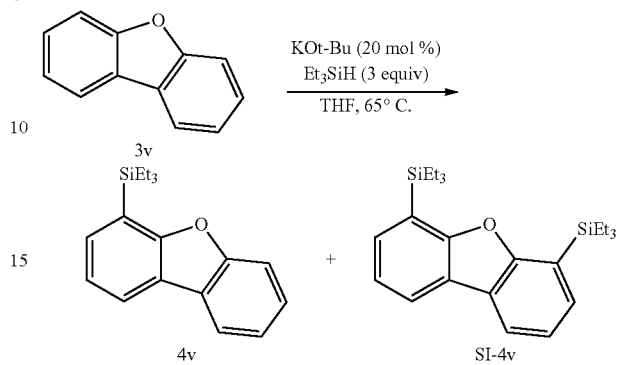

The reaction was conducted according to the General Procedure by heating KOt-Bu (11.2 mg, 0.1 mmol, 20 mol %), dibenzo[b,a]furan 3v (84.1 mg, 0.5 mmol, 1 equiv), Et$_3$SiH (243 μL, 1.5 mmol, 3 equiv), and 0.5 mL of THF at 65° C. for 65 h. Desired product 4v (100.2 mg, 71% yield) and bis-silylated product SI-4v (6.9 mg, 4% yield) were obtained after purification by silica gel flash chromatography (100% hexanes).

Dibenzo[b,d]furan-4-yltriethylsilane 4v: Colourless oil, Rf=0.6 (100% hexanes). $^1$H NMR (500 MHz, CDCl$_3$) δ 8.01-7.94 (m, 2H), 7.61-7.50 (m, 2H), 7.46 (td, J=7.7, 1.4 Hz, 1H), 7.34 (td, J=7.6, 4.4 Hz, 2H), 1.02 (m, 15H).

4,6-Bis(triethylsilyl)dibenzo[b,d]furan SI-4v: White solid, Rf=0.7 (100% hexanes). $^1$H NMR (500 MHz, CDCl$_3$) δ 7.99 (dd, J=7.6, 1.4 Hz, 2H), 7.54 (dd, J=7.1, 1.4 Hz, 2H), 7.35 (t, J=7.4 Hz, 2H), 1.12-0.96 (m, 30H).

Example 6.9.48:
Triethyl(6-methoxydibenzo[b,d]furan-4-yl)silane 4w

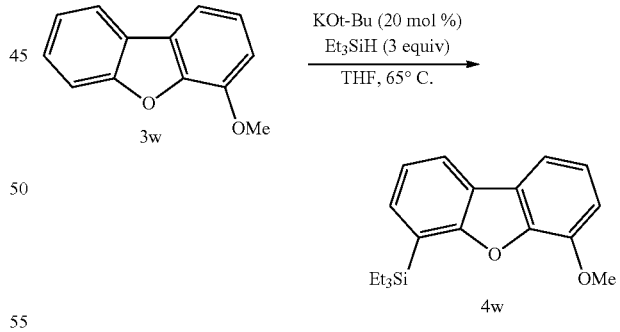

The reaction was conducted according to the General Procedure by heating KOt-Bu (11.2 mg, 0.1 mmol, 20 mol %), 4-methoxydibenzo[b,d]furan 3w (99.0 mg, 0.5 mmol, 1 equiv), Et$_3$SiH (243 μL, 1.5 mmol, 3 equiv), and 0.5 mL of THF at 65° C. for 65 h. The desired product 4w (99.9 mg, 64% yield) was obtained as a colorless oil after purification by silica gel flash chromatography (100% hexanes). Rf=0.3 (100% hexanes); $^1$H NMR (500 MHz, CDCl$_3$) δ 7.94 (dd, J=7.6, 1.4 Hz, 1H), 7.53 (ddd, J=15.4, 7.4, 1.2 Hz, 2H), 7.37-7.30 (m, 1H), 7.24 (t, J=7.8 Hz, 1H), 6.99 (dd, J=8.0, 1.0 Hz, 1H), 4.09 (s, 3H), 1.08-0.95 (m, 15H); $^{13}$C NMR (125 MHz, CDCl$_3$) δ 161.1, 45.7, 145.3, 133.4, 126.1, 123.0, 122.8, 122.3, 121.5, 120.4, 112.9, 111.0, 56.9, 7.4, 3.5; IR (Neat Film, NaCl) 3052, 2952, 2925, 2873, 2852, 2361, 1627, 1596, 1576, 1497, 1483, 1456, 1432, 1387, 1322, 1308, 1270, 1220, 1180, 1168, 1147, 1125, 1038, 1006, 854, 836, 767, 752, 729 cm$^{-1}$; HRMS (EI+) calc'd for C$_{19}$H$_{24}$O$_2$Si [M.+]: 312.1546, found 312.1555.

Example 6.9.49: Silylation of Pyridine

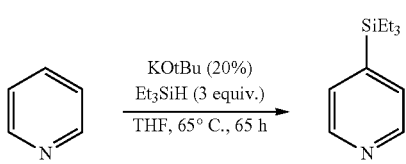

The reaction was conducted according to the General Procedure by heating pyridine (40 mg, 0.5 mmol, 1 equiv.), KOt-Bu (17 mg, 0.15 mmol, 0.3 equiv) and Et$_3$SiH (240 microliters, 1.5 mmol, 3 equiv.) in 1 mL of tetrahydrofuran for 65 hours at 65° C. After aqueous work up, the crude reaction mixture was purified by chromatography on silica using an 80:1:4 mixture of hexanes:diethyl ether:triethylamine respectively to obtain 14 mg (15%) of the title compound as a colourless oily solid. $^1$H NMR (500 MHz, THF-d$_8$) δ8.99-8.16 (m, 2H), 7.62-7.07 (m, 2H), 1.01-0.93 (m, 6H), 0.91-0.79 (m, 4H). $^{13}$C NMR (126 MHz, THF-d$_8$) δ 149.88, 129.76, 129.29, 7.70, 3.66. HRMS: [C$_{11}$H$_{20}$NSi] calculated 194.1365, measured 194.1367.

Attempts to reproduce this experiment resulted in variable yields for pyridine, typically yielding less than about 5% of the indicated product. Experiments with other electron-deficient heteroarenes, such as quinoline, isoquinoline, and acridine, under comparable conditions, likewise resulted either low yields (<5%) or no reaction.

Example 6.9.50: Attempted Silylation of 4-methoxypyridine

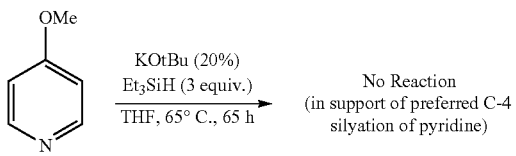

The reaction was conducted according to the General Procedure by heating 4-methoxypyridine (55 mg, 0.5 mmol, 1 equiv.), KOt-Bu (17 mg, 0.15 mmol, 0.3 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and $^1$H NMR analysis and revealed no apparent conversion of the starting material to silylated products.

Example 6.9.51: Attempted Silylation of 2,6 dimethoxypyridine

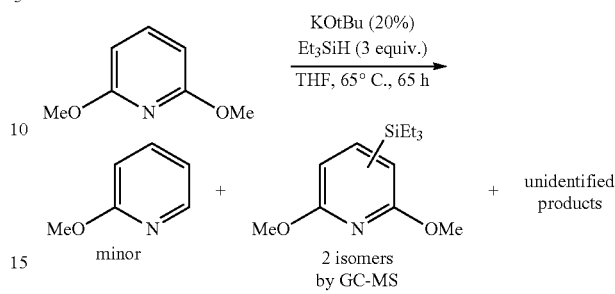

The reaction was conducted according to the General Procedure by heating 2,6-dimethoxypyridine (70 mg, 0.5 mmol, 1 equiv.), KOt-Bu (17 mg, 0.15 mmol, 0.3 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and $^1$H NMR analysis. GC-MS analysis revealed major mass peaks corresponding to the formation of 2 silylated product isomers as well as several unidentified products.

Example 7. Expanded Reactions Scenarios—Sensitivities of Substrates and Functional Group Tolerances The general and expansive utility of the present methods are already described herein, but for the sake of completeness, additional specific examples and reaction schemes are provided here. Also included are new methodologies for preparing and characterizing these materials.

Figure 2:
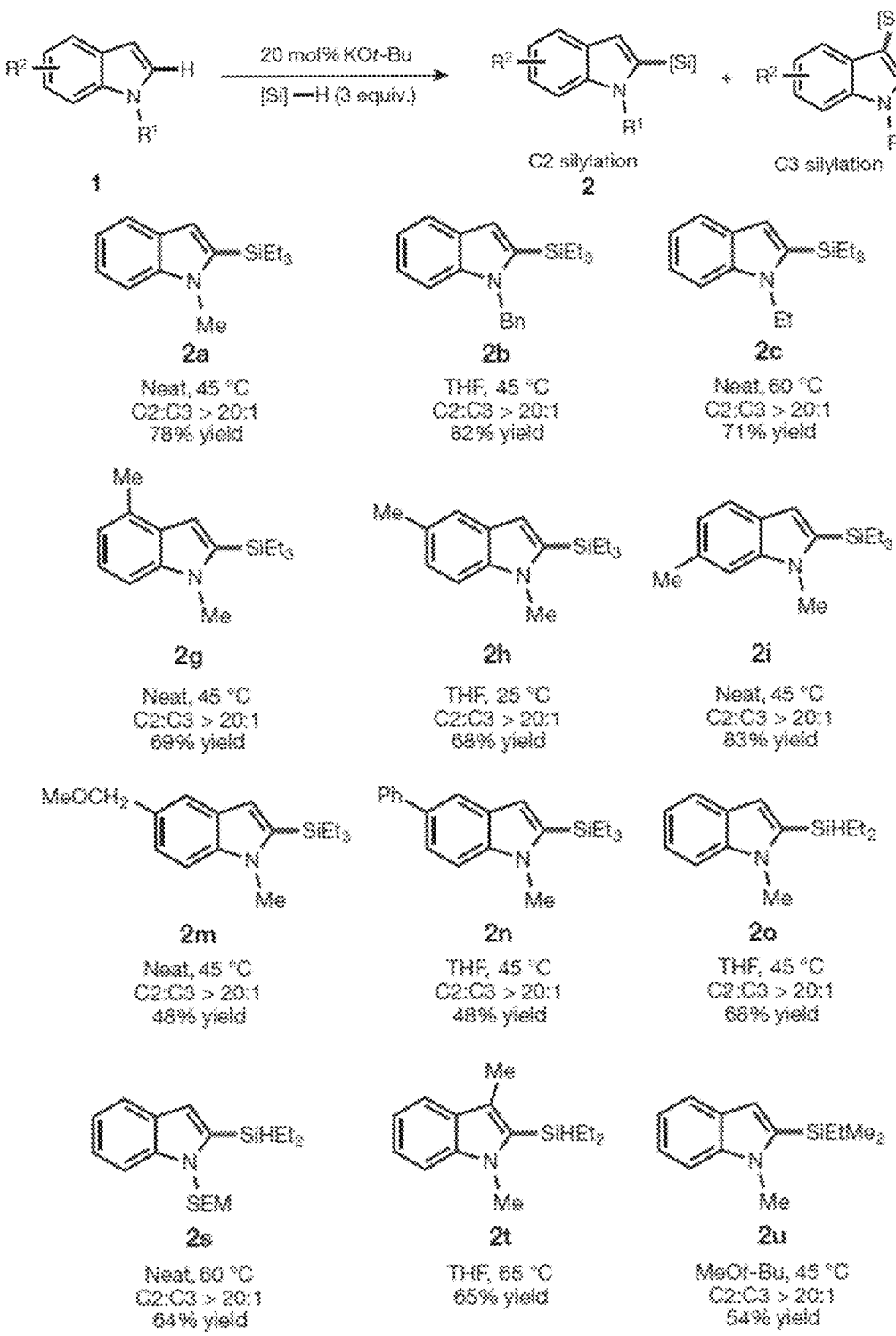
FIG. 2 illustrates the scope of base-catalysed silylation of indoles. In these examples, KO-t-Bu is used as an exemplary base. [Si]—H=Et$_3$SiH, Et$_2$SiH$_2$, EtMe$_2$SiH, PhMe$_2$SiH or n-Bu$_3$SiH, MOM, methoxymethyl; SEM, 2-[(trimethylsilyl)ethoxy]methyl.
Figure 2:
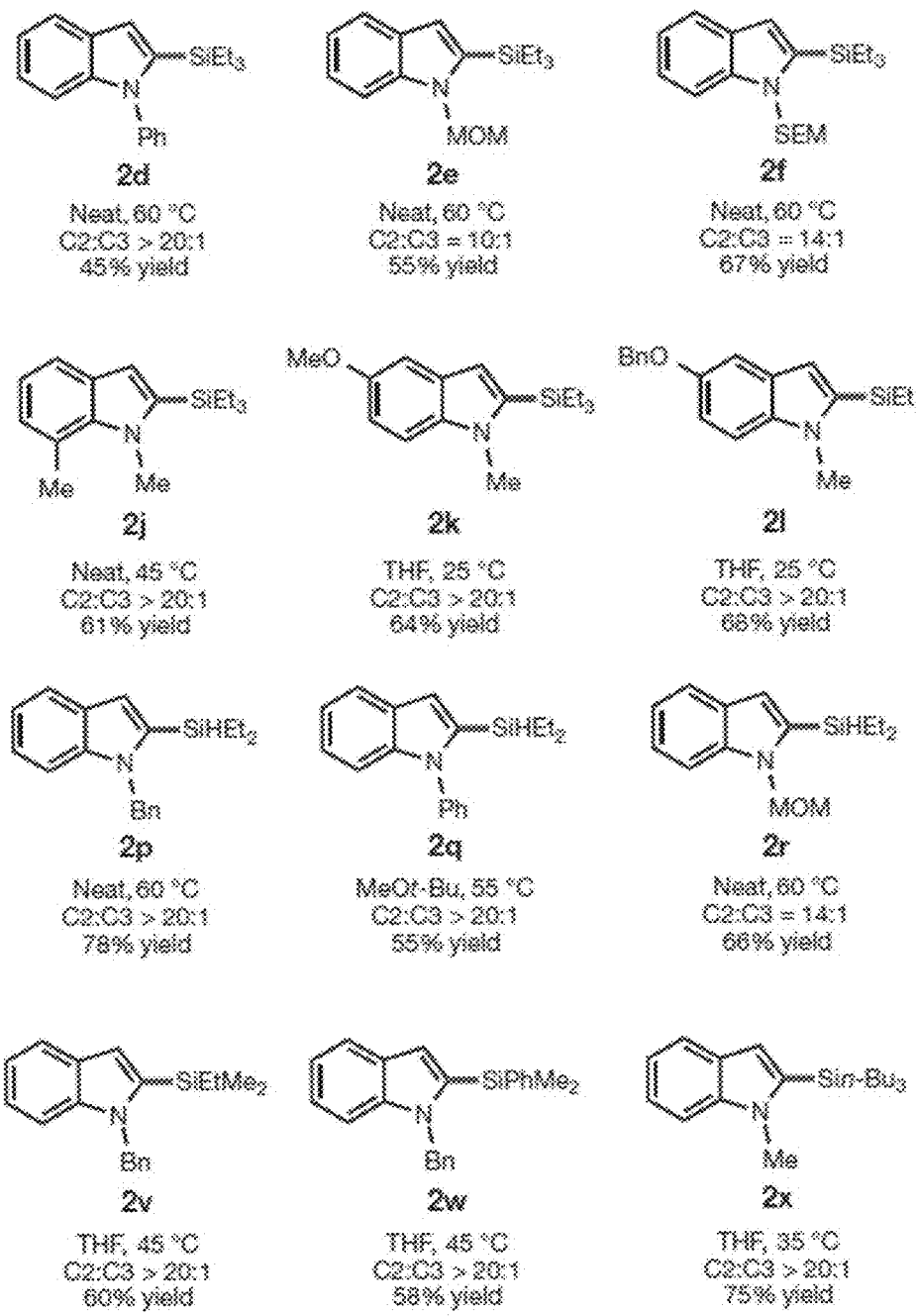
Figure 3:
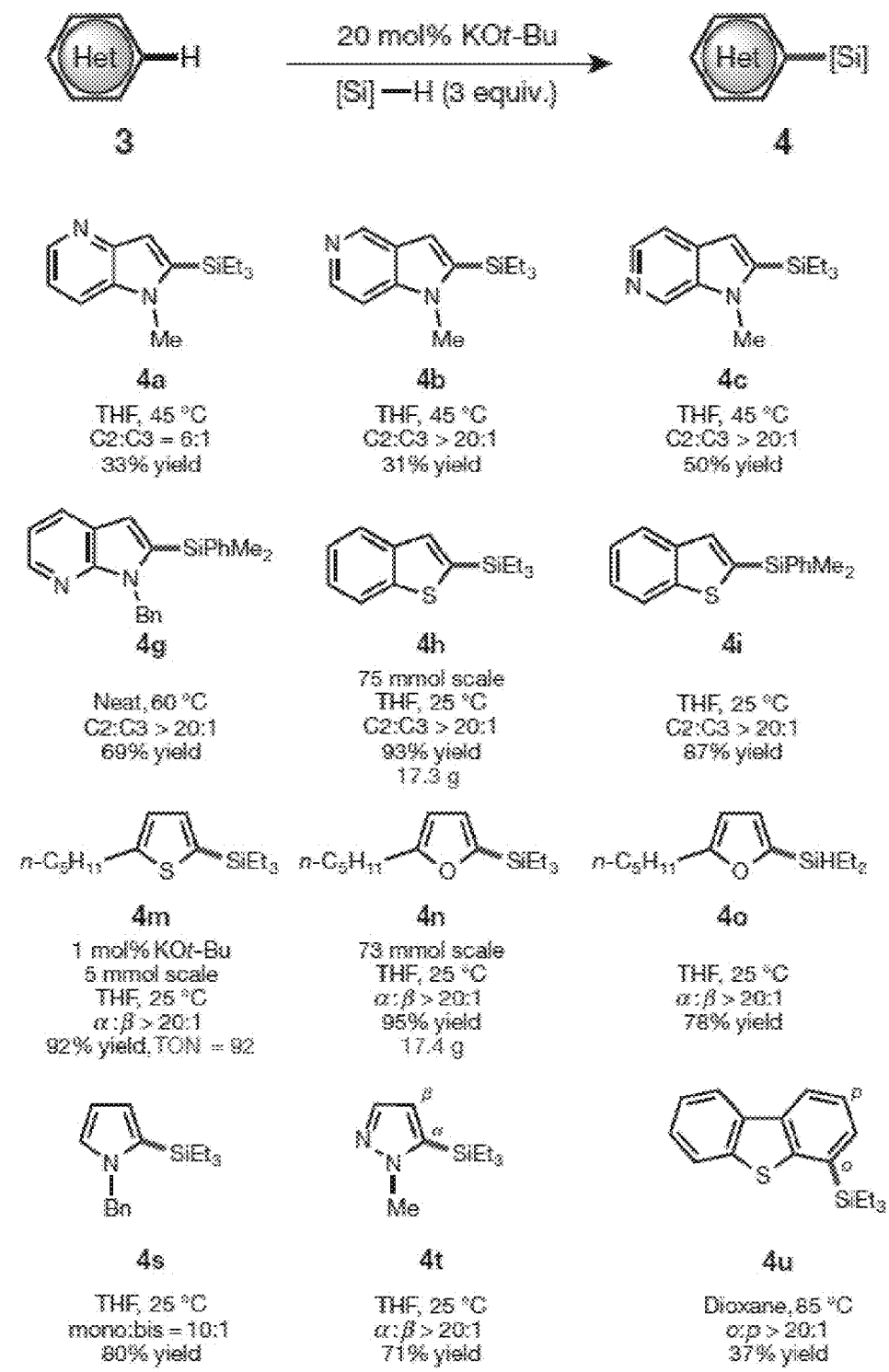
FIG. 3 illustrates the scope of base-catalysed silylation of N-, O- and S-containing heteroarenes. In these examples, KO-t-Bu is used as an exemplary base. See Example 6.9.1 to 6.9.51 for details. [Si]—H=Et$_3$SiH, Et$_2$SiH$_2$, EtMe$_2$SiH, PhMe$_2$SiH or n-Bu$_3$SiH.
Figure 3:
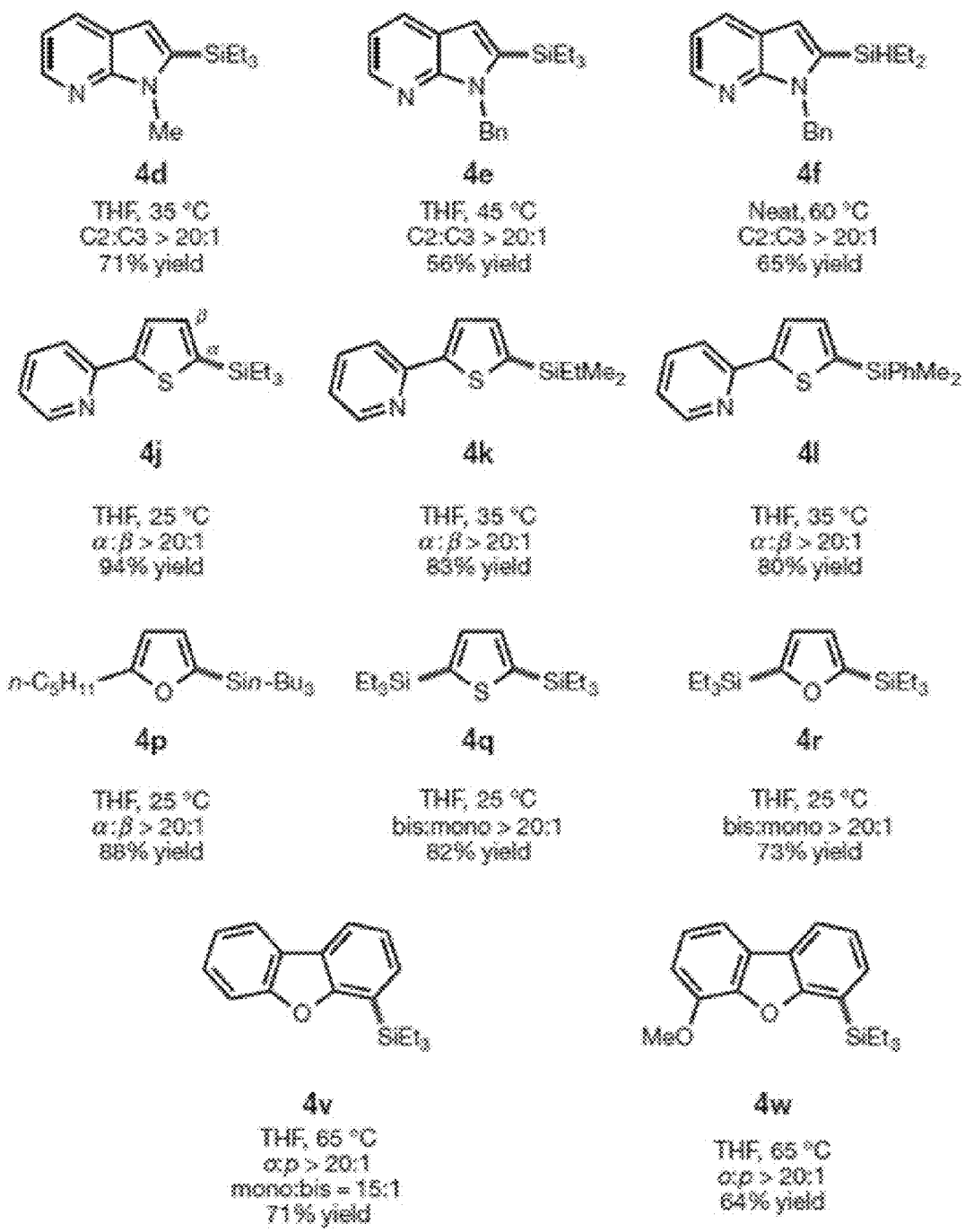

As an expansion to the earlier examples, a variety of indoles with Me, ethyl (Et), benzyl (Bn), phenyl (Ph) and the readily cleavable methoxylmethyl and 2-[(trimethylsilyl) ethoxy]methyl groups on nitrogen were evaluated and all led to regioselective C2 silylation in moderate to good yields (FIG. 2, compounds 2a-2f). Testing the influence of substituents at various positions of the indole nucleus showed that Me, OMe, OBn, CH$_2$OMe and Ph are all compatible, giving the desired products 2g-2n in 48%-83% yield. Several hydrosilanes were examined and the silylation products (2o-2x) were obtained in good yield. A diverse range of N-, O- and S-containing heteroaromatics (FIG. 3), including pyridine-containing scaffolds (4a-4g and 4j-4l), underwent the reaction with high regioselectivity. Reactions at decreased catalyst loadings (1-3.5 mol %; 4j, 4m and 4n) and on a large scale (4h and 4n) demonstrated the robustness and preparative scale utility of the process. The reaction scaled to greater than 100 g without loss of catalyst activity under procedurally convenient conditions (FIG. 4A). In general, the reaction proved to be selective for electron-neutral and electron-rich heterocycles; indoles possessing electron-withdrawing groups appeared to be unreactive.

Example 7.1. Competition Experiments with Thiophene, Furan and Pyrrole

To investigate the relative reactivities of nitrogen-, oxygen-, and sulfur-containing aromatic heterocycles by KOt-Bu-catalyzed C—H silylation, two internal competition experiments were conducted using one equivalent of Et$_3$SiH and one equivalent of each heteroarene (Scheme 1). Reactions were run to partial consumption of Et₃SiH and relative quantities of silylated heteroarene were determined by ¹H NMR analysis. Results demonstrated that for 5-membered heteroarenes, the relative rate of reactivity trends as: thiophene 3q>furan 3r>1-methylpyrrole 3x.

(a)

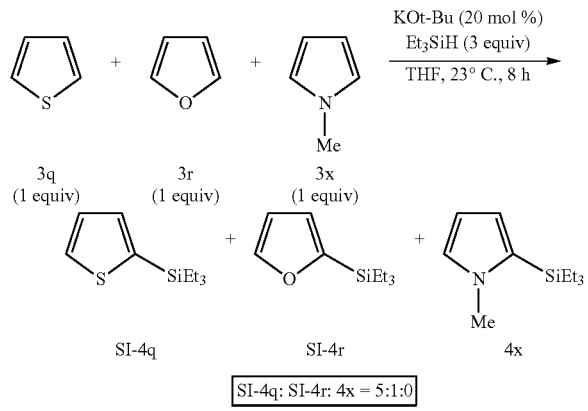

(b)

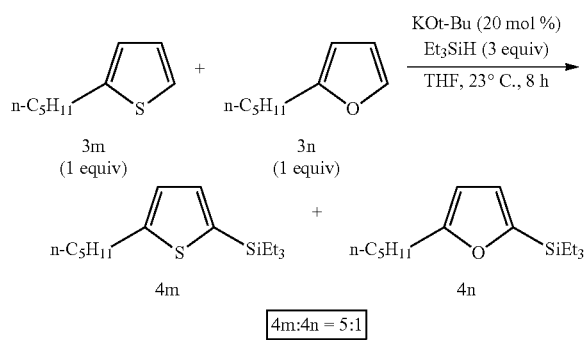

This trend was corroborated in the competition between substituted thiophene 3m and furan 3n. Procedures for competition experiments comprised:

For reaction (a): In a nitrogen-filled glove box, KOt-Bu (11.2 mg, 0.1 mmol, 20 mol %), thiophene 3g (42.1 mg, 0.5 mmol, 1 equiv), furan 3r (34.0 mg, 0.5 mmol, 1 equiv) and 1-methylpyrrole 3x (40.5 mg, 0.5 mmol, 1 equiv) were added to a 2 dram scintillation vial equipped with a magnetic stirring bar. THF (0.3 mL) and Et₃SiH (81 µL, 0.5 mmol, 1 equiv—filtered through a short pad of activated alumina before use) were then added. The vial was sealed and stirred at 23° C. for approximately 8 hours. The vial was removed from the glove box, diluted with diethyl ether (2 mL) and concentrated under reduced pressure. Analysis of the crude reaction mixture by ¹H NMR revealed that the ratio of SI-4q:SI-4r:4x was 5:1:0.

For reaction (b): In a nitrogen-filled glove box, KOt-Bu (11.2 mg, 0.1 mmol, 20 mol %), 2-pentylthiophene 3m (77.0 mg, 0.5 mmol, 1 equiv), and 2-pentylfuran 3n (69.1 mg, 0.5 mmol, 1 equiv) were added to a 2 dram scintillation vial equipped with a magnetic stirring bar, THF (0.3 mL) and Et₃SiH (81 µL, 0.5 mmol, 1 equiv—filtered through a short pad of activated alumina before use) were then added. The vial was sealed and stirred at 23° C. for approximately 8 hours. The vial was removed from the glove box, diluted with diethyl ether (2 mL) and concentrated under reduced pressure. Analysis of the crude reaction mixture by ¹H NMR revealed that the ratio of 4m:4n was 5:1.

Example 7.2. Evaluation of Functional Group Compatibilities

In order to provide a comprehensive treatment of functional group tolerance for the silylation reaction, a "robustness screen" as per the method of Glorius was performed (Table 5, which follows). Certain generalizations can be made from the results. For example, carbonyl groups shut down the reaction (entries 16, 17). Nevertheless, protection as an acetal, such as benzaldehyde dimethyl acetal is well tolerated (entry 18). Aryl-X groups where X=Br, I, CN, NO₂ likewise thwart the reactivity (entries 7, 8, 19 and 20). Intriguingly, these functional groups remain intact in most cases. However, alkene, alkyne, Ar—F, Ar—Cl, Ar—CF₃, tertiary amine, pyridine, and phosphine moieties are compatible (entries 2-6, 9, 11, 23-26). No obvious hydrosilylation or reduction of alkene and alkyne occurs. Even free OH and NH groups are tolerated to some extent presumably due to a fortuitous silylative protection of the heteroatom in situ, which was confirmed by using BnOTES as an additive (entries 12, 13, and 15). Moreover, epoxide and aziridine are tolerated as well and nucleophilic ring opening of these additives was not observed (entries 21, 22).

TABLE 5

| entry | additive (1.0 equiv) | 4 h yield (%) | 3 h remaining (%) | additive remaining (%) |
|---|---|---|---|---|
| 1[b] | — | 99 | 0 | — |
| 2 | C₆H₁₃—CH=CH—C₆H₁₃ | 95 | 0 | 95 |
| 3 | C₄H₉—CH=CH—C₄H₉ | 67 | 31 | 97 |
| 4 | C₃H₇—≡—C₃H₇ | 83 | 26 | 99 |
| 5 | PhF | 95 | 5 | N.D.[c] |
| 6 | PhCl | 74 | 25 | 100 |
| 7 | PhBr | 0 | 89 | 100 |
| 8 | PhI | 0 | 91 | 86 |
| 9 | PhCF₃ | 90 | 10 | N.D.[c] |
| 10 | PhNMe₂ | 80 | 20 | 79 |
| 11 | n-Bu₃N | 38 | 55 | 100 |
| 12 | morpholine | 19 | 73 | N.D.[c,d] |
| 13 | BnOH | 31 | 60 | 0[e] |
| 14 | PhOH | 0 | 63 | 91 |
| 15 | BnOTES | 60 | 37 | 89 |

TABLE 5-continued

[Reaction scheme: 3h (benzothiophene) + KOt-Bu (20 mol %), Et₃SiH (3 equiv), THF, 25° C., 43 h, additives → 4h (2-triethylsilyl benzothiophene)]

| entry | additive (1.0 equiv) | 4 h yield (%) | 3 h remaining (%) | additive remaining (%) |
|---|---|---|---|---|
| 16 | PhC(O)Ph | 0 | 83 | 91 |
| 17 | PhCO₂Me | 0 | 87 | 84 |
| 18 | PhCH(OMe)₂ | 82 | 0 | 50[f] |
| 19 | PhNO₂ | 0 | 86 | 98 |
| 20 | PhCN | 0 | 85 | 81 |
| 21 | cyclohexene oxide | 60 | 35 | 100 |
| 22 | N-(2-benzyloxyethyl)aziridine | 40 | 53 | 100 |
| 23 | pyridine | 71 | 28 | N.D.[c] |
| 24 | 2,2'-bipyridine | 47 | 50 | 100 |
| 25 | indole | 0 | 92 | 99 |
| 26 | PPh₃ | 48 | 50 | 97 |

[a]The reaction was performed with 0.5 mmol of 3 h and 0.5 mmol of additive under the general procedure. 0.5 mmol of tridecane was added as an internal standard at the start of the reaction. Yield of product, remaining amounts of 3 h and additive were determined by GC-FID analyse.
[b]Control reaction without the addition of additive.
[c]Not determined (overlapped with solvent peak due to the low boiling point).
[d]Triethyl silyl protected morpholine was formed and confirmed by GCMS analysis.
[e]BnOTES was formed.
[f]Acetal partially hydrolyzed to PhCHO.

Example 8. Transformations of the Prepared Silanes

Example 8.1. One-Pot Si-Directed ipso-Substitution/Suzuki-Miyaura Cross-Coupling

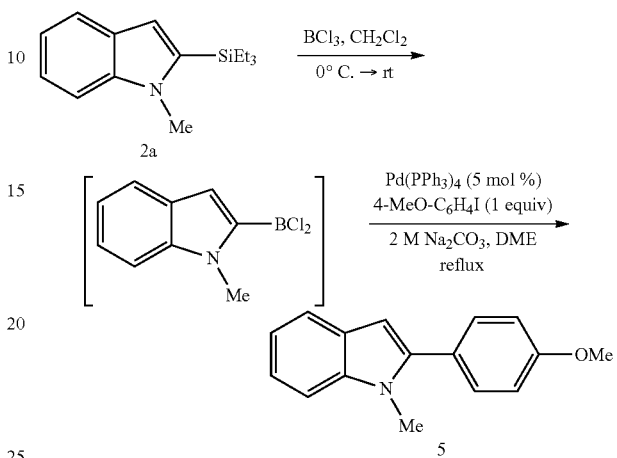

A solution of $BCl_3$ (1.0 M, 0.48 mL, 0.48 mmol) in $CH_2Cl_2$ was added by syringe under $N_2$ to a stirred solution of indolesilane 2a (98.2 mg, 0.4 mmol) in $CH_2Cl_2$ (4 mL) at 0° C. The mixture was stirred at room temperature for 3 h, after which time the solvent was removed in vacuo. After the residue was dried under high vacuum for 20 min, 4-iodo-anisole (94.0 mg, 0.4 mmol), Pd(PPh₃)₄ (23.2 mg, 5 mol %), DME (4 mL, degassed) and 2M $Na_2CO_3$ aqueous solution (1 mL, degassed) were added and the mixture was stirred under reflux for 5 h. Then the reaction mixture was cooled to room temperature and water (20 mL) was added. The mixture was extracted with Et2O (3×30 mL), the combined organic extracts were washed with brine, dried over $Na_2SO_4$ and concentrated. The desired 2-(4-methoxyphenyl)-1-methyl-1H-indole 5 (71.9 mg, 76% yield) was obtained as a white solid after purification by silica gel flash chromatography (gradient elution, 10→33% $CH_2Cl_2$ in hexanes). Rf=0.4 (10% EtOAc in hexanes); ¹H NMR (500 MHz, CDCl₃) δ 7.63 (d, J=7.7 Hz, 1H), 7.49-7.39 (m, 2H), 7.36 (d, J=8.2 Hz, 1H), 7.24 (dt, J=8.2, 1.2 Hz, 1H), 7.14 (dt, J=7.9, 1.0 Hz, 1H), 7.05-6.96 (m, 2H), 6.51 (br s, 1H), 3.88 (s, 3H), 3.73 (s, 3H).

Example 8.2. Synthesis of a Heteroarylsilanol and Application in Denmark-Hiyama Crosscoupling

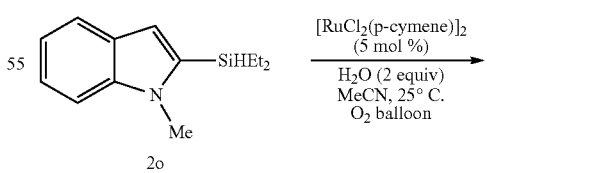

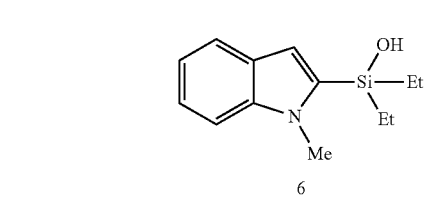

Compound 2o (44.5 mg, 0.2 mmol) and [RuCl$_2$(p-cymene)]$_2$ (6.3 mg, 0.01 mmol) were added to a 5 mL flask equipped with a stirring bar. The flask was sealed with a septum and placed under high vacuum for 5 min before being connected with an O$_2$ balloon and back-filled with O$_2$, then acetonitrile (1 mL) and H$_2$O (7.4 µL, 0.4 mmol) were added by syringe through the septum. The reaction mixture was stirred for 12 h at room temperature. The solvent was evaporated and the product 6 (36.0 mg, 77% yield) was obtained as a colorless oil after purification by silica gel flash chromatography (gradient elution, 10→20% EtOAc in hexanes). Rf=0.2 (10% EtOAc in hexanes); $^1$H NMR (500 MHz, CDCl$_3$) δ 7.66 (dt, J=7.9, 1.0 Hz, 1H), 7.37 (dd, J=8.3, 1.0 Hz, 1H), 7.28 (ddd, J=8.3, 6.9, 1.2 Hz, 1H), 7.13 (ddd, J=7.9, 6.9, 1.0 Hz, 1H), 6.80 (d, J=0.9 Hz, 1H), 3.93 (s, 3H), 2.12 (br s, 1H), 1.12-1.05 (m, 6H), 1.02-0.95 (m, 4H); $^{13}$C NMR (125 MHz, CDCl$_3$) δ 140.4, 138.1, 128.4, 122.6, 121.1, 119.4, 112.7, 109.4, 33.1, 7.1, 6.7. IR (Neat Film, NaCl) 3315, 2956, 2876, 1493, 1463, 1413, 1357, 1328, 1300, 1234, 1166, 1102, 1075, 1007, 960, 897, 839, 798, 751, 732 cm$^{-1}$; HRMS (MM: ESI-APCI+) calc'd for C$_{13}$H$_{20}$NOSi [M+H]+: 234.1309, found 234.1305.

Example 8.3. 2-(4-Methoxyphenyl)-1-methyl-1-Indole 5

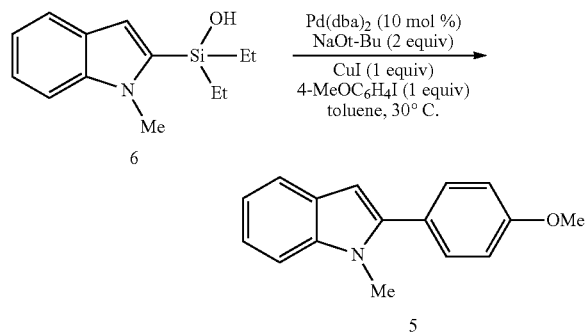

In a nitrogen-filled glovebox, a 2 dram vial equipped with a stir bar was charged with NaOt-Bu (26.8 mg, 0.28 mmol) and CuI (26.6 mg, 0.14 mmol), 4-iodoanisole (33.0 mg, 0.14 mmol), Pd(dba)$_2$ (8.2 mg, 0.014 mmol, 10 mol %) and 0.2 mL of toluene. The mixture was sealed with a cap and stirred for 10 min. Then this mixture was transferred by syringe to another 2 dram vial containing silanol 6 (33.1 mg, 0.14 mmol). The vial was washed with toluene (2×0.4 mL) and that rinse was added to the reaction mixture. After the reaction was stirred at 30° C. for 4 h, the starting material was completely converted (monitored by TLC). The desired product 5 (28.1 mg, 84% yield) was obtained as a white solid after purification by silica gel flash chromatography (gradient elution, 10→50% CH$_2$Cl$_2$ in hexanes).

Example 8.4. Direct C7 Lithiation-Borylation by a Si-Blocking Group Strategy This general transformation (i.e., the protection/deprotection of the C2 position in benzofurans, indoles, and thiophenes, including the C7 lithiation-borylation of these silylated derivatives) is considered within the scope of the present invention.

Example 8.4.1. Triethyl(7-(4,4,5,5-tetramethyl-1,3,2-dioxaborolan-2-yl)benzo[b]thiophen-2-yl)silane 7

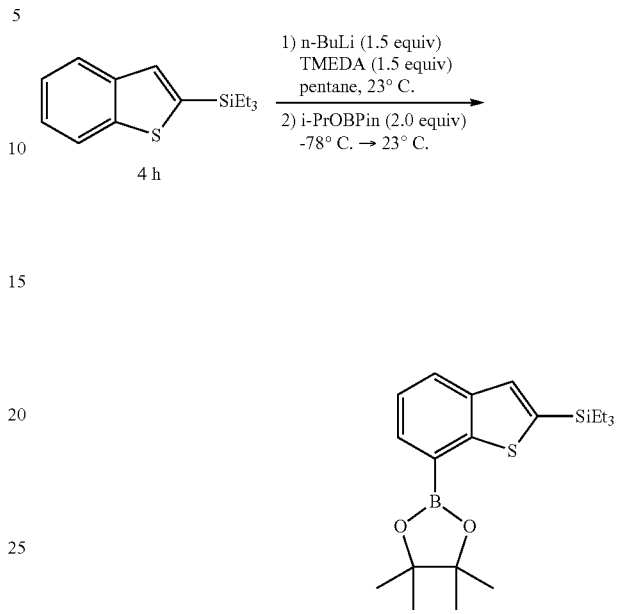

To a flame-dried, round bottom flask charged with a stir bar, capped with a septum and under a steady stream of argon was added benzo[b]thiophen-2-yltriethylsilane 4h (992 mg, 4.0 mmol, 1 equiv), pentane (5.0 mL) and TMEDA (0.703 g, 0.907 mL, 1.5 equiv) at 23° C. n-Butyllithium (1.6 M in hexanes, 3.78 mL, 1.5 equiv) was added dropwise such that the internal temperature remained between 22 and 25° C. (a thermocouple was inserted through the septum directly into the solution for internal monitoring of the temperature). The resultant dark brown solution was allowed to stir at 22° C. for 20 h. The solution was then cooled to −78° C. (dry ice/acetone) and i-PrOBPin (1.52 g, 1.64 mL, 8.06 mmol, 2.0 equiv) was added as a 1 M solution in THF (8.06 mL) dropwise such that the temperature was kept below −75° C., (careful temperature control is crucial for reproducibility). The resulting solution was allowed to stir for 1 h at −78° C. after which time the cooling bath was removed. The solution was allowed to naturally warm to 23° C. and stirred at that temperature for an additional hour. The resulting turbid yellow reaction mixture was carefully quenched with NH$_4$Cl (5 mL). The mixture was extracted with Et$_2$O (3×10 mL), the combined organic fractions were washed with brine, dried over MgSO$_4$, filtered, and the solvent was evaporated to give a viscous brown liquid. The desired product 7 (926 mg, 64% yield) was obtained as a colorless solid after purification by silica gel flash chromatography (gradient elution 0→3% EtOAc in hexanes). Rf=0.2 (100% hexanes); $^1$H NMR (500 MHz, CDCl$_3$) δ 7.91 (dd, J=8.0, 11.3 Hz, 1H), 7.80 (dd, J=7.0, 11.3 Hz, 1H), 7.48 (s, 1H), 7.35 (dd, J=7.9, 7.0 Hz, 1H), 1.42 (s, 12H), 1.10-1.00 (m, 914), 0.89 (m, 6H); $^{13}$C NMR (125 MHz, CDCl$_3$) δ 149.7, 140.8, 139.8, 132.0, 131.4, 126.4, 123.4, 84.3, 25.1, 7.6, 4.4. IR (Neat Film, NaCl) 2955, 2937, 1375, 1367, 1359, 1134, 1059, 854, 735 cm$^{-1}$; HRMS (EI+) calc'd for C$_{20}$H$_{31}$BSSiO$_2$ [M.+]: 374.1907, found 374.1907.

Example 8.4.2. 2-(Benzo[b]thiophen-7-yl)-4,4,5,5-tetramethyl-1,3,2-dioxaborolane 8

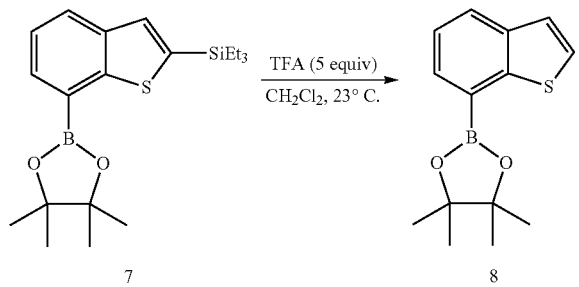

To a vial charged with a magnetic stirbar and triethyl(7-(4,4,5,5-tetramethyl-1,3,2-dioxaborolan-2-yl)benzo[b]thiophen-2-yl)silane 7 (300 mg, 0.80 mmol) was added $CH_2Cl_2$ (0.3 mL) and trifluoroacetic acid (306 μL, 4.0 mmol, 5.0 equiv) at room temperature. The reaction was allowed to stir for 3 hours, after which time the mixture was quenched with water (0.5 mL), extracted with $Et_2O$ (3×5 mL) and the combined organic fractions were washed with brine (5 mL). The solvents were removed to give 8 (203.8 mg, 98%) as a white solid without further purification. Rf=0.4 (3% EtOAc in hexanes); $^1$H NMR (500 MHz, $CDCl_3$) δ 7.92 (dd, J=7.9, 1.3 Hz, 1H), 7.83 (dd, J=7.1, 1.3 Hz, 1H), 7.48 (d, J=5.5 Hz, 1H), 7.38 (dd, J=7.9, 7.0 Hz, 1H), 7.34 (d, J=5.5 Hz, 1H), 1.41 (s, 12H); $^{13}$C NMR (125 MHz, $CDCl_3$) δ 145.8, 139.4, 132.0, 127.5, 126.7, 123.7, 123.4, 84.4, 25.1. IR (Neat Film, NaCl) 2977, 1564, 1504, 1461, 1372, 1330, 1300, 1267, 1199, 1165, 1135, 1097, 1038, 969, 851, 829, 801, 714, 672 $cm^{-1}$; HRMS (EI+) calc'd for $C_{14}H_{17}BSO_2$ [M.+]: 260.1042, found 260.1039.

Example 8.5. Synthesis of a Sila-Heterocycle by Inter-/Intramolecular Double C—H Silylation: 9,9-Diethyl-9H-benzo[d]pyrrolo[1,2-a][1,3]azasilole 9

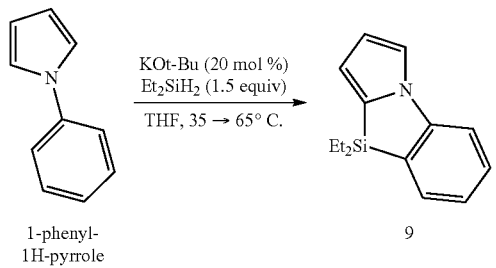

The reaction was conducted according to the General Procedure by heating KOt-Bu (11.2 mg, 0.1 mmol, 20 mol %), 1-phenyl-1H-pyrrole (72.0 mg, 0.5 mmol, 1 equiv), Et2SiH2 (97 μL, 0.75 mmol, 1.5 equiv), and 0.5 mL of THF at 35° C. for 72 h and then at 65° C. for 72 h. The desired product 9 (48.8 mg, 43% yield) was obtained as colorless needles after purification by silica gel flash chromatography (100% hexanes). Rf=0.6 (100% hexanes); $^1$H NMR (500 MHz, $CDCl_3$) δ 7.51 (ddd, J=7.1, 1.4, 0.6 Hz, 1H), 7.46-7.33 (m, 2H), 7.31 (dt, J=7.9, 0.7 Hz, 1H), 7.09 (td, J=7.2, 1.0 Hz, 1H), 6.52 (dd, J=3.3, 1.0 Hz, 1H), 6.41 (dd, J=3.3, 2.6 Hz, 1H), 1.05-0.96 (m, 6H), 0.96-0.79 (m, 4H); $^{13}$C NMR (125 MHz, $CDCl_3$) δ 148.0, 134.1, 130.8, 129.4, 128.5, 123.9, 117.5, 117.1, 113.3, 111.6, 7.5, 4.4; IR (Neat Film, NaCl) 2958, 2921, 2873, 2849, 1658, 1598, 1462, 1471, 1451, 1377, 1332, 1260, 1086, 1017, 799, 755, 717 $cm^{-1}$; HRMS (FAB+) calc'd for $C_{14}H_{18}NSi$ [M+H]+: 228.1208, found 228.1206. The HSQC spectrum of this reaction product has previously been reported in U.S. Pat. No. 9,000,167.

Example 8.6. C—H Silylation of Terthiophene

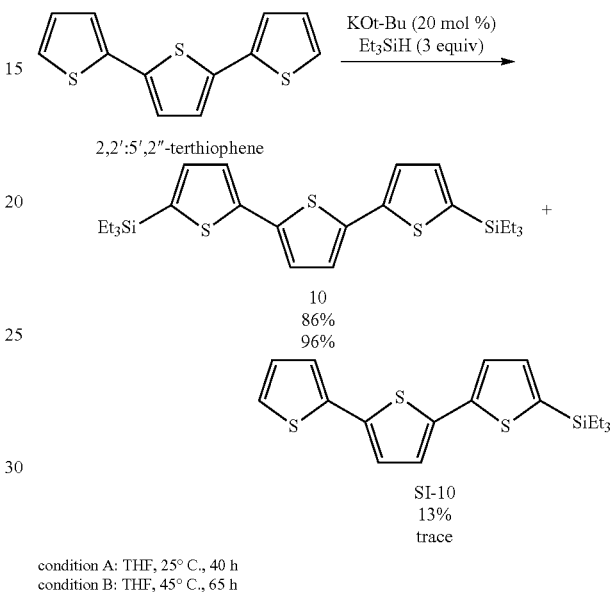

condition A: THF, 25° C., 40 h
condition B: THF, 45° C., 65 h

The reaction was conducted according to the General Procedure. For condition A: The reaction was performed with KOt-Bu (11.2 mg, 0.1 mmol, 20 mol %), 2,2':5',2"-terthiophene (124 mg, 0.5 mmol, 1 equiv), $Et_3SiH$ (243 μL, 1.5 mmol, 3 equiv), and 0.5 mL of THF at 25° C. for 40 h. Products 10 (204.7 mg, 86% yield) and SI-10 (23.5 mg, 13% yield) were obtained after purification by silica gel flash chromatography (100% hexanes). For condition B: The reaction was performed with KOt-Bu (11.2 mg, 0.1 mmol, 20 mol %), 2,2':5',2"-terthiophene (124 mg, 0.5 mmol, 1 equiv), $Et_3SiH$ (243 μL, 1.5 mmol, 3 equiv), and 0.5 mL of THF at 45° C. for 65 h. Product 10 (228.6 mg, 96% yield) was obtained after purification by silica gel flash chromatography (100% hexanes); SI-10 was observed as a trace product by $^1$H NMR and GC-MS, but was not isolated.

5,5"-Bis(triethylsilyl)-2,2':5',2"-terthiophene 10: Yellow oil, Rf=0.5 (100% hexanes); $^1$H NMR (500 MHz, $CDCl_3$) δ 7.25 (d, J=3.5 Hz, 2H), 7.14 (d, J=3.5 Hz, 2H), 7.10 (s, 2H), 1.03 (m, 18H), 0.82 (m, 12H). $^{13}$C NMR (125 MHz, $CDCl_3$) δ 142.4, 136.7, 136.5, 135.7, 124.9, 124.5, 7.2, 4.4; IR (Neat Film, NaCl) 3057, 2953, 2934, 2908, 2874, 1750, 1455, 1428, 1417, 1377, 1303, 1236, 1212, 1198, 1068, 988, 1009, 911, 892, 792, 736, 723 $cm^{-1}$; HRMS (EI+) calc'd for $C_{24}H_{36}S_3Si_2$ [M.+]: 476.1518, found 476.1534.

[2,2':5',2"-Terthiophen]-5-yltriethylsilane SI-10: Yellow oil, Rf=0.4 (100% hexanes); $^1$H NMR (500 MHz, $CDCl_3$) δ 7.24 (d, J=3.4 Hz, 1H), 7.21 (dd, J=5.1, 1.2 Hz, 1H), 7.17 (dd, 3.6, 1.2 Hz, 1H), 7.14 (dd, J=3.4, 1.6 Hz, 1H), 7.09 (q, J=3.7 Hz, 2H), 7.02 (dd, J=5.1, 3.6 Hz, 1H), 1.07-0.98 (m, 9H), 0.82 (qd, J=7.8, 0.9 Hz, 6H); $^{13}$C NMR (125 MHz, $CDCl_3$) δ 142.3, 137.5, 136.8, 136.6, 136.4, 135.6, 128.0, 125.0, 124.6, 124.5, 124.5, 123.8, 7.5, 4.6; IR (Neat Film, NaCl) 3068, 2953, 2873, 1458, 1425, 1377, 1235, 1195, 1069, 1011, 989, 913, 865, 836, 793, 737 cm$^{-1}$; HRMS (FAB+) calc'd for $C_{18}H_{23}S_3Si$ [M+H]+: 363.0731, found 363.0742.

Example 8.7. C—H Silylation of EDOT: (2,3-Dihydrothieno[3,4-b][1,4]dioxin-5-yl)triethylsilane 11

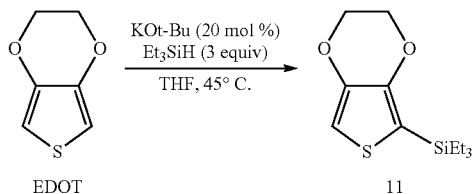

The reaction was conducted according to the General Procedure by heating KOt-Bu (11.2 mg, 0.1 mmol, 20 mol %), EDOT (2,3-dihydrothieno[3,4-b][1,4]dioxine, 71.1 mg, 0.5 mmol), Et$_3$SiH (240 μL, 1.5 mmol, 3 equiv), and 0.5 mL of THF at 45° C. for 72 h. The desired product 11 (79.3 mg, 62% yield) was obtained after purification by silica gel flash chromatography (gradient elution, 0→5% EtOAc in hexanes) as a cloudy yellow oil. Rf=0.3 (100% hexanes); $^1$H NMR (500 MHz, CDCl$_3$) δ 6.56 (s, 2H), 4.17 (s, 4H), 0.98 (td, J=7.8, 0.8 Hz, 9H), 0.84-0.74 (m, 6H); $^{13}$C NMR (125 MHz, CDCl$_3$) δ 147.5, 142.5, 108.7, 105.0, 64.5, 64.5, 7.4, 3.9; IR (Neat Film NaCl) 2952, 2873, 1468, 1440, 1422, 1361, 1244, 1181, 1151, 1072, 1042, 1009, 899, 721 cm$^{-1}$; HRMS (EI+) calc'd for $C_{12}H_{21}O_2SSi$ [M+H]+: 257.1032, found 257.1064.

Example 8.8. Late Stage Silylation of Active Pharmaceutical Ingredients (APIs)

Example 8.8.1. 1-Methyl-N-phenyl-N-((5-(triethylsilyl)thiophen-2-yl)methyl)piperidin-4-amine 12

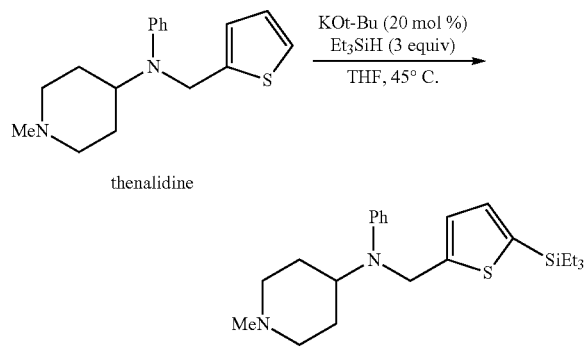

The reaction was conducted according to the General Procedure by heating KOt-Bu (2.2 mg, 0.02 mmol, 20 mol %), thenalidine (28.2 mg, 0.1 mmol, 1 equiv), Et$_3$SiH (48 μL, 0.3 mmol, 3 equiv), and 0.1 mL of THF at 45° C. for 72 h. The desired product 12 (24.9 mg, 62% yield) was obtained as a colorless oil after purification by silica get flash chromatography (hexanes:EtOAc:Et$_3$N=100:100:1). Rf=0.2 (hexanes:EtOAc:Et$_3$N=20:20:1); $^1$H NMR (500 MHz, CDCl$_3$) δ 7.24-7.17 (m, 2H), 7.05 (d, J=3.4 Hz, 1H), 6.97 (d, J=3.3 Hz, 1H), 6.82 (dt, J=7.8, 1.0 Hz, 2H), 6.72 (tt, J=7.2, 1.0 Hz, 1H), 4.62 (s, 2H), 3.70 (tt, J=11.6, 4.0 Hz, 1H), 2.96-2.92 (m, 2H), 2.30 (s, 3H), 2.07 (td, J=11.9, 2.5 Hz, 2H), 1.93-1.85 (m, 2H), 1.85-1.73 (m, 2H), 0.97 (t, J=7.9 Hz, 9H), 0.76 (q, J=7.8 Hz, 6H); $^{13}$C NMR (125 MHz, CDCl$_3$) δ 151.0, 149.0, 135.2, 134.7, 129.3, 125.3, 117.3, 113.8, 55.8, 55.6, 46.4, 46.0, 29.6, 7.5, 4.6. IR (Neat Film, NaCl) 2951, 2873, 2780, 2734, 1597, 1574, 1503, 1459, 1377, 1352, 1278, 1237, 1207, 1131, 1068, 1008, 987, 850, 802, 745 cm$^{-1}$; HRMS (MM: ESI-APC+) calc'd for $C_{23}H_{37}N_2SSi$ [M+H]+: 401.2441, found 401.2460.

Example 8.8.2: 5-(2-Chlorobenzyl)-2-(triethylsilyl)-4,5,6,7-tetrahydrothieno[3,2-c]pyridine 13a

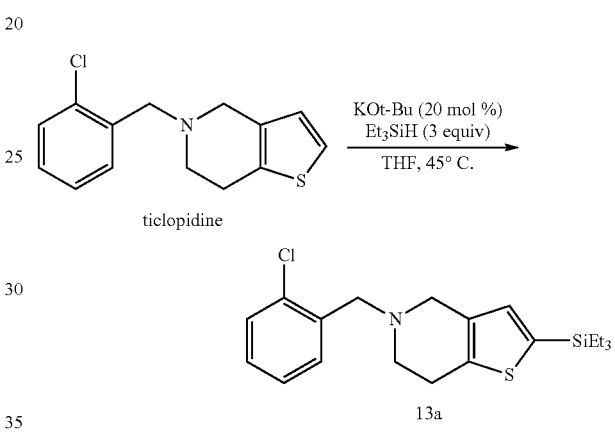

The reaction was conducted according to the General Procedure by heating KOt-Bu (11.2 mg, 0.1 mmol, 20 mol %), ticlopidine (132.5 mg, 0.5 mmol, 1 equiv), Et$_3$SiH (243 μL, 1.5 mmol, 3 equiv), and 0.5 mL of THF at 45° C. for 48 h. The desired product 13a (107.7 mg, 57% yield) was obtained as a colorless oil after purification by silica gel flash chromatography (gradient elution, Et$_2$O in hexanes), Rf=0.4 (10% Et$_2$O in hexanes); $^1$H NMR (500 MHz, CDCl$_3$) δ 7.56 (dd, J=7.5, 1.8 Hz, 1H), 7.37 (dd, J=7.8, 1.5 Hz, 1H) 7.25 (td, J=7.4, 1.5 Hz, 1H), 7.20 (td, J=7.6, 1.9 Hz, 1H), 6.86 (s, 1H), 3.84 (s, 2H), 3.67 (d, 1.6 Hz, 2H), 2.94 (t, J=5.9 Hz, 2H), 2.87 (t, J=5.4 Hz, 2H), 1.02-0.98 (m, 9H), 0.80-0.74 (m, 6H); $^{13}$C NMR (125 MHz, CDCl$_3$) δ 139.2, 136.5, 135.6, 134.4, 134.0, 133.2, 130.8, 129.6, 128.3, 126.8, 58.7, 53.3, 51.0, 26.1, 7.5, 4.6. IR (Neat Film, NaCl) 2952, 2908, 2873, 2805, 2763, 1462, 1443, 1413, 1375, 1360, 1347, 1303, 1289, 1234, 1169, 1125, 1106, 1047, 1032, 1018, 991, 907, 835, 752 cm$^{-1}$; HRMS (MM: ESI-APCI+) calc'd for $C_{20}H_{29}ClNSSi$ [M+H]+: 378.1473, found 378.1480.

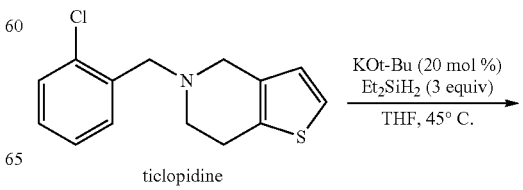

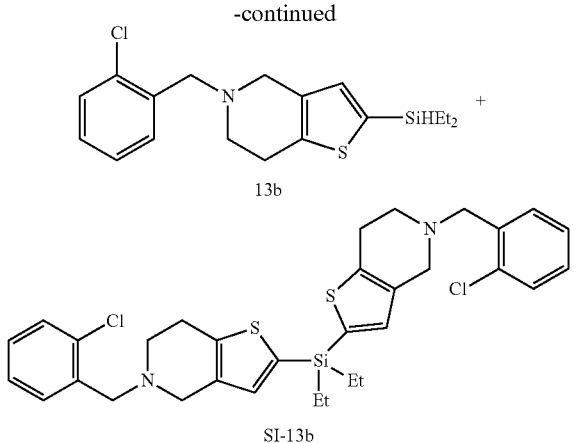

The reaction was conducted according to the General Procedure by heating KOt-Bu (11.2 mg, 0.1 mmol, 20 mol %), ticlopidine (134.5 mg, 0.5 mmol, 1 equiv), Et₃SiH₂ (194 μL, 1.5 mmol, 3 equiv), and 0.5 mL of THF at 45° C. for 108 h. Products 13b (97.9 mg, 56% yield) and SI-13b (27.3 mg, 18% yield) were obtained after purification by silica gel flash chromatography (gradient elution, 5→50% Et₂O in hexanes).

5-(2-Chlorobenzyl)-2-(diethylsilyl)-4,5,6,7-tetrahydrothieno[3,2-c]pyridine 13b: Colorless oil, Rf=0.4 (10% Et₂O in hexanes); ¹H NMR (500 MHz, CDCl₃) 7.56 (dd, J=7.6, 1.8 Hz, 1H), 7.38 (dd, J=7.8, 1.4 Hz, 1H), 7.26 (td, J=7.4, 1.5 Hz, 1H), 7.21 (td, J=7.6, 1.9 Hz, 1H), 6.93 (s, 1H), 4.30 (p, J=3.2 Hz, 1H), 3.84 (s, 2H), 3.67 (t, =1.7 Hz, 2H), 2.96-2.94 (m, 2H), 2.88-2.85 (m, 2H), 1.05 (t, J=7.8 Hz, 6H), 0.83 (qd, J=7.5, 3.3 Hz, 4H); ¹³C NMR (125 MHz, CDCl3) δ 140.0, 136.4, 135.9, 134.4, 134.2, 131.3, 130.8, 129.6, 128.3, 126.8, 58.6, 53.2, 50.9, 26.1, 8.1, 4.5. IR (Neat Film, NaCl) 2953, 2909, 2872, 2805, 2112, 1456, 1447, 1361, 1348, 1303, 1290, 1231, 1169, 1125, 1106, 1048, 1033, 1009, 992, 907, 810, 752 cm⁻¹; HRMS (MM: ESI-APCI+) calc'd for C₁₈H₂₅ClNSSi [M+H]+: 350.1160, found 350.1155.

Bis(5-(2-chlorobenzyl)-4,5,6,7-tetrahydrothieno[3,2-c]pyridin-2-yl)diethylsilane SI-13b: Colorless oil, Rf=0.3 (50% Et₂O in hexanes); ¹H NMR (500 MHz, CDCl₃) δ 7.55 (dd, J=7.6, 1.8 Hz, 2H), 7.37 (dd, J=7.8, 1.5 Hz, 2H), 7.25 (td, J=7.4, 1.5 Hz, 2H), 7.20 (td, J=7.6, 1.9 Hz, 2H), 6.92 (s, 2H), 3.83 (s, 4H), 3.65 (t, J=3.3 Hz, 4H), 2.94 (t, J=5.4 Hz, 4H), 2.86 (t, J=5.6 Hz, 4H), 1.09-0.95 (m, 10H); ¹³C NMR (125 MHz, CDCl₃) δ 140.2, 136.4, 135.8, 134.53, 134.45, 132.4, 130.9, 129.6, 128.3, 126.8, 58.7, 53.2, 50.9, 26.1, 7.5, 6.5. IR (Neat Film, NaCl) 3059, 2953, 2913, 2868, 2806, 1471, 1453, 1446, 1361, 1289, 1125, 1105, 1033, 989, 907, 839, 805, 753 cm⁻¹; HRMS (MM: ESI-APCI+) calc'd for C₃₂H₃₇Cl₂N₂S₂Si [M+H]+: 611.1539, found 611.1523.

Example 8.8.3. 5-(2-Chlorobenzyl)-2-(dimethyl(phenyl)silyl)-4,5,6,7-tetrahydrothieno[3,2-c]pyridine 13c

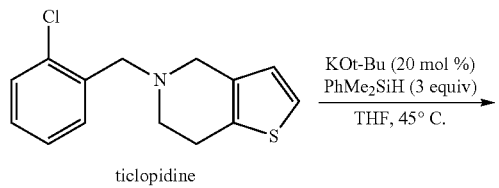

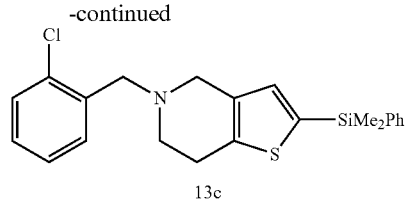

The reaction was conducted according to the General Procedure by heating KOt-Bu (11.2 mg, 0.1 mmol, 20 mol %), ticlopidine (134.5 mg, 0.5 mmol, 1 equiv), PhMe₂SiH (230 μL, 1.5 mmol, 3 equiv), and 0.5 mL of THF at 45° C. for 108 h. Product 13c (135.4 mg, 68% yield) was obtained as a colorless oil after purification by silica gel flash chromatography (3% Et₂O in hexanes). Rf=0.3 (10% Et₂O in hexanes); ¹H NMR (500 MHz, CDCl₃) δ 7.58-7.52 (m, 3H), 7.39-7.34 (m, 4H), 7.25-7.18 (m, 2H), 6.87 (s, 1H), 3.82 (s, 2H), 3.64 (t, J=1.7 Hz, 2H), 2.95-2.92 (m, 2H), 2.88-2.84 (m, 2H), 0.56 (s, 6H); ¹³C NMR (125 MHz, CDCl₃) δ 140.1, 138.2, 136.4, 135.9, 135.2, 134.4, 134.1, 133.9, 130.8, 129.6, 129.4, 128.3, 128.0, 126.8, 58.6, 53.2, 50.9, 26.1, −1.1. IR (Neat Film, NaCl) 3067, 2953, 2918, 2806, 2764, 1652, 1471, 1446, 1427, 1361, 1248, 1169, 1109, 1033, 990, 907, 832, 810, 777, 753 cm⁻¹; HRMS (MM: ESI-APCI+) calc'd for C₂₂H₂₅ClNSSi [M+H]+: 398.1160, found 398.1152.

Example 8.8.4. 5-(Pyridin-2-ylmethyl)-4,5,6,7-tetrahydrothieno[3,2-c]pyridine SM-14

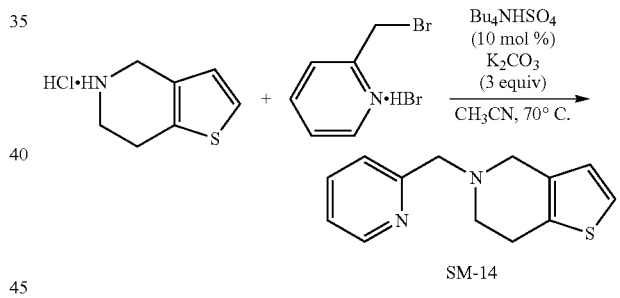

To a flame-dried 50 mL Schlenk flask was added 4,5,6,7-tetrahydrothieno[3,2-c]pyridine HCl salt (1.0 g, 5.7 mmol), 2-(bromomethyl)pyridine HBr salt (2.18 g, 8.6 mmol, 1.5 equiv), Bu₄NHSO4 (0.20 g, 0.6 mmol, 10 mol %), K₂CO₃ (3.94 g, 28.5 mmol, 5 equiv), and 10 mL of acetonitrile. The flask was purged with argon and the reaction was stirred at 70° C. for 18 h. The desired product SM-14 (346.5 mg, 26% yield) was obtained after purification by silica gel flash chromatography (gradient elution, 50→100% Et₂O in hexanes) as a yellow oil. Rf=0.1 (50% Et₂O in hexanes). ¹H NMR (500 MHz, CDCl₃) δ 8.58 (ddd, J=4.9, 1.8, 0.9 Hz, 1H), 7.67 (td, J=7.6, 1.8 Hz, 1H), 7.51 (dt, J=7.9, 1.0 Hz, 1H), 7.19 (ddd, J=7.5, 4.8, 1.2 Hz, 1H), 7.07 (dt, J=5.1, 0.7 Hz, 1H), 6.70 (d, J=5.1 Hz, 1H), 3.89 (s, 2H), 3.64 (t, J=1.7 Hz, 2H), 2.96-2.83 (m, 4H); ¹³C NMR (126 MHz, CDCl₃) δ 158.79, 149.20, 136.52, 133.78, 133.36, 125.22, 123.13, 122.63, 122.13, 63.82, 53.22, 50.89, 25.50; IR (Neat Film, NaCl) 3403, 3062, 2918, 2813, 1648, 1588, 1569, 1473, 1431, 1356, 1320, 1236, 1167, 1109, 1053, 1015, 993, 905, 840, 809, 761 cm⁻¹; HRMS (EI+) calc'd for C₁₃H₁₃SN₂ [(M+H)−H2]+: 229.0799, found 229.0806.

Example 8.8.5. 5-(Pyridin-2-ylmethyl)-2-(triethylsilyl)-4,5,6,7-tetrahydrothieno[3,2-c]pyridine 14

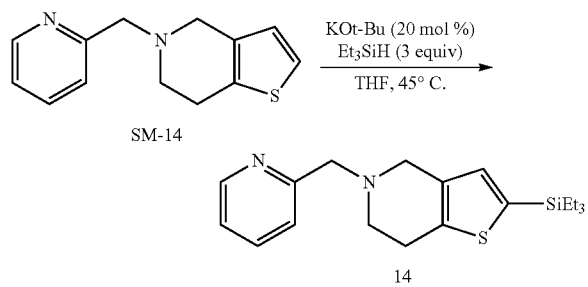

The reaction was conducted according to the General Procedure by heating KOt-Bu (4.5 mg, 0.04 mmol, 20 mol %), 5-(pyridin-2-ylmethyl)-4,5,6,7-tetrahydrothieno[3,2-c]pyridine SM-14 (46.1 mg, 0.2 mmol), Et$_3$SiH (96 μL, 0.6 mmol, 3 equiv), and 0.2 mL of THF at 45° C. for 72 h. The desired product 14 (49.1 mg, 71% yield) was obtained after purification by silica gel flash chromatography (gradient elution, 75→100% Et$_2$O in hexanes) as a colourless oil. Rf=0.5 (75% Et$_2$O hexanes); $^1$H NMR (500 MHz, CDCl$_3$) δ 8.56 (ddd, J=4.9, 1.8, 0.9 Hz, 1H), 7.66 (td, J=7.7, 1.8 Hz, 1H), 7.50 (dt, J=7.8, 1.0 Hz, 1H), 7.17 (ddd, J=7.5, 4.9, 1.2 Hz, 1H), 6.83 (s, 1H), 3.87 (s, 2H), 3.64 (t, J=1.6 Hz, 2H), 2.94 (tt, J=5.3, 1.5 Hz, 2H), 2.86 (dd, J=5.9, 5.0 Hz, 2H), 0.97 (t, J=7.9 Hz, 9H), 0.74 (qd, J=7.7, 0.8 Hz, 6H); $^{13}$C NMR (126 MHz, CDCl$_3$) δ 158.9, 149.1, 138.9, 136.5, 135.3, 133.8, 133.0, 123.1, 122.1, 63.9, 53.2, 50.9, 25.8, 7.4, 4.4; IR (Neat Film, NaCl) 3048, 2951, 2873, 2806, 1588, 1569, 1448, 1430, 1361, 1289, 1235, 1169, 1114, 1031, 1005, 992, 908, 835, 757, 735, 718 cm$^{-1}$; HRMS (EI+) calc'd for C$_{19}$H$_{29}$N$_2$SSi [M+H]+: 345.1821, found 345.1835.

Example 9. Selected Examples of Silylation Catalyzed by Potassium Hydroxide (KOH)

Contrary to earlier findings, it has now been discovered that KOH can be an effective catalyst for the direct silylation of heteroaromatic substances with hydrosilanes under certain conditions. It now appears that by modifying the reaction conditions, this catalyst system can be used with every substrate in which potassium tert-butoxide (or other strong bases) was previously shown to be effective, as described in U.S. patent application Ser. No. 14/043,929 and International Application No. PCT/US2013/062963, both filed Oct. 2, 2013 and as described in the instant specification. However, the use of KOH offers important practical benefits such as lower cost and toxicity, and facilitated reaction set up and purification. Additionally, note that slight changes in conditions can reproducibly alter the degree of substitution (see, e.g., FIG. 7, where a change in operating temperature in furan and bithiophene allowed selective mono- (>10:1 mono-:bis- at 45° C.; 1.2 equivalents silane) and bis-silyl-substitution (>10:1 bis-:mono- at 65° C.; 3 equivalents silane).

As shown above in Example 2, Table 1, KOH was found to be completely non-reactive in this regard under the conditions of the screening tests, and so was believed to be completely inactive in this chemistry. The failure of the reaction to proceed under the conditions described in Table 1 has been repeated and confirmed:

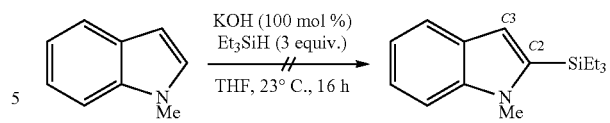

However, by adjusting the reaction conditions, the reaction has been found to proceed with good conversion. This remarkable change in reactivity with only a slight increase in temperature was completely unexpected.

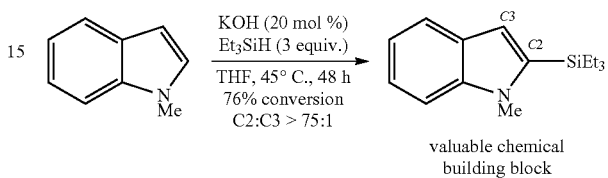

valuable chemical building block

Figure 5A:
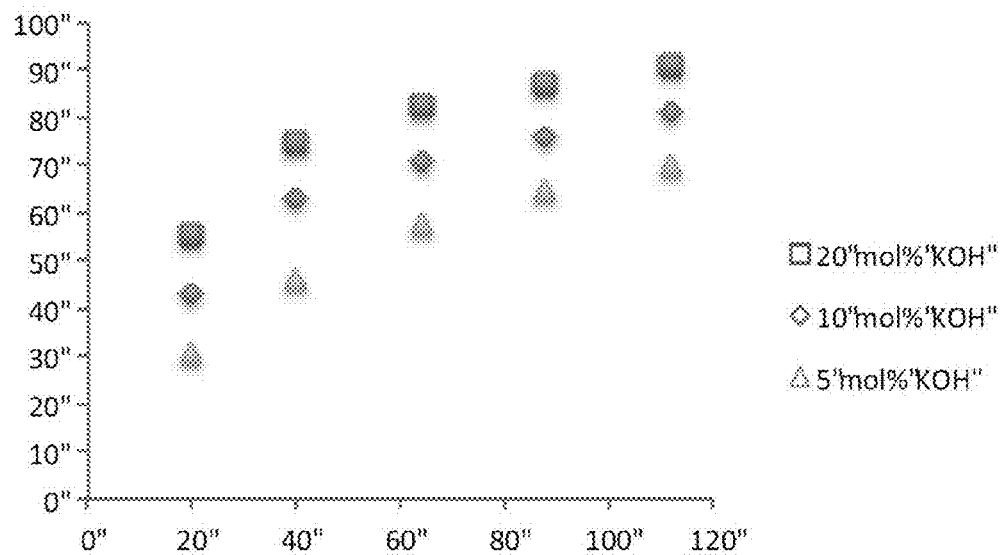
FIGS. 5A/B show conversion vs. time data for the silylation of 1-methylindole with 3 equivalents of Et$_3$SiH and different KOH loadings at 45° C. (time in minutes and conversions in percent).
Figure 5B:
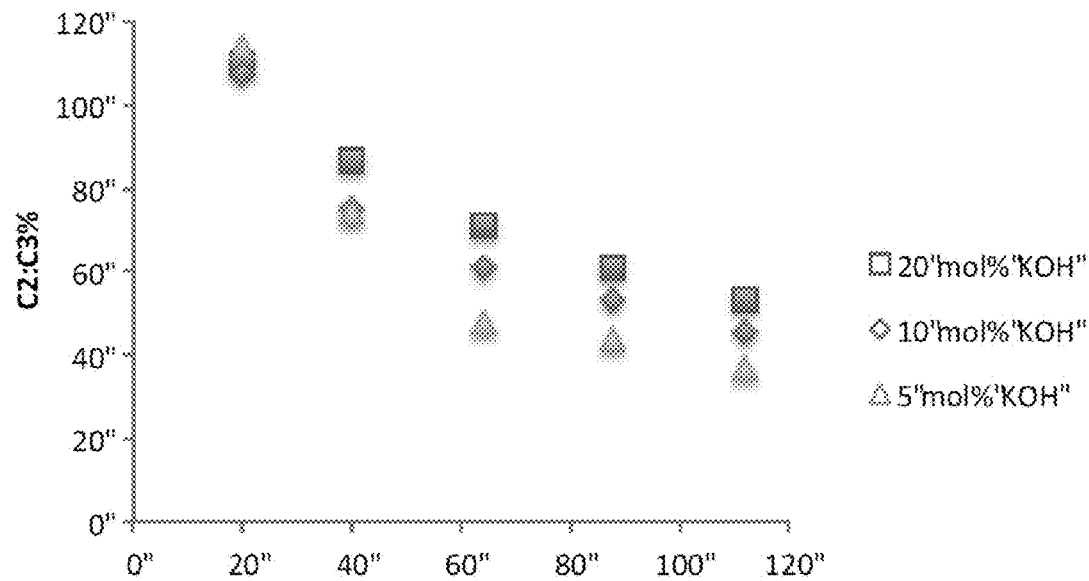
Figures 6, 7:
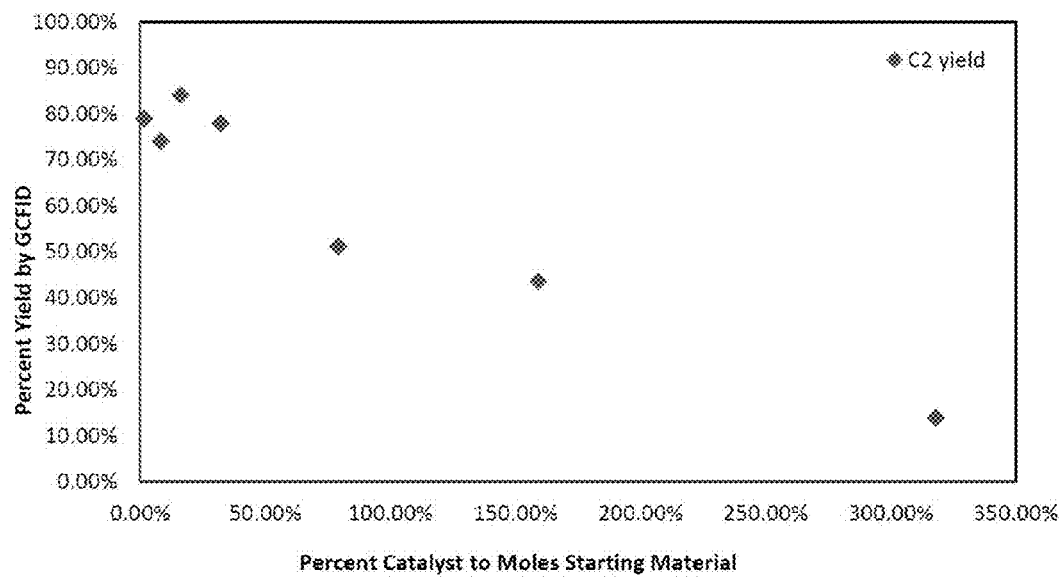
FIG. 6 shows KOH catalyst loading data for the silylation of 1-methylindole with 3 equivalents of Et$_3$SiH at 65° C.
FIG. 7 shows the results of testing representative substrates silylated with a KOH catalytic system. Conditions A: Starting material (0.5 mmol, 1 eq); KOH (0.1 mmol, 5.6 mg, 20 mol %); SiEt$_3$H (1.5 mmol, 3 equiv., 240 μL) in THF (0.5 mL) at 65° C. Conditions B: Starting material (0.5 mmol, 1 eq); KOH (0.1 mmol, 5.6 mg, 20 mol %); SiEt$_3$H (0.6 mmol, 1.2 equiv., 96 μL) in THF (0.5 mL) at 45° C.

See also Table 6 and FIGS. 5A/B and FIG. 6

TABLE 6

Effect of KOH catalyst loading on the silylation of 1-methylindole with 3 equiv. Et$_3$SiH at 65° C.

| KOH, mol % | C2-silylation yield |
|---|---|
| 1.6 | 79 |
| 7.9 | 74 |
| 15.9 | 84 |
| 32 | 78 |
| 79 | 51 |
| 159 | 44 |
| 318 | 14 |

That this catalyst system can operate on the same range of substrates as described for the butoxide/hydride systems is supported by the now discovered operability of the following range of substrates (FIG. 7).

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

Some or all of the following references may be useful in understanding some elements of the present invention or background principles thereof.

1. Zhang, F., Wu, D., Xu, Y. & Feng, X. Thiophene-based conjugated oligomers for organic solar cells. *J. Mater. Chem.* 21, 17590-17600 (2011).
2. Showell, G. A. & Mills, J. S. Chemistry challenges in lead optimization: silicon isosteres in drug discovery. *Drug Discov. Today* 8, 551-556 (2003).

Franz, A. K. & Wilson, S. O. Organosilicon molecules with medicinal applications. *J Med. Chem.* 56, 388-405 (2013).
4. Ball, L. T., Lloyd-Jones, G. C. & Russell, C. A. Gold-catalyzed direct arylation. *Science* 337, 1644-1648 (2012).
5. Denmark, S. E. & Baird, J. D. Palladium-catalyzed cross-coupling reactions of silanolates: a paradigm shift in silicon-based cross-coupling reactions. *Chem. Eur. J.* 12, 4954-4963 (2006).
6. Langkopf, E. & Schinzer, D. Uses of silicon-containing compounds in the synthesis of natural products. *Chem. Rev.* 95, 1375-1408 (1995).
7. Whisler, M. C., MacNeil, S., Snieckus, V. & Beak, P. Beyond thermodynamic acidity: A perspective on the complex-induced proximity effect (CIPE) in deprotonation reactions. *Angew. Chem. Int. Ed.* 43, 2206-2225 (2004).
8. Cheng, C. & Hartwig, J. F. Rhodium-catalyzed intermolecular C—H silylation of arenes with high steric regiocontrol. *Science* 343, 853-857 (2014).
9. Lu, B. & Falck, J. R. Efficient iridium-catalyzed C—H functionalization/silylation of heteroarenes. *Angew. Chem. Int. Ed.* 47, 7508-7510 (2008).
10. Tamao, K., Uchida, M., Izumizawa, T., Furukawa, K. & Yamaguchi, S. Silole derivatives as efficient electron transporting materials. *J. Am. Chem. Soc.* 118, 11974-11975 (1996).
11. Ting, R., Adam, M. J., Ruth, T. J. & Perrin, D. M. Arylfluoroborates and alkylfluorosilicates as potential PET imaging agents: high-yielding aqueous biomolecular 18F-labeling. *J. Am. Chem. S.* 127, 13094-13095 (2005).
12. Du, W., Kaskar, B., Blumbergs, P., Subramanian, P.-K. & Curran, D. P. Semisynthesis of DB-67 and other silatecans from camphothecin by thiol-promoted addition of silyl radicals. *Bioorg. Med. Chem.* 11, 451-458 (2003).
13. Furukawa, S., Kobayashi, J. &. Kawashima, T. Development of a sila-Friedel-Crafts reaction and its application to the synthesis of dibenzosilole derivatives. *J. Am. Chem. Soc.* 131, 14192-14193 (2009).
14. Curless, L. D., Clark, E. R., Dunsford, J. J. & Ingleson, M. J. E-H (E5R3Si or H) bond activation by B(C6F5)3 and heteroarenes; competitive dehydrosilylation, hydrosilylation and hydrogenation. *Chem. Commun.* 50, 5270-5272 (2014).
15. Klare, H. F. T. et al. Cooperative catalytic activation of Si—H bonds by a polar Ru—S bond: regioselective low-temperature C—H silylation of indoles under neutral conditions by a Friedel-Crafts mechanism. *J. Am. Chem. Soc.* 133, 3312-3315 (2011).
16. Seregin, I. V. & Gevorgyan, V. Direct transition metal-catalyzed functionalization of heteroaromatic compounds. *Chem. Soc. Rev.* 36, 1173-1193 (2007). 17. Fedorov, A., Toutov, A. A., Swisher, N. A. & Grubbs, R. H. Lewis-base silane activation: from reductive cleavage of aryl ethers to selective ortho-silylation. *Chem. Sci.* 4, 1640-1645 (2013).
18. Weickgenannt, A. & Oestreich, M. Potassium tert-butoxide-catalyzed dehydrogenative Si—O coupling: reactivity pattern and mechanism of an underappreciated alcohol protection. *Chem. Asian J.* 4, 406-410 (2009).
19. Song, J. J. et al. Organometallic methods for the synthesis and functionalization of azaindoles. *Chem. Soc. Rev.* 36, 1120-1132. (2007).
20. Li, C.-J. & Trost, B. M. Green chemistry for chemical synthesis. *Proc. Natl Acad. Sci.* USA 105, 13197-13202 (2008).
21. Collins, K. D. & Glorius, F. A robustness screen for the rapid assessment of chemical reactions. *Nature Chem.* 5, 597-601 (2013).
22. Seiple, I. B. et al. Direct C2H arylation of electron-deficient heterocycles with arylboronic acids. *J. Am. Chem. Soc.* 132, 13194-13196 (2010).
23. Zhao, Z. & Snieckus, V. Directed ortho metalation-based methodology. Halo-, nitroso-, and boro-induced ipso-desilylation. Link to an in situ Suzuki reaction. *Org. Lett.* 7, 2523-2526 (2005).
24. Lee, M., Ko, S. & Chang, S. Highly selective and practical hydrolytic oxidation of organosilanes to silanols catalyzed by a ruthenium complex. *J. Am. Chem. Soc.* 122, 12011-12012 (2000).
25. Hansen, M. M. et al. Lithiated benzothiophenes and benzofurans require 2-silyl protection to avoid anion migration. *Synlett* 8, 1351-1354 (2004).
26. Wang, Y. & Watson, M. D. Transition-metal-free synthesis of alternating thiopheneperfluoroarene copolymers. *J. Am. Chem. Soc.* 128, 2536-2537 (2006).
27. Kuznetsov, A., Onishi, Y., Inamoto, Y. & Gevorgyan, Y. Fused heteroaromatic dihydrosiloles: synthesis and double-fold modification, *Org. Lett.* 15, 2498-2501 (2013).
28. Oyamada, J., Nishiura, M. & Hou, Z. Scandium-catalyzed silylation of aromatic C—H bonds, *Angew. Chem. Int. Ed.* 50, 10720-10723 (2011).
29. Kakiuchi, F., Tsuchiya, K., Matsumoto, M., Mizushima, E. & Chatani, N. $Ru_3(CO)_{12}$-catalyzed silylation of benzylic C—H bonds in arylpyridines and arylpyrazoles with hydrosilanes via C—H bond cleavage. *J. Am. Chem. Soc.* 126, 12792-12793 (2004).
30. Sakakura, T., Tokunaga, Y., Sodeyama, T. & Tanaka, M. Catalytic C—H activation. Silylation of arenes with hydrosilane or disilane by $RhCl(CO)(PMe_3)_2$ under irradiation. *Chem. Lett.* 16, 2375-2378 (1987).

Each patent, patent application, and publication cited or described in this document is hereby incorporated herein by reference, each in its entirety, for all purposes.

What is claimed:
1. A method comprising contacting an organic substrate comprising an aromatic moiety with a mixture comprising (a) at least one hydrosilane and (b) potassium hydroxide (KOH), under conditions sufficient to silylate the organic substrate, the method resulting in the formation of a silylated organic substrate, wherein the silylated organic substrate has a carbon-silicon bond in a position corresponding to a position on the aromatic moiety having a carbon-hydrogen bond, unless:
   (a) the aromatic moiety is an aryl moiety having an alkyl substituent, in which case the silylated organic substrate has a carbon-silicon bond on the carbon alpha to the aryl moiety; or
   (b) the aromatic moiety is one having an alkylthioether substituent, in which case the silylated organic substrate has a carbon-silicon bond on the carbon alpha to the thioether sulfur; or
   (c) the aromatic moiety is a pyridinyl moiety having alkyl substituents on one or both C2-and C6-positions, in which case the silylated organic substrate has a carbon-silicon bond on the carbon alpha to the pyridinyl ring; or
   (d) the aromatic moiety is a heteroaryl moiety comprising a 5-membered heteroaryl ring having no C—H substituents in its C-2 or C-5 position and at least one alkyl substituent in the C-2 or C-5 position, in which case the silylated organic substrate has a carbon-silicon bond on the carbon alpha to the 5-membered heteroaryl ring.

2. The method of claim 1, wherein the mixture and organic substrate are free of added transition-metal species.

3. The method of claim 1, wherein the at least one hydrosilane comprises a hydrosilane of Formula (I) or Formula (II):

   (I)

   (II)

where m is 1, 2, or 3;
n is 10 to 100; and
each R is independently optionally substituted $C_{1-12}$ alkyl or $C_{1-12}$ heteroalkyl, optionally substituted $C_{6-20}$ aryl or $C_{5-20}$ heteroaryl, optionally substituted $C_{7-30}$ alkaryl or $C_{6-30}$ heteroalkaryl, optionally substituted $C_{7-30}$ aralkyl or $C_{6-30}$ heteroaralkyl, optionally substituted —O—$C_{1-12}$ alkyl or —O—$C_{1-12}$ heteroalkyl, optionally substituted —O—$C_{7-20}$ aryl or —O—$C_{5-20}$ heteroaryl, optionally substituted —O—$C_{7-30}$ alkaryl or —O—$C_{6-30}$ heteroalkaryl, or optionally substituted —O—$C_{7-30}$ aralkyl or —O—$C_{6-30}$ heteroaralkyl, and, if substituted, the substituents may be phosphonato, phosphoryl, phosphanyl, phosphino, sulfonato, $C_1$-$C_{20}$ alkylsulfanyl, $C_{6-20}$ arylsulfanyl, $C_1$-$C_{20}$ alkylsulfonyl, $C_{6-20}$ arylsulfonyl, $C_1$-$C_{20}$ alkylsulfinyl, $C_{6-20}$ arylsulfinyl, sulfonamido, amino, amido, imino, nitro, nitroso, hydroxyl, $C_1$-$C_{20}$ alkoxy, $C_{6-20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, or where the substituents optionally provide a tether to an insoluble or sparingly soluble support media comprising alumina, silica, or carbon.

4. The method of claim 1, wherein the at least one hydrosilane is $(R)_3SiH$, where each R is independently $C_{1-6}$ alkyl.

5. The method of claim 1, wherein the aromatic moiety contains a methyl substituent, and the silylated organic substrate has a carbon-silicon bond in a position corresponding to a carbon-hydrogen bond of the methyl substituent.

6. The method of claim 1, wherein the aromatic moiety comprises an exocyclic aromatic methyl thioether, and the silylated organic substrate has a carbon-silicon bond on the thioether methyl substituent.

7. The method of claim 1, wherein the organic substrate comprises a heteroaryl moiety.

8. The method of claim 7, wherein the organic substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, or dibenzothiophene.

9. The method of claim 1, wherein the organic substrate comprises at least one of the following aromatic moieties:

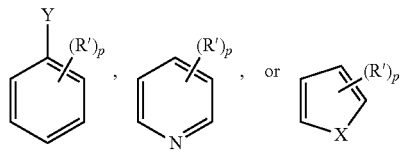

where X is N—R", O, or S;
Y is H, N(R")$_2$, O—R", or S—R";
p is 0 to 3;
R' is alkyl, halo, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di-haloalkyl-substituted carbamoyl, di aryl-substituted carbamoyl, di-alkyl-substituted thiocarbamoyl, di-aryl-substituted thiocarbamoyl, di-N-alkyl,N-aryl-substituted thiocarbamoyl, cyano, cyanato, thiocyanato, di-alkyl-substituted amino, di-aryl-substituted amino, arylimino (—CR=N(aryl), where R=alkyl, aryl, alkaryl, or aralkyl), nitro, nitroso, alkylsulfanyl, arylsulfanyl, alkylsulfinyl, arylsulfinyl, alkyl sulfonyl, boronato (—B(OR)$_2$ where R is alkyl or other hydrocarbyl); or (R')$_p$ comprises an optionally substituted fused methylene linked diether, ethylene linked diether, or propylene linked diether, aryl, or heteroaryl moiety; and
R" is an amine protecting group or an optionally substituted alkyl, aryl, heteroaryl, alkaryl or alk-heteroaryl.

10. The method of claim 1, wherein the organic substrate comprises at least one of the following aromatic moieties:

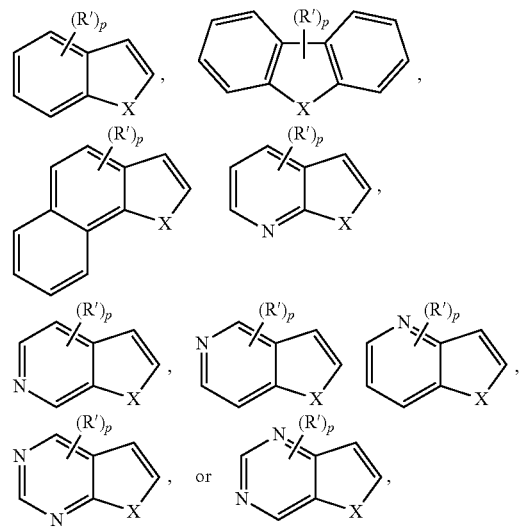

where X is N—R", O, or S;
p is 0 to 3;
R' is alkyl, halo, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di aryl-substituted carbamoyl, di-alkyl-substituted thiocarbamoyl, di-aryl-substituted thiocarbamoyl, di-N-alkyl,N-aryl-substituted thiocarbamoyl, cyano, cyanato, thiocyanato, di-alkyl-substituted amino, di-aryl-substituted amino, arylimino (—CR=N(aryl), where R=alkyl, aryl, alkaryl, or aralkyl), nitro, nitroso, alkylsulfanyl, arylsulfanyl, alkylsulfinyl, arylsulfinyl, alkyl sulfonyl, boronato (—B(OR)$_2$ where R is alkyl or other hydrocarbyl); or (R')$_p$ comprises an optionally substituted fused methylene linked diether, ethylene linked diether, or propylene linked diether, aryl, or heteroaryl moiety.

11. The method of claim 9, wherein the organic substrate comprises a heteroaryl moiety of structure:

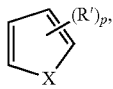

where p is 1 or 2 and the silylation occurs at the C-2 position of the heteroaryl ring, unless p is 2, and R' is alkyl located in the C-2 and C-5 positions, in which case the silylation occurs at a carbon alpha to the heteroaryl ring.

12. The method of claim 10, wherein the organic substrate comprises a heteroaryl moiety of structure:

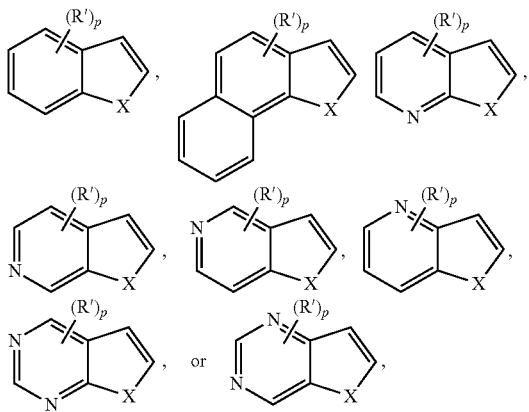

where p is 1 or 2 and the silylation occurs at the C-2 position of the 5-membered heteroaryl ring unless R' is an alkyl located at the C-2 position of the 5-membered heteroaryl ring, in which case the silylation occurs at the alpha carbon located in the C-2 position of the 5-membered heteroaryl ring.

13. The method of claim 1, wherein the organic substrate is polymeric, oligomeric, or a polymeric precursor.

14. The method of claim 1, wherein the silylated organic substrate is further reacted under conditions sufficient to couple the silylated organic substrate with a second aromatic compound to form a biaromatic product, the method resulting in the formation of the biaromatic product.

15. The method of claim 1, wherein the silylated organic substrate is further reacted under conditions sufficient to convert the silylated organic substrate to a hydroxylated, alkoxylated, aryloxylated, or alkyl or aryl carboxylated product, the method resulting in the formation of the hydroxylated, alkoxylated, aryloxylated, or alkyl or aryl carboxylated product.

16. The method of claim 1, wherein the silylated organic substrate is further reacted under conditions sufficient to convert the silylated organic substrate to an aromatic alpha-olefin product, the method resulting in the formation of the aromatic alpha-olefin product.

17. The method of claim 1, wherein the silylated organic substrate is further reacted under conditions sufficient to convert the silylated organic substrate to an aromatic chloro, bromo, fluoro, iodo, nitrate, or nitrite, the method resulting in the formation of the aromatic chloro, bromo, fluoro, iodo, nitrate, or nitrite.

18. The method of claim 1, wherein the silylated organic substrate is further reacted under conditions sufficient to convert the silylated organic substrate to an aromatic boronic halide or boronic ester, the method resulting in the formation of the aromatic boronic halide or boronic ester.

19. The method of claim 1, where the silylated organic substrate is a silylated thiophene substrate, wherein the silylated thiophene substrate is further reacted under conditions sufficient to convert the silylated thiophene substrate to an alternating thiophene-perfluoroarene copolymer.

20. The method of claim 7, wherein the organic substrate comprises a furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzothiophene, isobenzofuran, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

21. The method of claim 3, where m is 1 or 2.

22. The method of claim 3, where each R is independently $C_1$-$C_6$ alkyl, phenyl, tolyl, benzyl, phenethyl, or pyridinyl.

23. The method of claim 9, wherein each R" is independently $C_1$-$C_6$ alkyl, phenyl, tolyl, benzyl, or phenethyl.

24. A composition comprising:
(a) an organic substrate comprising an aromatic moiety;
(b) at least one hydrosilane;
(c) potassium hydroxide (KOH); and
(d) a silylated derivative of the organic substrate, wherein the silylated derivative has a C—Si bond in a position corresponding to a position in the organic substrate having a C—H bond as described in claim 1.

25. The composition of claim 24, wherein the composition is free of added transition-metal species.

26. The composition of claim 24, wherein the at least one hydrosilane comprises a hydrosilane of Formula (I) or Formula (II):

$$(R)_{4-m}Si(H)_m \quad (I)$$

$$R\text{—}[\text{—}SiH(R)\text{—}O\text{—}]_n\text{—}R \quad (II)$$

where m is 1, 2, or 3;
n is 10 to 100; and
each R is independently optionally substituted $C_{1-12}$ alkyl or $C_{1-12}$ heteroalkyl, optionally substituted $C_{6-20}$ aryl or $C_{5-20}$ heteroaryl, optionally substituted $C_{7-30}$ alkaryl or $C_{6-30}$ heteroalkaryl, optionally substituted $C_{7-30}$ aralkyl or $C_{6-30}$ heteroaralkyl, optionally substituted —O—$C_{1-12}$ alkyl or —O—$C_{1-12}$ heteroalkyl, optionally substituted —O—$C_{7-20}$ aryl or —O—$C_{5-20}$ heteroaryl, optionally substituted —O—$C_{7-30}$ alkaryl or —O—$C_{6-30}$ heteroalkaryl, or optionally substituted —O—$C_{7-30}$ aralkyl or —O—$C_{6-30}$ heteroaralkyl, and, if substituted, the substituents may be phosphonato, phosphoryl, phosphanyl, phosphino, sulfonato, $C_1$-$C_{20}$ alkylsulfanyl, $C_{6-20}$ arylsulfanyl, $C_1$-$C_{20}$ alkylsulfonyl, $C_{6-20}$ arylsulfonyl, $C_1$-$C_{20}$ alkylsulfinyl, $C_{6-20}$ arylsulfinyl, sulfonamido, amino, amido, imino, nitro, nitroso, hydroxyl, $C_1$-$C_{20}$ alkoxy, $C_{6-20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, or where the substituents optionally provide a tether to an insoluble or sparingly soluble support media comprising alumina, silica, or carbon.

27. The composition of claim 24, wherein the at least one hydrosilane is (R)₃SiH, where each R is independently $C_{1-6}$ alkyl.

28. The composition of claim 24, wherein the aromatic moiety comprises a benzene, biphenyl, naphthalene, or anthracene ring structure having a methyl substituent, wherein silylated derivative has a carbon-silicon bond on the methyl substituent.

29. The composition of claim 24, wherein the aromatic moiety comprises an exocyclic aromatic methyl thioether, and the silylated derivative has a carbon-silicon bond on the thioether methyl substituent.

30. The composition of claim 24, wherein the organic substrate comprises a heteroaryl moiety.

31. The composition of claim 30, wherein the organic substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, or dibenzothiophene.

32. The composition of claim 24, wherein the organic substrate comprises at least one of the following aromatic moieties:

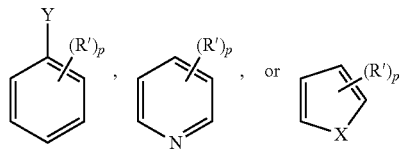

where X is N—R", O, or S;
Y is H, N(R")₂, O—R", or S—R"
p is 0 to 3;
R' is alkyl, halo, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di-haloalkyl-substituted carbamoyl, di aryl-substituted carbamoyl, di-alkyl-substituted thiocarbamoyl, di-aryl-substituted thiocarbamoyl, di-N-alkyl,N-aryl-substituted thiocarbamoyl, cyano, cyanato, thiocyanato, di-alkyl-substituted amino, di-aryl-substituted amino, arylimino (—CR═N(aryl), where R=alkyl, aryl, alkaryl, or aralkyl), nitro, nitroso, alkylsulfanyl, arylsulfanyl, alkylsulfinyl, arylsulfinyl, alkyl sulfonyl, boronato (—B(OR)₂ where R is alkyl or other hydrocarbyl); or (R')ₚ comprises an optionally substituted fused methylene linked diether, ethylene linked diether, or propylene linked diether, aryl, or heteroaryl moiety; and
R" is an amine protecting group or an optionally substituted alkyl, aryl, heteroaryl, alkaryl or alk-heteroaryl.

33. The composition of claim 24, wherein the organic substrate comprises at least one of the following aromatic moieties:

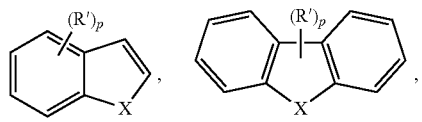

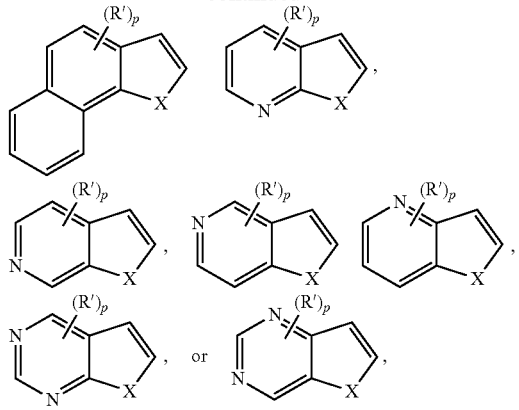

where X is N—R", O, or S;
p is 0 to 3;
R' is alkyl, halo, sulfhydryl, alkoxy, aryloxy, aralkyloxy, alkaryloxy, acyl, acyloxy, alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di aryl-substituted carbamoyl, di-alkyl-substituted thiocarbamoyl, di-aryl-substituted thiocarbamoyl, di-N-alkyl, N-aryl-substituted thiocarbamoyl, cyano, cyanato, thiocyanato, di-alkyl-substituted amino, di-aryl-substituted amino, arylimino (—CR═N(aryl), where R=alkyl, aryl, alkaryl, or aralkyl), nitro, nitroso, alkylsulfanyl, arylsulfanyl, alkylsulfinyl, arylsulfinyl, alkyl sulfonyl, boronato (—B(OR)₂ where R is alkyl or other hydrocarbyl); or (R')ₚ comprises an optionally substituted fused methylene linked diether, ethylene linked diether, or propylene linked diether, aryl, or heteroaryl moiety.

34. The composition of claim 32, wherein the organic substrate comprises a heteroaryl moiety of structure:

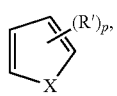

where p is 1 or 2 and the silylation occurs at the C-2 position of the heteroaryl ring, unless p is 2, and R' is alkyl located in the C-2 and C-5 positions, in which case the silylated derivative has a carbon-silicon bond on a carbon alpha to the heteroaryl moiety.

35. The composition of claim 32, wherein the organic substrate comprises a heteroaryl moiety of structure:

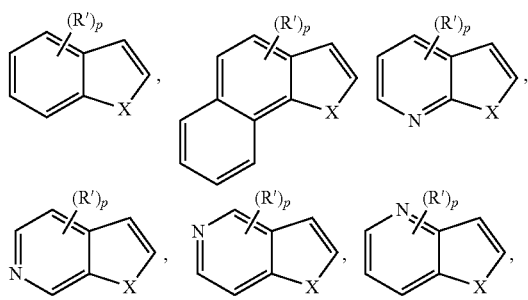

-continued

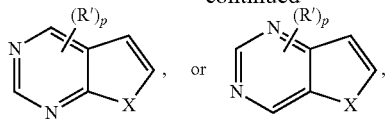

where p is 1 or 2 and the silylation occurs at the C-2 position of the 5-membered heteroaryl ring unless R' is an alkyl located at the C-2 position of the 5-membered heteroaryl ring, in which case the silylated derivative has a carbon-silicon bond on the alpha carbon located in the C-2 position of the 5-membered heteroaryl ring.

36. The composition of claim 24, wherein the organic substrate is polymeric, oligomeric, or a polymeric precursor.

37. The method of claim 5, wherein the aromatic moiety comprises a benzene, biphenyl, naphthalene, or anthracene ring structure having a methyl substituent, wherein silylated organic substrate has a carbon-silicon bond on the methyl substituent.

* * * * *